US008232058B2

(12) United States Patent
McBride et al.

(10) Patent No.: US 8,232,058 B2
(45) Date of Patent: Jul. 31, 2012

(54) MULTIPLEX DETECTION OF RESPIRATORY PATHOGENS

(75) Inventors: Mary McBride, Brentwood, CA (US); Thomas Slezak, Livermore, CA (US); James M. Birch, Albany, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 503 days.

(21) Appl. No.: 12/161,291

(22) PCT Filed: Jan. 22, 2007

(86) PCT No.: PCT/US2007/060872

§ 371 (c)(1), (2), (4) Date: Nov. 25, 2008

(87) PCT Pub. No.: WO2008/042450

PCT Pub. Date: Apr. 10, 2008

(65) Prior Publication Data

US 2009/0305229 A1 Dec. 10, 2009

Related U.S. Application Data

(60) Provisional application No. 60/966,523, filed on Jan. 20, 2006.

(51) Int. Cl.
*C12Q 1/68* (2006.01)
*C12P 19/34* (2006.01)
*C07H 21/04* (2006.01)

(52) U.S. Cl. .................... 435/6.12; 435/91.2; 536/24.33

(58) Field of Classification Search ............. 435/6, 91.2, 435/6.12; 536/24.33
See application file for complete search history.

(56) References Cited

U.S. PATENT DOCUMENTS

| | | | | |
|---|---|---|---|---|
| 5,187,060 | A * | 2/1993 | Cerutti et al. | 435/6 |
| 6,429,001 | B1 * | 8/2002 | Hardy | 435/235.1 |
| 2003/0233675 | A1 * | 12/2003 | Cao et al. | 435/6 |
| 2004/0191761 | A1 * | 9/2004 | Routes | 435/5 |
| 2005/0009008 | A1 * | 1/2005 | Robinson et al. | 435/5 |

FOREIGN PATENT DOCUMENTS

| | | | |
|---|---|---|---|
| WO | 9716570 | * | 5/1997 |
| WO | 2004057021 | * | 7/2004 |

OTHER PUBLICATIONS

The nucleic acid sequence search reports for SEQ ID No. 1-10.*
Lowe et al. Nucleic acid research, vol. 18(7), p. 1757-1761.*
Stratagen Catalog, 1988.*
Marozin et al. J. Gen. Virol. 2002, vol. 83 (PT4), p. 735-745.*
Ghedin et al. Nature, 2005, vol. 437, p. 7062.*
The nucleic acid sequence search reports, (Accession No., CY002152, L11128, AF116198, AF084281, CY014722, U67783, U79452, AF100399, ADR98683, X57559, AY210026, AY534913, AR222046).*
Schafer et al. (Virology, 194(2), 1993, p. 781-788).*
Makarova et al. (J. Gen. Virol. 1999, 80(Pt12), p. 3167-3171).*
Hiromoto et al. (J. Gen. Virol., 2000, Vo. 81, p. 1293-1303).*
Obenauer et al. (Science, 2006, vol. 311, p. 1576-1580).*
Garcia et al. (Virus Research, 1997, vol. 51, p. 115-124).*
Lindstrom et al. (J. of Virology, 1999, vol. 73(5), p. 4413-4426).*
Kawano et al. (Nucleic acids research, 1991, vol. 19(10), p. 2739-2746).*
Lindstrom et al. (Virology, 2004, vol. 328, p. 101-119).*
PCT International Search Report and Written Opinion, PCT Application No. PCT/US07/60872, Oct. 31, 2008, 7 pages.
Barenfanger et al., Clinical and Financial Benefits of Rapid Detection of Respiratory Viruses: An Outcomes Study, Journal of Clinical Microbiology, Aug. 2000, pp. 2824-2828, vol. 38, No. 8, 5 pages.
Buck et al., Design Strategies and Performance of Custom DNA Sequencing Primers, BioTechniques, Sep. 1999, pp. 528-536, vol. 27, No. 3, 9 pages.
Dingle et al., Stable and Noncompetitive RNA Internal Control for Routine Clinical Diagnostic Reverse Transcription-PCR, Journal of Clinical Microbiology, Mar. 2004, pp. 1003-1011, vol. 42, No. 3, 9 pages.
Harris et al., Liquid Array Single-handedly Detects Bounty of BW Agents, Analytical Chemistry, May 1, 2003, p. 202 A, 1 page.
Hatchette et al., Influenza A Viruses in Feral Canadian Ducks: Extensive Reassortment in Nature, Journal of General Virology, 2004, pp. 2327-2337, vol. 85, 11 pages.
Kuypers et al., Comparison of Real-Time PCR Assays with Fluorescent-Antibody Assays for Diagnosis of Respiratory Virus Infections in Children, Journal of Clinical Microbiology, Jul. 2006, pp. 2382-2388, vol. 44, No. 7, 7 pages.
Létant et al., Multiplexed Reverse Transcriptase PCR Assay for Identification of Viral Respiratory Pathogens at the Point of Care, Journal of Clinical Microbiology, Nov. 2007, pp. 3498-3505, vol. 45, No. 11, 8 pages.
McBride et al., Multiplexed Liquid Arrays for Simultaneous Detection of Simulants of Biological Warfare Agents, Analytical Chemistry, Mar. 6, 2003, pp. 1924-1930, vol. 75, No. 8, 7 pages.
McBride et al., Autonomous Detection of Aerosolized *Bacillus anthracis* and *Yersinia pestis*, Analytical Chemistry, Sep. 18, 2003, pp. 5923-5299; vol. 75, No. 20, 7 pages.
Osiowy et al., Direct Detection of Respiratory Syncytial Virus, Parainfluenza Virus, and Adenovirus in Clinical Respiratory Specimens by Multiplex Reverse Transcription-PCR Assay, Journal of Clinical Microbiology, Nov. 1998, pp. 3149-3154, vol. 36, No. 11, 6 pages.
Ruest et al., Comparison of the Directigen Flu A+B Test, the QuickVue Influenza Test, and Clinical Case Definition to Viral Culture and Revese Transcription-PCR for Rapid Diagnosis of Influenza Virus Infection, Journal of Clinical Microbiology, Aug. 2003, pp. 3487-3493, vol. 41, No. 8, 7 pages.

(Continued)

*Primary Examiner* — Kenneth R. Horlick
*Assistant Examiner* — Joyce Tung
(74) *Attorney, Agent, or Firm* — Fenwick & West LLP

(57) ABSTRACT

Described are kits and methods useful for detection of respiratory pathogens (influenza A (including subtyping capability for H1, H3, H5 and H7 subtypes) influenza B, parainfluenza (type 2), respiratory syncytial virus, and adenovirus) in a sample. Genomic sequence information from the respiratory pathogens was analyzed to identify signature sequences, e.g., polynucleotide sequences useful for confirming the presence or absence of a pathogen in a sample. Primer and probe sets were designed and optimized for use in a PCR based, multiplexed Luminex assay to successfully identify the presence or absence of pathogens in a sample.

18 Claims, 14 Drawing Sheets

OTHER PUBLICATIONS

Pehler-Harrington et al., Rapid Detection and Identification of Human Adenovirus Species by Adenoplex, a Multplex PCR-Enzyme Hybridization Assay, Journal of Clinical Microbiology, Sep. 2004, pp. 4072-4076, vol. 42, No. 9, 5 pages.

Shaw et al., Molecular Changes Associated with the Transmission of Avian Influenza H5N1 and H9N2 Viruses to Humans, Journal of Medical Virology, 2002, pp. 107-114, vol. 66, 10 pages.

Syrmis et al., A Sensitive, Specific, and Cost-Effective Multiplex Reverse Transcriptase-PCR Assay for the Detection of Seven Common Respiratory Viruses in Respiratory Samples, Journal of Molecular Diagnostics, May 2004, pp. 125-131, vol. 6, No. 2, 7 pages.

Templeton et al., Rapid and Sensitve Method Using Multiplex Real-Time PCR for Diagnosis of Infections by Influenza A and Influenza B Viruses, Respiratory Syncytial Virus, and Parainfluenza Viruses 1, 2, 3 and 4, Apr. 2004, pp. 1564-1569, vol. 42, No. 4, 6 pages.

Van Elden, et al., Simultaneous Detection of Influenza Viruses A and B Using Real-Time Quantitative PCR, Journal of Clinical Microbiology, Jan. 2001, pp. 196-200, vol. 39, No. 1, 5 pages.

Wilson et al, A Multiplexed PCR-coupled Liquid Bead Array for the Simultaneous Detection of Four Biothreat Agents, Molecular and Cellular Probes, 2005, pp. 137-144, vol. 19, 8 pages.

* cited by examiner

SEQUENCE LISTING

<160> NUMBER OF SEQ ID NOS: 375

<210> SEQ ID NO 1
<211> LENGTH: 106
<212> TYPE: DNA
<213> ORGANISM: Influenza A virus

<400> SEQUENCE: 1
gaccaatcct gtcacctctg actaagggga ttttaggatt tgtgtttacg ctcaccgtgc 60
ccagtgagcg aggactgcag cgtagacgct ttgtccaaaa tgccct 106

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gaccratcct gtcacctctg ac 22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
agggcatttt ggacaaakcg tcta 24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 4
cgtgcccagt gagcgaggac tgca 24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 5
ttgacctagt tgttctcgcc a 21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 6
tgcagtcctc gctcactggg cacg 24

<210> SEQ ID NO 7
<211> LENGTH: 137
<212> TYPE: DNA
<213> ORGANISM: Influenza A virus

<400> SEQUENCE: 7
ctttcagcta cagatgcaga cacaatatgt ataggctacc atgcgaacaa ttcaaccgac 60
actgttgaca cagtcctcga gaagaatgtg acagtaacac actctgtcaa cctatttgag 120
gacagtcaca atgggaa 137

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
ctttcagcta cagatgcaga caca 24

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
ttcccattgt gactgtcctc aa 22

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 10
cgaacaattc aaccgacact gttgacaca 29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 11
cgaacaattc aaccgacact gttgacaca 29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 12
cgaacaattc aaccgacact gttgacaca 29

-continued

<210> SEQ ID NO 13
<211> LENGTH: 178
<212> TYPE: DNA
<213> ORGANISM: Influenza A virus

<400> SEQUENCE: 13
gccattaacg ggattacaaa caaggtgaat tctgtaattg agaaaatgaa cactcaattc 60
acagctgtgg gcaaagaatt caacaaattg gaaagaagga tggaaaactt aaataaaaag 120
gttgatgatg ggtttctaga cgtttggaca tataatgcag aattgttggt tctactgg 178

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gccattaacg ggattacaaa caag 24

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ccagtagaac caacaattct gcattat 27

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 16
tcgagaaaat gaacactcaa ttcacagctg tg 32

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 17
tcgagaaaat gaacactcaa ttcacagctg tg 32

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 18
tcgagaaaat gaacactcaa ttcacagctg tg 32

-continued

<210> SEQ ID NO 19
<211> LENGTH: 123
<212> TYPE: DNA
<213> ORGANISM: Influenza A virus

<400> SEQUENCE: 19
accgagacgg tcgacacaat tctagagcgg aatgtcactg tgacccatgc caagaacatc 60
ctcgagaaaa cccataacgg aaaattatgc aaactaaatg gaatccctcc acttgaacta 120
ggg 123

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
ccctagttca agtggaggga ttc 23

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
accgagacgg tcgacacaa 19

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 22
catgggtcac agtgacattc cgctctaga 29

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 23
catgggtcac agtgacattc cgctctaga 29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 24
catgggtcac agtgacattc cgctctaga 29

<210> SEQ ID NO 25

<211> LENGTH: 190
<212> TYPE: DNA
<213> ORGANISM: Influenza A virus

<400> SEQUENCE: 25
acacaatctt ggagcgaaac gtcaccgtga ctcatgccaa ggacattctt gagaaaacgc 60
ataatgggaa gttgtgcaga ttgagcggga tccctccatt ggaattgggg gattgcagca 120
ttgcggggtg gctccttgga aatccggaat gtgaccggct cttaagtgta cctgaatggt 180
cctatatagt 190

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
acacaatctt ggagcgaaac g 21

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
actatatagg accattcagg cactt 25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 28
tgcagattaa gcgggatccc tccat 25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 29
tgcagattaa gcgggatccc tccat 25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 30
tgcagattaa gcgggatccc tccat 25

<210> SEQ ID NO 31
<211> LENGTH: 190
<212> TYPE: DNA
<213> ORGANISM: Influenza A virus

<400> SEQUENCE: 31
acacaatctt ggagcgaaac gtcaccgtga ctcatgccaa ggacattctt gagaaaacgc 60
ataatgggaa gttgtgcaga ttgagcggga tccctccatt ggaattgggg gattgcagca 120
ttgcggggtg gctccttgga aatccggaat gtgaccggct cttaagtgta cctgaatggt 180
cctatatagt 190

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
atgctgagga tatgggcaat g 21

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gatatggcaa aggaaatcca tagg 24

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 34
cattaaacaa ccggttccag atcaaaggtg t 31

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 35
cattaaacaa ccggttccag atcaaaggtg t 31

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 36
cattaaacaa ccggttccag atcaaaggtg t 31

-continued

<210> SEQ ID NO 37
<211> LENGTH: 111
<212> TYPE: DNA
<213> ORGANISM: Influenza A virus

<400> SEQUENCE: 37
gatctaaatg gagtgaaacc tctcattttg agggattgta gtgtagctgg atggctcctc 60
ggaaacccta tgtgtgacga attcatcaat gtgccggaat ggtcttacat a 111

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gatctaaatg gagtgaagcc tctcat 26

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
tatgtaagac cattccggca cat 23

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 40
ctggatggct cctcggaaac cctatgt 27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
ctggatggct cctcggaaac cctatgt 27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 42
ctggatggct cctcggaaac cctatgt 27

<210> SEQ ID NO 43
<211> LENGTH: 160

-continued

<212> TYPE: DNA
<213> ORGANISM: Influenza A virus

<400> SEQUENCE: 43
gggaggaaat agacggagtc aaattggaat caatgggcac ttatcagata ctatcaatct 60
actcaacagt ggcgagttcc ctagcactgg caatcatggt agctggtcta tctttttgga 120
tgtgctccaa tggatcattg cagtgcagaa tttgcatcta 160

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gggaggaaat agacggagtc aaa 23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
tagatgcaaa ttctgcactg caa 23

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 46
ctggatggct cctcggaaac cctatgt 27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 47
ctggatggct cctcggaaac cctatgt 27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 48
tcaacagtgg cgagttccct agcactg 27

<210> SEQ ID NO 49
<211> LENGTH: 119
<212> TYPE: DNA

<213> ORGANISM: Influenza A virus

<400> SEQUENCE: 49
gtatgggtac caccatagca atgagcaggg gagtgggtac gctgcagaca aagaatccac 60
tcaaaaggca atagatggag tcaccaataa ggtcaactcg atcattgaca aaatgaaca 119

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
gtatgggtac caccatagca atga 24

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
tgttcatttt gtcaatgatc gagtt 25

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 52
tgcagacaaa gaatccactc aaaaggcaa 29

<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 53
tgcagacaaa gaatccactc aaaaggcaa 29

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 54
tgcagacaaa gaatccactc aaaaggcaa 29

<210> SEQ ID NO 55
<211> LENGTH: 197
<212> TYPE: DNA
<213> ORGANISM: Influenza A virus

<400> SEQUENCE: 55

-continued

```
gacaatgaat gcatggaaag tgtgagaaat ggaacgtatg actatccaca atactcagaa     60

gaatcaaggc taaacaggga ggagatagat ggagtcaaat tggaatccgt gggcacttat    120

cagatactat caatctactc aacagtggca agttccctag cactggcaat catggtagct    180

ggtctgtctt tttggat                                                   197


<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

gacaatgaat gtatggaaag tgtgaga                                         27


<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

atccaaaaag atagaccagc tatcatg                                         27


<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58

cagtggcaag ttccctagca ctggca                                          26


<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59

cagtggcaag ttccctagca ctggca                                          26


<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60

cagtggcaag ttccctagca ctggca                                          26


<210> SEQ ID NO 61
<211> LENGTH: 197
<212> TYPE: DNA
<213> ORGANISM: Influenza A virus
```

<400> SEQUENCE: 61
gacaatgaat gcatggaaag tgtgagaaat ggaacgtatg actatccaca atactcagaa 60
gaatcaaggc taaacaggga ggagatagat ggagtcaaat tggaatccgt gggcacttat 120
cagatactat caatctactc aacagtggca agttccctag cactggcaat catggtagct 180
ggtctgtctt tttggat 197

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
gatcccaatg acacagtgac ctt 23

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ttccccacag ttctagggtt ga 22

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 64
catagcccct gacagggcaa gtttctttag 30

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 65
catagcccct gacagggcaa gtttctttag 30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 66
catagcccct gacagggcaa gtttctttag 30

<210> SEQ ID NO 67
<211> LENGTH: 103
<212> TYPE: DNA
<213> ORGANISM: Influenza B virus -continued

<400> SEQUENCE: 67
tcctcaactc actcttcgag cgttttaatg aaggacattc aaagccaatt cgagcagctg 60
aaactgcggt gggagtctta tcccaatttg gtcaagagca ccg 103

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
tcctcaactc actcttcgag cg 22

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
cggtgctctt gaccaaattg g 21

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 70
caccgcagtt tcagctgctc gaattgg 27

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 71
caccgcagtt tcagctgctc gaattgg 27

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 72
caccgcagtt tcagctgctc gaattgg 27

<210> SEQ ID NO 73
<211> LENGTH: 127
<212> TYPE: DNA
<213> ORGANISM: Human adenovirus C

<400> SEQUENCE: 73
agcgcgtaat atttgtctag ggccgcgggg actttgaccg tttacgtgga gactcgccca 60
ggtgtttttc tcaggtgttt tccgcgttcc gggtcaaagt tggcgtttta ttattatagt 120
cagctga 127

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
agcgcgtaat atttgtctag ggc 23

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
tcagctgact ataataataa aacgcca 27

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 76
cggaacgcgg aaaacacctg agaaaa 26

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 77
cggaacgcgg aaaacacctg agaaaa 26

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 78
cggaacgcgg aaaacacctg agaaaa 26

<210> SEQ ID NO 79
<211> LENGTH: 182
<212> TYPE: DNA
<213> ORGANISM: Human adenovirus C

<400> SEQUENCE: 79
tcgatcttac ctgccacgag gctggctttc cacccagtga cgacgaggat gaagagggtg 60
aggagtttgt gttagattat gtggagcacc ccgggcacgg ttgcaggtct tgtcattatc 120
accggaggaa tacgggggac ccagatatta tgtgttcgct ttgctatatg aggacctgtg 180
gc 182

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
tcgatcttac ctgccacgag 20

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
gccacaggtc ctcatatagc aa 22

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 82
tgctccacat aatctaacac aaactcctca ccc 33

<210> SEQ ID NO 83
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 83
tgctccacat aatctaacac aaactcctca ccc 33

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 84
tgctccacat aatctaacac aaactcctca ccc 33

<210> SEQ ID NO 85
<211> LENGTH: 88
<212> TYPE: DNA
<213> ORGANISM: Human parainfluenza virus 2

<400> SEQUENCE: 85

```
tctcacgtat tgttctgctc ccttcacagc taggtggtct taattacctc gcatgtagca     60

gattatttaa ccgcaatatc ggagatcc                                         88


<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86

tctcacgtat tgttctgctc cc                                               22


<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

gccaatttga ctcatagtaa gcaatg                                           26


<210> SEQ ID NO 88
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88

aagacaactc cgttttcctt cattagagta cctgc                                 35


<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89

aagacaactc cgttttcctt cattagagta cctgc                                 35


<210> SEQ ID NO 90
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90

aagacaactc cgttttcctt cattagagta cctgc                                 35


<210> SEQ ID NO 91
<211> LENGTH: 103
<212> TYPE: DNA
<213> ORGANISM: Human parainfluenza virus 2

<400> SEQUENCE: 91

gaactatcgg tttcagtgca gctctagtaa ctgctactac tcttcacaat gacggattca     60

caacaataca tcctgatgtt gtttgtagtt attggcaaca cca                      103
```

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
gaactatcgg tttcagtgca gc 22

<210> SEQ ID NO 93
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
tggattatgg tctgatatct ccattg 26

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 94
tgcatcatca tacctcacag atcctgatga 30

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 95
tgcatcatca tacctcacag atcctgatga 30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 96
tgcatcatca tacctcacag atcctgatga 30

<210> SEQ ID NO 97
<211> LENGTH: 106
<212> TYPE: DNA
<213> ORGANISM: Respiratory syncytial virus

<400> SEQUENCE: 97
gaccaatcct gtcacctctg actaagggga ttttgggatt tgtattcacg ctcaccgtgc 60
ccagtgagcg aggactgcag cgtagacgct ttgtccaaaa tgccct 106

<210> SEQ ID NO 98

-continued

<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
ggaaacatac gtgaacaagc ttca 24

<210> SEQ ID NO 99
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
catcgtcttt ttctaagaca ttgtattga 29

<210> SEQ ID NO 100
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 100
tgtgtatgtg gagccttcgt gaagcaag 28

<210> SEQ ID NO 101
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 101
tgtgtatgtg gagccttcgt gaagcaag 28

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 102
tgtgtatgtg gagccttcgt gaagcaag 28

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
tgcaaacaac tctacagaca ctgttg 26

<210> SEQ ID NO 104
<211> LENGTH: 23
<212> TYPE: DNA

<213> ORGANISM: Artificial Sequence
<220> FEATURE:
<223> OTHER INFORMATION: Description of Artificial Sequence: Synthetic
primer

<400> SEQUENCE: 104
agcgtcaaaa atgggactta tga 23

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 105
aaaactctgc agcctgaatg g 21

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 106
ctttcagcta cagatgcaga caca 24

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 107
atcagaatga acagggatca ggata 25

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 108
atgcatatgt ttcagttgga tcatc 25

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 109
gccattaacg ggattacaaa caag 24

<210> SEQ ID NO 110
<211> LENGTH: 21
<212> TYPE: DNA
<213> ORGANISM: Artificial Sequence
<220> FEATURE:

<223> OTHER INFORMATION: Description of Artificial Sequence: Synthetic primer

<400> SEQUENCE: 110
atgctgagga tatgggcaat g 21

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
aatggatggg aaggaatgat agac 24

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
attccagatc aagggtgtgg aa 22

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
catcatgcgg taccaaatgg 20

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
tatcacaaat gtgataatgc atgca 25

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
gggaggaaat agacggagtc aaa 23

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
gtatgggtac caccatagca atga 24

<210> SEQ ID NO 117
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
gatctaaatg gagtgaagcc tctcat 26

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
gacaatgaat gtatggaaag tgtgaga 27

<210> SEQ ID NO 119
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
attctaatat tagccatttc ggcatt 26

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
agaggcattg cgacaaatcc 20

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
aatatcaaca atcattcacc ccaagt 26

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
gatcccaatg acacagtgac ctt 23

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 123
gtggcgatca tcccaaca 18

<210> SEQ ID NO 124
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 124
ggctacaaag atgtgatact ttggttt 27

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 125
ttgatggatg gtatggcttc ag 22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 126
taagcagcgg ctacaaagat gt 22

<210> SEQ ID NO 127
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 127
ccgtttaatt gacaagacaa atcaac 26

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 128
cgctttcaca gtccaactgc 20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 129
tcctgcacca ttcccagata 20

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 130
agcgcgtaat atttgtctag ggc 23

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 131
tcgatcttac ctgccacgag 20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 132
aggtcctcct ccctcctacg 20

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 133
cccaacacct agcctaaagc c 21

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 134
taatgatggc cgcagtgct 19

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
tgcatgatgg gaatgagagc 20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
tggtccagat ggaaaggtca 20

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
gcgttctgat tagcatagtc acact 25

<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
gcatcggcac tctccagtt 19

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
tgcaattttg ttgggtttcg 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
aagtccacca actcccgaac 20

<210> SEQ ID NO 141
<211> LENGTH: 26

<212> TYPE: DNA
<213> ORGANISM: Artificial Sequence
<220> FEATURE:
<223> OTHER INFORMATION: Description of Artificial Sequence: Synthetic
primer

<400> SEQUENCE: 141
ggaatcataa gaagaaaagt tgggaa 26

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 142
tggctaattg cattgcatcc 20

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 143
cgaaatgaca attccacggt aa 22

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 144
cctgtctcga ccaggaaacc 20

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 145
tgtcaagtaa ttgcggaagc a 21

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 146
caaggtttcc atacaatcaa gactga 26

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 147
tcaggaaact atgttgcaga acg 23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 148
caacggaatg ctgttcaata caa 23

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 149
tcgggttggc ataaatagag g 21

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 150
aatgctatca ccaatgcgaa aa 22

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 151
tgttctcttg gttgcattta acaat 25

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 152
cctagggcgc tgtgacatta 20

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
agtttgcagt gagtagaagg tcaca 25

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 154
aaagacccat tagagcacat cca 23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 155
gggtagcatg ttccattttc tga 23

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 156
ttcccattgt gactgtcctc aa 22

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 157
atccagaaaa ccatcatcaa cctt 24

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 158
tcaatgcgaa tgcgtacca 19

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 159
ccagtagaac caacaattct gcattat 27

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
gatatggcaa aggaaatcca tagg 24

<210> SEQ ID NO 161
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
tggattcttc cttctacttc agagaat 27

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
tctctggcag gcccacat 18

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
agtgagggtc ccccaataga g 21

<210> SEQ ID NO 164
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 164
atgaaaccca atagaacaac acaaatt 27

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
tagatgcaaa ttctgcactg caa 23

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
tgttcatttt gtcaatgatc gagtt 25

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 167
tatgtaagac cattccggca cat 23

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 168
atccaaaaag atagaccagc tatcatg 27

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 169
tctattccct tttcagtaag ggtgtct 27

<210> SEQ ID NO 170
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 170
tgtttttgta tgattttgtc atttgtg 27

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 171
gtcactgtgt cattgggatc aag 23

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 172
ttccccacag ttctagggtt ga 22

<210> SEQ ID NO 173
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 173
gctccactgt ttcagttgca tt 22

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 174
catgtttcca ttcttcacac acat 24

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 175
caatttatca cattgccaat ttgc 24

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 176
gcaccgcatg tttccattt 19

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
cgtagagttt gttcatttct gaatctg 27

<210> SEQ ID NO 178

-continued

<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gctgcttgtg ggtttgatga                                                  20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cctccgggac ctgtttgtaa                                                  20

<210> SEQ ID NO 180
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tcagctgact ataataataa aacgcca                                          27

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gccacaggtc ctcatatagc aa                                               22

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
cacacgggtg gtgtcgaata                                                  20

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
tttccaagac atcttccagt cg                                               22

<210> SEQ ID NO 184
<211> LENGTH: 19
<212> TYPE: DNA

<213> ORGANISM: Artificial Sequence
<220> FEATURE:
<223> OTHER INFORMATION: Description of Artificial Sequence: Synthetic
primer

<400> SEQUENCE: 184
cctctagctt gcgctgcat 19

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 185
catcccctga tcttggaagc 20

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 186
cttttgctgt tgcctctgtc a 21

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 187
gcatttgtat gcagtaacat tcca 24

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 188
caccatggga cattcaatcg 20

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 189
cctggctgtt attttccacc a 21

<210> SEQ ID NO 190
<211> LENGTH: 22
<212> TYPE: DNA
<213> ORGANISM: Artificial Sequence
<220> FEATURE:

<223> OTHER INFORMATION: Description of Artificial Sequence: Synthetic primer

<400> SEQUENCE: 190
catgcgctta gcaaatacat ga 22

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 191
tccatgcaag ttggctcatt 20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 192
ctcgtcccct tttattggca 20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
tttggcactt tcgttcatgg 20

<210> SEQ ID NO 194
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
tggtgggatt aacacgtgat gt 22

<210> SEQ ID NO 195
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
gccaatttga ctcatagtaa gcaatg 26

<210> SEQ ID NO 196
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
tggattatgg tctgatatct ccattg 26

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
agcttccaat cgggtgaaaa 20

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
tcttctagat ctgatttggc cttg 24

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
ttcctcctga taaatgaatc caca 24

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
aacgtgtagc tgtatgcttc caa 23

<210> SEQ ID NO 201
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
tgatatagct tcaatggtcc acagt 25

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
caaaacctga atcagtgcct acac 24

<210> SEQ ID NO 203
<211> LENGTH: 32
<212> TYPE: DNA
<213> ORGANISM: Artificial Sequence
<220> FEATURE:
<223> OTHER INFORMATION: Description of Artificial Sequence: Synthetic
probe

<400> SEQUENCE: 203
cactcagtga atttgctcga agacagccat aa 32

<210> SEQ ID NO 204
<211> LENGTH: 27
<212> TYPE: DNA
<213> ORGANISM: Artificial Sequence
<220> FEATURE:
<223> OTHER INFORMATION: Description of Artificial Sequence: Synthetic
probe

<400> SEQUENCE: 204
tggcgatcta ttcaactgtc gccagtt 27

<210> SEQ ID NO 205
<211> LENGTH: 27
<212> TYPE: DNA
<213> ORGANISM: Artificial Sequence
<220> FEATURE:
<223> OTHER INFORMATION: Description of Artificial Sequence: Synthetic
probe

<400> SEQUENCE: 205
tccttggcaa cccagaatgt gacttgt 27

<210> SEQ ID NO 206
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 206
cgaacaattc aaccgacact gttgacaca 29

<210> SEQ ID NO 207
<211> LENGTH: 33
<212> TYPE: DNA
<213> ORGANISM: Artificial Sequence
<220> FEATURE:
<223> OTHER INFORMATION: Description of Artificial Sequence: Synthetic
probe

<400> SEQUENCE: 207
tgccattgac gggatcacta acaaagtaaa ttc 33

<210> SEQ ID NO 208
<211> LENGTH: 36
<212> TYPE: DNA
<213> ORGANISM: Artificial Sequence
<220> FEATURE:
<223> OTHER INFORMATION: Description of Artificial Sequence: Synthetic
probe

<400> SEQUENCE: 208
cataactttt gaagccactg ggaacttaat agcacc 36

<210> SEQ ID NO 209
<211> LENGTH: 32
<212> TYPE: DNA
<213> ORGANISM: Artificial Sequence
<220> FEATURE:
<223> OTHER INFORMATION: Description of Artificial Sequence: Synthetic
probe

<400> SEQUENCE: 209
tcgagaaaat gaacactcaa ttcacagctg tg 32

<210> SEQ ID NO 210
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 210
cattaaacaa ccggttccag atcaaaggtg t 31

<210> SEQ ID NO 211
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 211
cacacaggca gccattgacc agattaatg 29

<210> SEQ ID NO 212
<211> LENGTH: 30
<212> TYPE: DNA
<213> ORGANISM: Artificial Sequence
<220> FEATURE:
<223> OTHER INFORMATION: Description of Artificial Sequence: Synthetic
probe

<400> SEQUENCE: 212
cctttgccat atcatgcttt ttgctgtgtg 30

<210> SEQ ID NO 213
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 213
ctcatcgaat tcttgatgga gcaaattgca c 31

<210> SEQ ID NO 214
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 214
tgtggatttc attcgccata tcatgcttc 29

<210> SEQ ID NO 215
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 215
tcaacagtgg cgagttccct agcactg 27

<210> SEQ ID NO 216
<211> LENGTH: 29
<212> TYPE: DNA
<213> ORGANISM: Artificial Sequence
<220> FEATURE:
<223> OTHER INFORMATION: Description of Artificial Sequence: Synthetic probe

<400> SEQUENCE: 216
tgcagacaaa gaatccactc aaaaggcaa 29

<210> SEQ ID NO 217
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 217
ctggatggct cctcggaaac cctatgt 27

<210> SEQ ID NO 218
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 218
cagtggcaag ttccctagca ctggca 26

<210> SEQ ID NO 219
<211> LENGTH: 34
<212> TYPE: DNA
<213> ORGANISM: Artificial Sequence
<220> FEATURE:
<223> OTHER INFORMATION: Description of Artificial Sequence: Synthetic probe

<400> SEQUENCE: 219
cagataaaat ctgcctagga catcatgctg tgtc 34

<210> SEQ ID NO 220
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 220
tggctcctgt caaatacaga caatgcttct ttc 33

<210> SEQ ID NO 221
<211> LENGTH: 26

<212> TYPE: DNA
<213> ORGANISM: Artificial Sequence
<220> FEATURE:
<223> OTHER INFORMATION: Description of Artificial Sequence: Synthetic
probe

<400> SEQUENCE: 221
cacggccaca agtgaatgga caatca 26

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
probe

<400> SEQUENCE: 222
catagcccct gacagggcaa gtttctttag 30

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 223
cttgggcatc atgccgtgtc aaac 24

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
probe

<400> SEQUENCE: 224
cttctggcca ttgcaatggg cc 22

<210> SEQ ID NO 225
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 225
cactcaatcg gcaattgatc aaataacagg a 31

<210> SEQ ID NO 226
<211> LENGTH: 30
<212> TYPE: DNA
<213> ORGANISM: Artificial Sequence
<220> FEATURE:
<223> OTHER INFORMATION: Description of Artificial Sequence: Synthetic
probe

<400> SEQUENCE: 226
catgtttcat acttctggcc attgcaatgg 30

<210> SEQ ID NO 227
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 227
tggccatgga gaatcaacac acaatagatc tt 32

<210> SEQ ID NO 228
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 228
cgttttcgga ttatgattcc catcgttctt c 31

<210> SEQ ID NO 229
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 229
cagctttcca gccttgaatt attcgtgtca g 31

<210> SEQ ID NO 230
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 230
cggaacgcgg aaaacacctg agaaaa 26

<210> SEQ ID NO 231
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 231
tgctccacat aatctaacac aaactcctca ccc 33

<210> SEQ ID NO 232
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 232
tgccaactca gagtaacgga tgctgtttct c 31

<210> SEQ ID NO 233
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 233
aagtcaccag actcgcgctt taggcc 26

<210> SEQ ID NO 234
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 234
ctgcatgcac tcaagctcca cggtaac 27

<210> SEQ ID NO 235
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 235
acctctgcgc acatattgtt aaagccgaaa a 31

<210> SEQ ID NO 236
<211> LENGTH: 35
<212> TYPE: DNA
<213> ORGANISM: Artificial Sequence
<220> FEATURE:
<223> OTHER INFORMATION: Description of Artificial Sequence: Synthetic probe

<400> SEQUENCE: 236
tgtcacactt acaccctaac ttatacccag gctca 35

<210> SEQ ID NO 237
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 237
ttgtccatgt agtttgtgga taagtcccat tca 33

<210> SEQ ID NO 238
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 238
agttcactcc ctcggtctac ttcaacccct t 31

<210> SEQ ID NO 239
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 239
ttaatcatgg ttcttcctgt tcttccctcc c 31

<210> SEQ ID NO 240
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 240
cacatcggtc gatgagatgg ccaagttatt a 31

<210> SEQ ID NO 241
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 241
tttggataat gtgcctgttg catgtacatg g 31

<210> SEQ ID NO 242
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 242
acatgcggga caaacagaat accagtgaat c 31

<210> SEQ ID NO 243
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 243
catctggcta ctgattgcaa caacaatgca t 31

<210> SEQ ID NO 244
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 244
agactgcaac tggtacaaca gatgtccgag a 31

<210> SEQ ID NO 245
<211> LENGTH: 35
<212> TYPE: DNA
<213> ORGANISM: Artificial Sequence
<220> FEATURE:
<223> OTHER INFORMATION: Description of Artificial Sequence: Synthetic
probe

<400> SEQUENCE: 245
aagacaactc cgttttcctt cattagagta cctgc 35

<210> SEQ ID NO 246
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 246
tgcatcatca tacctcacag atcctgatga 30

<210> SEQ ID NO 247
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 247
aacaattgaa gaccttgtcc acacatttgg g 31

<210> SEQ ID NO 248
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 248
tgagctcgat tgatatgtca attggatcaa gtg 33

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 249
cttttgtcgc aatgctatgg caaggtctac 30

<210> SEQ ID NO 250
<211> LENGTH: 36
<212> TYPE: DNA
<213> ORGANISM: Artificial Sequence
<220> FEATURE:
<223> OTHER INFORMATION: Description of Artificial Sequence: Synthetic probe

<400> SEQUENCE: 250
tgacaataaa ggagcattca aatatatcaa gccaca 36

<210> SEQ ID NO 251
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 251
acatgcacct cctttcataa aggatcatgt tg 32

-continued

<210> SEQ ID NO 252
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 252
acctgccaaa agagatcact gtggctacat c 31

<210> SEQ ID NO 253
<211> LENGTH: 12
<212> TYPE: DNA
<213> ORGANISM: Artificial Sequence
<220> FEATURE:
<223> OTHER INFORMATION: Description of Artificial Sequence: Synthetic
probe

<400> SEQUENCE: 253
atccgcgcat ag 12

<210> SEQ ID NO 254
<211> LENGTH: 12
<212> TYPE: DNA
<213> ORGANISM: Artificial Sequence
<220> FEATURE:
<223> OTHER INFORMATION: Description of Artificial Sequence: Synthetic
probe

<400> SEQUENCE: 254
atccgcgcat ag 12

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 255
caaagtggga gacgtcgttg 20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 256
caaagtggga gacgtcgttg 20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 257
caaagtggga gacgtcgttg 20

<210> SEQ ID NO 258

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 258
tcgtcgatgg tggtatgacg 20

<210> SEQ ID NO 259
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 259
ccagctcgat cactcctcgt atatcatctt ca 32

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 260
ctccgaatgc aattgtcagg 20

<210> SEQ ID NO 261
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 261
tcgtcgatgg tggtatgacg gtgaagatga tatacgagga gtgatcgagc tggattacct 60
gacaattgca ttcggag 77

<210> SEQ ID NO 262
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 262
ccagttcttc cggatacggc tggcct 26

<210> SEQ ID NO 263
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 263
aggccagccg tatccggaag aactgg 26

<210> SEQ ID NO 264

<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 264
agatttggac ctgcgagcg 19

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 265
ttctgacctg aaggctctgc gcg 23

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 266
gagcggctgt ctccacaagt 20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 267
caaagtggga gacgtcgttg 20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 268
caaagtggga gacgtcgttg 20

<210> SEQ ID NO 269
<211> LENGTH: 11
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 269
gggagacgtc g 11

<210> SEQ ID NO 270
<211> LENGTH: 20
<212> TYPE: DNA

<213> ORGANISM: Artificial Sequence
<220> FEATURE:
<223> OTHER INFORMATION: Description of Artificial Sequence: Synthetic primer

<400> SEQUENCE: 270
tcgtcgatgg tggtatgacg 20

<210> SEQ ID NO 271
<211> LENGTH: 32
<212> TYPE: DNA
<213> ORGANISM: Artificial Sequence
<220> FEATURE:
<223> OTHER INFORMATION: Description of Artificial Sequence: Synthetic probe

<400> SEQUENCE: 271
ccagctcgat cactcctcgt atatcatctt ca 32

<210> SEQ ID NO 272
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 272
ccagttcttc cggatacggc tggcct 26

<210> SEQ ID NO 273
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 273
aggccagccg tatccggaag aactgg 26

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 274
ttctgacctg aaggctctgc gcg 23

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 275
gaccratcct gtcacctctg ac 22

<210> SEQ ID NO 276
<211> LENGTH: 24
<212> TYPE: DNA
<213> ORGANISM: Artificial Sequence
<220> FEATURE:

-continued

<223> OTHER INFORMATION: Description of Artificial Sequence: Synthetic
      probe

<400> SEQUENCE: 276
cgtgcccagt gagcgaggac tgca 24

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
agggcatttt ggacaaakcg tcta 24

<210> SEQ ID NO 278
<211> LENGTH: 106
<212> TYPE: DNA
<213> ORGANISM: Influenza A virus

<400> SEQUENCE: 278
gaccaatcct gtcacctctg actaagggga ttttaggatt tgtgtttacg ctcaccgtgc 60
ccagtgagcg aggactgcag cgtagacgct ttgtccaaaa tgccct 106

<210> SEQ ID NO 279
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
ggacctccac ttactccaaa acagaaac 28

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 280
ttgacctagt tgttctcgcc a 21

<210> SEQ ID NO 281
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
gtaaggcttg catgaatgtt atttgctc 28

<210> SEQ ID NO 282
<211> LENGTH: 152
<212> TYPE: DNA
<213> ORGANISM: Influenza A virus

<400> SEQUENCE: 282
ggacctccac ttactccaaa acagaaacgg aaaatggcga gaacagctag gtcaaaagtt 60
tgaagagata agatggctga ttgaagaagt gagacacaga ctaaaaacaa ctgagaatag 120
ttttgagcaa ataacattca tgcaagcatt ac 152

<210> SEQ ID NO 283
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 283
tcctcaactc actcttcgag cg 22

<210> SEQ ID NO 284
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 284
caccgcagtt tcagctgctc gaattgg 27

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 285
cggtgctctt gaccaaattg g 21

<210> SEQ ID NO 286
<211> LENGTH: 103
<212> TYPE: DNA
<213> ORGANISM: Influenza B virus

<400> SEQUENCE: 286
tcctcaactc actcttcgag cgttttaatg aaggacattc aaagccaatt cgagcagctg 60
aaactgcggt gggagtctta tcccaatttg gtcaagagca ccg 103

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 287
gtccatcaag ctccagtttt 20

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 288
cctccgtctc cacctacttc gtt 23

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
tcttcttaca gcttgcttgc 20

<210> SEQ ID NO 290
<211> LENGTH: 145
<212> TYPE: DNA
<213> ORGANISM: Influenza B virus

<400> SEQUENCE: 290
gtccatcaag ctccagtttt gggctccaat gaccagatct ggggggaacg aagtaggtgg 60
agacggaggg tctggccaaa taagttgcag cccagtgttt gcagtagaaa gacctattgc 120
tctaagcaag caagctgtaa gaaga 145

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 291
ggaaacatac gtgaacaagc ttca 24

<210> SEQ ID NO 292
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 292
tgtgtatgtg gagccttcgt gaagcaag 28

<210> SEQ ID NO 293
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 293
catcgtcttt ttctaagaca ttgtattga 29

<210> SEQ ID NO 294
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
tcatcatctt tttctagaac attgtactga 30

<210> SEQ ID NO 295
<211> LENGTH: 106
<212> TYPE: DNA
<213> ORGANISM: Respiratory syncytial virus

<400> SEQUENCE: 295
gaccaatcct gtcacctctg actaagggga ttttgggatt tgtattcacg ctcaccgtgc 60
ccagtgagcg aggactgcag cgtagacgct ttgtccaaaa tgccct 106

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 296
atgctccttg cccactgtga atg 23

<210> SEQ ID NO 297
<211> LENGTH: 25
<212> TYPE: DNA
<213> ORGANISM: Artificial Sequence
<220> FEATURE:
<223> OTHER INFORMATION: Description of Artificial Sequence: Synthetic
probe

<400> SEQUENCE: 297
tctatacctt cactcgagta atctg 25

<210> SEQ ID NO 298
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 298
aatctttatc ccacttccta cacttg 26

<210> SEQ ID NO 299
<211> LENGTH: 181
<212> TYPE: DNA
<213> ORGANISM: Human parainfluenza virus 1

<400> SEQUENCE: 299
atgctccttg cccactgtga atgagactac agattactcg agtgaaggta tagaagattt 60
agtatttgac atattagatc tcaagggaaa gaccaaatct catcgataca aaaatgaaga 120
tataactttt gaccatcctt tttctgcaat gtatccaagt gtaggaagtg ggataaagat 180
t 181

<210> SEQ ID NO 300
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 300
accaggaaac tatgctgcag aacggc 26

<210> SEQ ID NO 301
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 301
agagctccta aacatgatgg atacc 25

<210> SEQ ID NO 302
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 302
gatccactgt gtcaccgctc aatacc 26

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 303
tcctgcacca ttcccagata 20

<210> SEQ ID NO 304
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 304
ctgacacgaa taattcaagg ctggaaagct g 31

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 305
cctccgggac ctgtttgtaa 20

<210> SEQ ID NO 306
<211> LENGTH: 102
<212> TYPE: DNA
<213> ORGANISM: Human adenovirus B

<400> SEQUENCE: 306
tcctgcacca ttcccagata attttcagct ttccagcctt gaattattcg tgtcagttct 60
tgtggtaaat ccaatccaca cattacaaac aggtcccgga gg 102

<210> SEQ ID NO 307

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 307
cgctttcaca gtccaactgc 20

<210> SEQ ID NO 308
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 308
cgttttcgga ttatgattcc catcgttctt c 31

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 309
gctgcttgtg ggtttgatga 20

<210> SEQ ID NO 310
<211> LENGTH: 129
<212> TYPE: DNA
<213> ORGANISM: Human adenovirus B

<400> SEQUENCE: 310
cgctttcaca gtccaactgc tgcggatgga ctccggagtc tggatcacgg tcatctggaa 60
gaagaacgat gggaatcata atccgaaaac ggtatcggac gattgtgtct catcaaaccc 120
acaagcagc 129

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 311
agcgcgtaat atttgtctag ggc 23

<210> SEQ ID NO 312
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 312
cggaacgcgg aaaacacctg agaaaa 26

<210> SEQ ID NO 313
<211> LENGTH: 27

<212> TYPE: DNA
<213> ORGANISM: Artificial Sequence
<220> FEATURE:
<223> OTHER INFORMATION: Description of Artificial Sequence: Synthetic
primer

<400> SEQUENCE: 313
tcagctgact ataataataa aacgcca 27

<210> SEQ ID NO 314
<211> LENGTH: 127
<212> TYPE: DNA
<213> ORGANISM: Human adenovirus C

<400> SEQUENCE: 314
agcgcgtaat atttgtctag ggccgcgggg actttgaccg tttacgtgga gactcgccca 60
ggtgtttttc tcaggtgttt tccgcgttcc gggtcaaagt tggcgtttta ttattatagt 120
cagctga 127

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 315
tcgatcttac ctgccacgag 20

<210> SEQ ID NO 316
<211> LENGTH: 33
<212> TYPE: DNA
<213> ORGANISM: Artificial Sequence
<220> FEATURE:
<223> OTHER INFORMATION: Description of Artificial Sequence: Synthetic
probe

<400> SEQUENCE: 316
tgctccacat aatctaacac aaactcctca ccc 33

<210> SEQ ID NO 317
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 317
gccacaggtc ctcatatagc aa 22

<210> SEQ ID NO 318
<211> LENGTH: 182
<212> TYPE: DNA
<213> ORGANISM: Human adenovirus C

<400> SEQUENCE: 318
tcgatcttac ctgccacgag gctggctttc cacccagtga cgacgaggat gaagagggtg 60
aggagtttgt gttagattat gtggagcacc ccgggcacgg ttgcaggtct tgtcattatc 120
accggaggaa tacgggggac ccagatatta tgtgttcgct ttgctatatg aggacctgtg 180
gc 182

```
<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319

tgcaattttg ttgggtttcg                                              20


<210> SEQ ID NO 320
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 320

ttaatcatgg ttcttcctgt tcttccctcc c                                 31


<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321

cctggctgtt attttccacc a                                            21


<210> SEQ ID NO 322
<211> LENGTH: 155
<212> TYPE: DNA
<213> ORGANISM: Human adenovirus E

<400> SEQUENCE: 322

tgcaattttg ttgggtttcg gtgacggcgg gggagggaag aacaggaaga accatgatta     60

acttttaatc caaacggtct cggagtactt caaaatgaag atcgcggaga tggcacctct    120

cgcccccgct gtgttggtgg aaaataacag ccagg                              155


<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 323

cgtgcccagt gagcgaggac tgca                                         24


<210> SEQ ID NO 324
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324

ccaaaacaga aac                                                     13


<210> SEQ ID NO 325
```

-continued

<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 325
ttgacctagt tgttctcgcc a 21

<210> SEQ ID NO 326
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 326
caccgcagtt tcagctgctc gaattgg 27

<210> SEQ ID NO 327
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
caagctccag 10

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 328
cctccgtctc cacctacttc gtt 23

<210> SEQ ID NO 329
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
acgtgaacaa gc 12

<210> SEQ ID NO 330
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 330
tgtgtatgtg gagccttcgt gaagcaag 28

<210> SEQ ID NO 331
<211> LENGTH: 25
<212> TYPE: DNA

<213> ORGANISM: Artificial Sequence
<220> FEATURE:
<223> OTHER INFORMATION: Description of Artificial Sequence: Synthetic
probe

<400> SEQUENCE: 331
tctatacctt cactcgagta atctg 25

<210> SEQ ID NO 332
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 332
accaggaaac 10

<210> SEQ ID NO 333
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 333
gcagaacggc 10

<210> SEQ ID NO 334
<211> LENGTH: 25
<212> TYPE: DNA
<213> ORGANISM: Artificial Sequence
<220> FEATURE:
<223> OTHER INFORMATION: Description of Artificial Sequence: Synthetic
probe

<400> SEQUENCE: 334
agagctccta aacatgatgg atacc 25

<210> SEQ ID NO 335
<211> LENGTH: 10
<212> TYPE: DNA
<213> ORGANISM: Artificial Sequence
<220> FEATURE:
<223> OTHER INFORMATION: Description of Artificial Sequence: Synthetic
primer

<400> SEQUENCE: 335
tcctgcacca 10

<210> SEQ ID NO 336
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 336
ctgacacgaa taattcaagg ctggaaagct g 31

<210> SEQ ID NO 337
<211> LENGTH: 11
<212> TYPE: DNA
<213> ORGANISM: Artificial Sequence
<220> FEATURE:

<223> OTHER INFORMATION: Description of Artificial Sequence: Synthetic primer

<400> SEQUENCE: 337
cacagtccaa c 11

<210> SEQ ID NO 338
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 338
cgttttcgga ttatgattcc catcgttctt c 31

<210> SEQ ID NO 339
<211> LENGTH: 10
<212> TYPE: DNA
<213> ORGANISM: Artificial Sequence
<220> FEATURE:
<223> OTHER INFORMATION: Description of Artificial Sequence: Synthetic primer

<400> SEQUENCE: 339
aatatttgtc 10

<210> SEQ ID NO 340
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 340
cggaacgcgg aaaacacctg agaaaa 26

<210> SEQ ID NO 341
<211> LENGTH: 33
<212> TYPE: DNA
<213> ORGANISM: Artificial Sequence
<220> FEATURE:
<223> OTHER INFORMATION: Description of Artificial Sequence: Synthetic probe

<400> SEQUENCE: 341
tgctccacat aatctaacac aaactcctca ccc 33

<210> SEQ ID NO 342
<211> LENGTH: 31
<212> TYPE: DNA
<213> ORGANISM: Artificial Sequence
<220> FEATURE:
<223> OTHER INFORMATION: Description of Artificial Sequence: Synthetic probe

<400> SEQUENCE: 342
ttaatcatgg ttcttcctgt tcttccctcc c 31

<210> SEQ ID NO 343
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 343
gaccratcct gtcacctctg ac 22

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 344
ctttcagcta cagatgcaga caca 24

<210> SEQ ID NO 345
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 345
gccattaacg ggattacaaa caag 24

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 346
ccctagttca agtggaggga ttc 23

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 347
acacaatctt ggagcgaaac g 21

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 348
atgctgagga tatgggcaat g 21

<210> SEQ ID NO 349
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 349
gatctaaatg gagtgaagcc tctcat 26

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 350
gggaggaaat agacggagtc aaa 23

<210> SEQ ID NO 351
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 351
gtatgggtac caccatagca atga 24

<210> SEQ ID NO 352
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 352
gacaatgaat gtatggaaag tgtgaga 27

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 353
gatcccaatg acacagtgac ctt 23

<210> SEQ ID NO 354
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 354
agggcatttt ggacaaakcg tcta 24

<210> SEQ ID NO 355
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 355
ttcccattgt gactgtcctc aa 22

<210> SEQ ID NO 356
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 356
ccagtagaac caacaattct gcattat 27

<210> SEQ ID NO 357
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 357
accgagacgg tcgacacaa 19

<210> SEQ ID NO 358
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 358
actatatagg accattcagg cactt 25

<210> SEQ ID NO 359
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 359
gatatggcaa aggaaatcca tagg 24

<210> SEQ ID NO 360
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 360
tatgtaagac cattccggca cat 23

<210> SEQ ID NO 361
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 361
tagatgcaaa ttctgcactg caa 23

<210> SEQ ID NO 362
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 362
tgttcatttt gtcaatgatc gagtt 25

<210> SEQ ID NO 363
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 363
atccaaaaag atagaccagc tatcatg 27

<210> SEQ ID NO 364
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 364
ttccccacag ttctagggtt ga 22

<210> SEQ ID NO 365
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 365
cgtgcccagt gagcgaggac tgca 24

<210> SEQ ID NO 366
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 366
cgaacaattc aaccgacact gttgacaca 29

<210> SEQ ID NO 367
<211> LENGTH: 32
<212> TYPE: DNA
<213> ORGANISM: Artificial Sequence
<220> FEATURE:
<223> OTHER INFORMATION: Description of Artificial Sequence: Synthetic
probe

<400> SEQUENCE: 367
tcgagaaaat gaacactcaa ttcacagctg tg 32

<210> SEQ ID NO 368
<211> LENGTH: 29

<212> TYPE: DNA
<213> ORGANISM: Artificial Sequence
<220> FEATURE:
<223> OTHER INFORMATION: Description of Artificial Sequence: Synthetic
probe

<400> SEQUENCE: 368
catgggtcac agtgacattc cgctctaga 29

<210> SEQ ID NO 369
<211> LENGTH: 25
<212> TYPE: DNA
<213> ORGANISM: Artificial Sequence
<220> FEATURE:
<223> OTHER INFORMATION: Description of Artificial Sequence: Synthetic
probe

<400> SEQUENCE: 369
tgcagattaa gcgggatccc tccat 25

<210> SEQ ID NO 370
<211> LENGTH: 31
<212> TYPE: DNA
<213> ORGANISM: Artificial Sequence
<220> FEATURE:
<223> OTHER INFORMATION: Description of Artificial Sequence: Synthetic
probe

<400> SEQUENCE: 370
cattaaacaa ccggttccag atcaaaggtg t 31

<210> SEQ ID NO 371
<211> LENGTH: 27
<212> TYPE: DNA
<213> ORGANISM: Artificial Sequence
<220> FEATURE:
<223> OTHER INFORMATION: Description of Artificial Sequence: Synthetic
probe

<400> SEQUENCE: 371
ctggatggct cctcggaaac cctatgt 27

<210> SEQ ID NO 372
<211> LENGTH: 27
<212> TYPE: DNA
<213> ORGANISM: Artificial Sequence
<220> FEATURE:
<223> OTHER INFORMATION: Description of Artificial Sequence: Synthetic
probe

<400> SEQUENCE: 372
tcaacagtgg cgagttccct agcactg 27

<210> SEQ ID NO 373
<211> LENGTH: 29
<212> TYPE: DNA
<213> ORGANISM: Artificial Sequence
<220> FEATURE:
<223> OTHER INFORMATION: Description of Artificial Sequence: Synthetic
probe

<400> SEQUENCE: 373
tgcagacaaa gaatccactc aaaaggcaa 29

<210> SEQ ID NO 374
<211> LENGTH: 26
<212> TYPE: DNA
<213> ORGANISM: Artificial Sequence -continued

```
<220> FEATURE:
<223> OTHER INFORMATION: Description of Artificial Sequence: Synthetic
      probe

<400> SEQUENCE: 374

cagtggcaag ttccctagca ctggca                                26


<210> SEQ ID NO 375
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 375

catagcccct gacagggcaa gtttctttag                            30
```

MULTIPLEX DETECTION OF RESPIRATORY PATHOGENS

CROSS REFERENCE TO RELATED APPLICATIONS

This application is the National Stage of International Application No. PCT/US2007/060872, published in English under PCT Article 21(2), filed Jan. 22, 2007, which claims priority to U.S. Patent Application No. 60/966,523, filed Jan. 20, 2006, both of which are incorporated by reference in their entirety.

STATEMENT REGARDING FEDERALLY SPONSORED RESEARCH OR DEVELOPMENT

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

1. Field of the Invention

The invention relates to nucleic acid based kits and methods for determining the presence or absence in a sample of respiratory pathogens including the following: influenza A (including subtyping capability for H1, H3, H5 and H7 subtypes) influenza B, parainfluenza (type 2), respiratory syncytial virus, and adenovirus.

2. Description of the Related Art

During flu season, as many as half of adult patients admitted to the emergency room are admitted with respiratory complaints. Accurate diagnosis of the patient requires analysis of clinical samples. Clinical samples are generally obtained as nasopharyngeal or throat swabs, nasal aspirate, or nasal washes, and are analyzed using viral culture, enzyme immunoassay (EIA), direct immunofluorescence antibody staining (DFA), or reverse transcriptase-polymerase chain reaction (RT-PCR).

Viral culture (the gold standard) is both sensitive and specific, but it requires 3-10 days to provide results, far too late to establish the cause of an outbreak of respiratory illness for early intervention; the method is also labor-intensive. EIA and optical immunoassay can provide rapid results (30 minutes), but the assays lack adequate sensitivity and specificity. DFA exhibits sensitivity comparable to viral culture.

DFA reagents are the mainstay of respiratory virus detection in many hospitals since reagents can detect more than one respiratory pathogen simultaneously (i.e., multiplexed) from a single sample. Multiplexed assays have been developed for detection of the most common respiratory diseases, including influenza A and B, respiratory syncytial virus (RSV), parainfluenza (Types 1-3) and adenovirus. Results can be obtained in 1-2 hours. DFA, however, requires samples with adequate numbers of target cells, high-quality equipment, a skilled microscopist, and is ultimately labor-intensive and subjective, making it less suitable for use in reference laboratories.

Many groups have demonstrated that the sensitivity and specificity of RT-PCR assays for Influenza A and B are on par with viral culture and DFA; results can be obtained in 2 hours, and large numbers of samples can be rapidly tested; however, multiplexed RT-PCR assays are not available.

A number of rapid diagnostic test kits for detection of influenza are commercially available (e.g., Becton-Dickenson Directagen Flu A, B-D Directagen Flu A+B, Binax NOW Flu Test, ZymeTx ZstatFlu). The rapid test kits generally provide results within 24 hours and are approximately 70% sensitive for detecting influenza and approximately 90% specific. The sensitivity of the rapid test kits means that as many as 30% of samples may yield false negatives, and the tests are not multiplexed.

Each of these assay techniques described above has disadvantages that make them more or less suitable for use in public health laboratories, or hospital-based laboratories, but none of these existing assays are currently employed at point-of care. They all conducted in a laboratory and usually results are not produced rapidly enough to impact on the prescribed treatment.

Accordingly, there exists a significant need for rapid and accurate multiplex tests for identification of respiratory pathogens.

Traditional approaches to DNA signature development started with the hypothesis that a particular gene was vital to the organism's virulence, host range, or other factors that might be considered "unique". Suitable primers and probe were designed for the detection system of choice, with or without computational screening (via BLAST or equivalent) for uniqueness. The resulting assay would then be tested with the available strain(s) and success declared if the targets were detected, but the assay didn't detect whatever near-neighbors were tested. This approach would sometimes yield good results, but failures occurred due to inadequate strain panel coverage and cross reactions with genetic near neighbors and complex environmental samples.

SUMMARY OF THE INVENTION

Disclosed herein is a rapid, multiplexed nucleic acid panel, e.g., a kit for the detection of influenza A (including subtyping capability for H1, H3, H5 and H7 subtypes) influenza B, parainfluenza (type 2), respiratory syncytial virus, and adenovirus wherein each pathogen is detected via the detection of at least one signature sequence. The signature sequences are presented in Table 1. The kit includes nucleic acid reagents, e.g., amplification primers and hybridization probes, for detection of the signature sequences; exemplary nucleic acid reagents are listed in Table 1. In some embodiments, the probes for detection of amplified signature sequences, e.g., the amplicons are affixed to fluorescent microbeads for analysis using a Luminex instrument.

Accordingly, one embodiment of the invention are kits for determining the presence or absence of at least one pathogen in a sample selected from the group consisting of influenza A (including subtyping capability for H1, H3, H5 and H7 subtypes) influenza B, parainfluenza (type 2), respiratory syncytial virus, and adenovirus. The kits of the invention include nucleic acid reagents for detection of at least one nucleic acid signature sequence from each of the at least one pathogens as listed in Table 1.

The kits can include reagents for detection of a single respiratory pathogen or of all the recited respiratory pathogens or any combination thereof, e.g., any two, any three, any four, any five, any six, and seven, or any eight of the recited pathogens. The kits can include reagents for the detection of an individual signature sequence or any combination of signature sequences, or all of the recited signature sequences.

In some embodiments, the kits of the invention include a set of oligonucleotides for each signature sequence to be detected, including PCR primers and/or hybridization probes for amplifications and/or detection of each signature sequence. Exemplary oligonucleotides are listed in Table 1. The kits can include at least one or all or any combination of the oligonucleotides recited in Table 1. In one embodiment, the kits include all of the oligonucleotides listed in table 1.

Additional signature sequences are disclosed in Table 9. Kits and methods using the signature sequences and, in some embodiment, the primers probes disclosed in Table 9 are also claimed.

The kits of the invention can include reagents for detection of control sequences, e.g., internal controls, negative controls, and the like. Exemplary reagents for detection of control sequences are disclosed in Table 5.

In some embodiments, the kits of the invention include hybridization probes that are affixed to microbeads, e.g., fluorescent microbeads to be analyzed using a Luminex detector.

The invention also includes methods for determining the presence or absence of at least one pathogen selected from the group consisting of influenza A (including subtyping capability for H1, H3, H5 and H7 subtypes) influenza B, parainfluenza (type 2), respiratory syncytial virus, and adenovirus in a sample using the kits described herein. In some embodiments, the methods include PCR amplification of each signature sequence.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION OF THE INVENTION

Advantages and Utility

Figure 1:
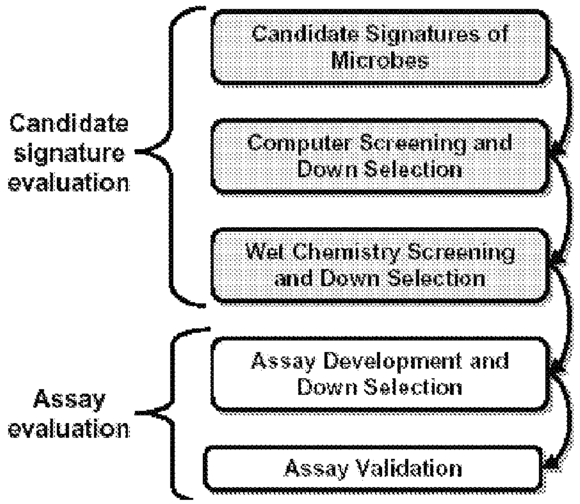
FIG. 1 illustrates the assay development scheme for identification of signature sequences and multiplexed assay development and validation.

Briefly, and as described in more detail below, disclosed and claimed herein are kits and methods for determining the presence or absence of the respiratory pathogens in a sample. The kits and methods utilize nucleic acid based methods for detection of at least one signature nucleic acid sequence corresponding to at least one respiratory pathogen of interest. In one embodiment, the presence or absence of all the respiratory pathogens is determined by detection of all disclosed signature sequences. In one embodiment, the signature sequences are amplified using exemplary primers disclosed herein, and the resulting amplicons are detected using hybridization probes (sequences disclosed herein) affixed to beads in a liquid array format; amplicons hybridized to probes affixed to beads are detected using a Luminex instrument. In a further embodiment, sample processing, amplification, and detection are performed in an automated manner using a hybrid nucleic acid analyzer, e.g., a FluIDx device.

Multiplexed detection capabilities provide many advantages over conventional detection methodologies. The use of multiplexed assay panels can provide rapid, sensitive, specific and cost-effective means of handling high volumes of samples. The assay panels can greatly improve response time and provide rapid results that can help reduce the impact of infectious disease outbreaks. The use of bead-based liquid arrays has proven to be a well adapted and versatile technology that can be custom tailored to rapidly screen for both DNA and RNA in a single tube, while also allowing for multi-loci detection.

The multiplexed assays are liquid arrays on a commercially available flow cytometer, e.g., a Luminex Bio-Plex. The liquid arrays utilize surface-functionalized polystyrene microbeads, embedded with precise ratios of red and infrared fluorescent dyes. There are 100 unique dye ratios, giving rise to 100 unique bead classes. When excited by a 635-nm laser, the two dyes emit light at different wavelengths, 658 and 712 nm and thus each bead class has a unique spectral address. Bead classes can be easily distinguished and therefore they can be combined and up to 100 different analytes can be measured simultaneously within the same sample. Although the liquid arrays have been demonstrated in a variety of applications, including detection of antigen, antibodies, small molecules, and peptides, in this application, beads are functionalized with a nucleic acid probe of approximately 30 oligonucleotides, where the probe sequence is complimentary to the desired target amplicon. Nucleic acid from the pathogen of interest is extracted, and amplified in an off-line PCR reaction. The PCR reaction is conducted using a mixture of all forward and reverse primers for each of the pathogen targets in the multiplexed panel. All forward and reverse primers are contained in the PCR reaction mixture and the amplified product is then introduced to the bead mixture (containing all probes), allowed to hybridize, and subsequently labeled with the fluorescent reporter, strepavidin-phycroerythrin. Each optically encoded and fluorescently-labeled microbead is then interrogated by the Luminex flow cytometer. A red laser excites the dye molecules inside the bead and classifies the bead to its unique bead set, and a green laser quantifies the assay at the bead surface. The flow cytometer is capable of reading several thousand beads each second; analysis can be completed in as little as 15 seconds.

The approach disclosed herein is more rapid than prior assays. Results on a clinical sample can be provided in about 4 hours, including sample preparation and processing, and data analysis.

Finally, the approach provides improved strain panel coverage and reduces cross-reactions with genetic near neighbors and complex environmental samples.

Definitions

Terms used in the claims and specification are defined as set forth below unless otherwise specified.

"Signature sequence" refers to a nucleic acid sequence specific and unique to a respiratory pathogen such that it can be used for detection of the pathogen in a sample.

"Amplicon" refers to the amplified product of a nucleic acid amplification reaction, e.g., the product of amplification of a signature sequence.

"Pathogen" means any disease-producing agent (especially a virus or bacterium or other microorganism).

"Polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

"Oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

"Percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

It must be noted that, as used in the specification and the appended claims, the singular forms "a," "an" and "the" include plural referents unless the context clearly dictates otherwise.

Kits and Methods of the Invention

Disclosed herein is a rapid, multiplexed nucleic acid panel, e.g., a kit for the detection of influenza A (including subtyping capability for H1, H3, H5 and H7 subtypes) influenza B, parainfluenza (type 2), respiratory syncytial virus, and adenovirus. The panel comprises a 21-plex assay, with assays for influenza A (including subtyping capability for H1, H3, H5 and H7 subtypes) influenza B, parainfluenza (type 2), respiratory syncytial virus, and adenovirus where each agent is represented by multiple loci. The panel includes 4 unique internal controls. Results on a patient sample can be provided in about 2 hours, including sample collection from a patient, sample preparation and processing, and data analysis. The diagnostic assay panel detects 17 signature sequences, e.g., unique nucleic acid sequences, for the detection of influenza A (including subtyping capability for H1, H3, H5 and H7 subtypes) influenza B, parainfluenza (type 2), respiratory syncytial virus, and adenovirus pathogens. The signature sequences are presented in Table 1.

TABLE 1

Signature sequences, PCR primers, and probes for detection of respiratory pathogens in a sample.

| SEQ ID NO: | Organism | Target gene | Signature identifier | Description | Sequence (5'=>3') |
|---|---|---|---|---|---|
| 1 | Influenza A | Matrix protein 1, segment 7 (gene M1) | Inf A-CDC | Signature sequence | GACCAATCCTGTCACCTCTGACTAAGGGGATTTTAGGATTTGTGTTTACGCTCACCGTGCCCAGTGAGCGAGGACTGCAGCGTAGACGCTTTGTCCAAAATGCCCT |
| 2 | Influenza A | Matrix protein 1, segment 7 (gene M1) | Inf A-CDC | Forward Primer | GACCRATCCTGTCACCTCTGAC |
| 3 | Influenza A | Matrix protein 1, segment 7 (gene M1) | Inf A-CDC | Reverse primer | AGGGCATTTTGGACAAAKCGTCTA |
| 4 | Influenza A | Matrix protein 1, segment 7 (gene M1) | Inf A-CDC | Luminex probe | CGTGCCCAGTGAGCGAGGACTGCA |
| 5 | Influenza A | Matrix protein 1, segment 7 (gene M1) | Inf A-CDC label | Luminex probe with | /5AmMC6//iSp18/TTGACCTAGTTGTTCTCGCCA |
| 6 | Influenza A | Matrix protein 1, segment 7 (gene M1) | Inf A-CDC | Taqman probe | TGC AGT CCT CGC TCA CTG GGC ACG |
| 7 | Influenza A | H1-Hemagglutin, segment 4 | H1-01 | Signature sequence | CTTTCAGCTACAGATGCAGACACAATATGTATAGGCTACCATGCGAACAATTCAACCGACACTGTTGACACAGTCCTCGAGAAGAATGTGACAGTAACACACTCTGTCAACCTATTTGAGGACAGTCACAATGGGAA |
| 8 | Influenza A | H1-Hemagglutin, segment 4 | H1-01 | Forward Primer | CTTTCAGCTACAGATGCAGACACA |
| 9 | Influenza A | H1-Hemagglutin, segment 4 | H1-01 | Reverse primer | TTCCCATTGTGACTGTCCTCAA |
| 10 | Influenza A | H1-Hemagglutin, segment | H1-01 4 | Luminex probe | CGAACAATTCAACCGACACTGTTGACACA |
| 11 | Influenza A | H1-Henagglutin, segment 4 | H1-01 | Luminex probe with label | /5AmMC6//iSp18/GGAACAATTCAACCGACACTGTTGACACA |
| 12 | Influenza A | H1-Hemagglutin, segment 4 | H1-01 | Taqman Probe | CGAACAATTCAACCGACACTGTTGACACA |
| 13 | Influenza A | H1-Henaggluitn, segment 4 | H1-41 | Signature sequence | GCCATTAACGGGATTACAAACAAGGTGAATTCTGTAATTGAGAAAATGAACACTCAATTCACAGCTGTGGGCAAAGAATTCAACAAATTGGAAAGAAGGATGGAAAACTTAAATAAAAAGGTTGATGATGGGTTTCTAGACGTTTGGACATATAATGCAGAATTGTTGGTTCTACTGG |
| 14 | Influenza A | H1-Hemagglutin, segment 4 | H1-41 | Forward Primer | GCCATTAACGGGATTACAAACAAG |
| 15 | Influenza A | H1-Hemagglutin, segment 4 | H1-41 | Reverse primer | CCAGTAGAACCAACAATTCTGCATTAT |

TABLE 1-continued

Signature sequences, PCR primers, and probes for detection of respiratory pathogens in a sample.

| SEQ ID NO: | Organism | Target gene | Signature identifier | Description | Sequence (5'=>3') |
|---|---|---|---|---|---|
| 16 | Influenza A | H1-Hemagglutin, segment 4 | H1-41 | Luminex probe | TGGAGAAAATGAACACTCAATTCACAGCTGTG |
| 17 | Influenza A | H1-Hemagglutin, segment 4 | H1-41 | Luminex probe with label | /5AmMC6//iSp18/TCGAGAAAATGAACACTCAATTCACAGCTGTG |
| 18 | Influenza A | H1-Hemagglutin, segment 4 | H1-41 | Taqman probe | TCGAGAAAATGAACACTCAATTCACAGCTGTG |
| 19 | Influenza A | H2-Hemagglutin, segment | H2-90 | Signature sequence | ACCGAGACGGTCGACACAATTCTAGAGCGGAATGTCACTGTGACCCATGCCAAGAACATCCTCGAGAAAACCCATAACGGAAAATTATGCAAACTAAATGGAATCCCTCCACTTGAACTAGGG |
| 20 | Influenza A | H2-Hemagglutin, segment | H2-90 | Forward Primer | CCCTAGTTCAAGTGGAGGGATTC |
| 21 | Influenza A | H2-Hemagglutin, segment | H2-90 | Reverse primer | ACCGAGACGGTCGACACAA |
| 22 | Influenza A | H2-Hemagglutin, segment | H2-90 | Luminex probe | CATGGGTCACAGTGACATTCCGCTCTAGA |
| 23 | Influenza A | H2-Hemagglutin, segment | H2-90 | Luminex probe with label | /5AmMC6//iSp18/CATGGGTCACAGTGACATTCCGCTCTAGA |
| 24 | Influenza A | H2-Hemagglutin, segment | H2-90 | Taqman probe | CATGGGTCACAGTGACATTCCGCTCTAGA |
| 25 | Influenza A | H2-Hemagglutin, segment 4 | H2-92 | Signature sequence | ACACAATCTTGGAGCGAAACGTCACCGTGACTCATGCCAAGGACATTCTTGAGAAAACGCATAATGGGAAGTTGTGCAGATTGAGCGGGATCCCTCCATTGGAATTGGGGGATTGCAGCATTGCGGGGTGGCTCCTTGGAAATCCGGAATGTGACCGGCTCTTAAGTGTACCTGAATGGTCCTATATAGT |
| 26 | Influenza A | H2-Hemagglutin, segment 4 | H2-92 | Forward Primer | ACACAATCTTGGAGCGAAACG |
| 27 | Influenza A | H2-Hemagglutin, segment 4 | H2-92 | Reverse primer | ACTATATAGGACCATTCAGGCACTT |
| 28 | Influenza A | H2-Hemagglutin, segment 4 | H2-92 | Luminex probe | TGCAGATTAAGCGGGATCCCTCCAT |
| 29 | Influenza A | H2-Hemagglutin, segment 4 | H2-92 | Luminex probe with label | /5AmMC6//iSp18/TGCAGATTAAGCGGGATCCCTCCAT |
| 30 | Influenza A | H2-Hemagglutin, segment 4 | H2-92 | Taqman probe | TGCAGATTAAGCGGGATCCCTCCAT |
| 31 | Influenza A | H3-Hemagglutin, segment 4 | H3-82 | Signature sequence | ACACAATCTTGGAGCGAAACGTCACCGTGACTCATGCCAAGGACATTCTTGAGAAAACGCATAATGGGAAGTTGTGCAGATTGAGCGGGATCCCTCCATTGGAATTGGGGGATTGCAGCATTGCGGGGTGGCTCCTTGGAAATCCGGAAT |

TABLE 1-continued

Signature sequences, PCR primers, and probes for detection of respiratory pathogens in a sample.

| SEQ ID NO: | Organism | Target gene | Signature identifier | Description | Sequence (5'=>3') |
|---|---|---|---|---|---|
| | | | | | GTGACCGGCTCTTAAGTGTACCTGA ATGGTCCTATATAGT |
| 32 | Influenza A | H3-Hemagglutin, segment 4 | H3-82 | Forward Primer | ATGCTGAGGATATGGGCAATG |
| 33 | Influenza A | H3-Hemagglutin, segment 4 | H3-82 | Reverse primer | GATATGGCAAAGGAAATCCATAGG |
| 34 | Influenza A | H3-Hemagglutin, segment 4 | H3-82 | Luminex probe | CATTAAACAACCGGTTCCAGATCAA AGGTGT |
| 35 | Influenza A | H3-Hemagglutin, segment 4 | H3-82 | Luminex probe with label | /5AmMc6//iSp18/CATTAAACAA CCGGTTCCAGATCAAAGGTGT |
| 36 | Influenza A | H3-Hemagglutin, segment 4 | H3-82 | Taqman probe | CATTAAACAACCGGTTCCAGATCAA AGGTGT |
| 37 | Influenza A | H5-Hemagglutin, segment 4 | H5-09 | Signature sequence | GATCTAAATGGAGTGAAACCTCTCA TTTTGAGGGATTGTAGTGTAGCTGG ATGGCTCCTCGGAAACCCTATGTGT GACGAATTCATCAATGTGCCGGAAT GGTCTTACATA |
| 38 | Influenza A | H5-Hemagglutin, segment 4 | H5-09 | Forward Primer | GATCTAAATGGAGTGAAGCCTCTCA T |
| 39 | Influenza A | H5-Hemagglutin, segment 4 | H5-09 | Reverse primer | TATGTAAGACCATTCCGGCACAT |
| 40 | Influenza A | H5-Hemagglutin, segment 4 | H5-09 | Luminex probe | CTGGATGGCTCCTCGGAAACCCTAT GT |
| 41 | Influenza A | H5-Hemagglutin, segment 4 | H5-09 | Luminex probe with label | /5AmMC6//iSp18/CTGGATGGCT CCTCGGAAACCCTATGT |
| 42 | Influenza A | H5-Hemagglutin, segment 4 | H5-09 | Taqman probe | CTGGATGGCTCCTCGGAAACCTAT GT |
| 43 | Influenza A | H5-Hemagglutin, segment 4 | H5-39 | Signature sequence | GGGAGGAAATAGACGGAGTCAAATT GGAATCAATGGGCACTTATCAGATA CTATCAATCTACTCAACAGTGGCGA GTTCCCTAGCACTGGCAATCATGGT AGCTGGTCTATCTTTTTGGATGTGC TCCAATGGATCATTGCAGTGCAGAA TTTGCATCTA |
| 44 | Influenza A | H5-Hemagglutin, segment 4 | H5-39 | Forward Primer | GGGAGGAAATAGACGGAGTCAAA |
| 45 | Influenza A | H5-Hemagglutin, segment 4 | H5-39 | Reverse primer | TAGATGCAAATTCTGCACTGCA |
| 46 | Influenza A | H5-Hemagglutin, segment 4 | H5-39 | Luminex probe | CTGGATGGCTCCTCGGAAACCCTAT GT |
| 47 | Influenza A | H5-Hemagglutin, segment 4 | H5-39 | Luminex probe with label | 5'/5AmMC6//iSp18/CTGGATGGC TCCTCGGAAACCCTATGT |

TABLE 1-continued

Signature sequences, PCR primers, and probes for detection of respiratory pathogens in a sample.

| SEQ ID NO: | Organism | Target gene | Signature identifier | Description | Sequence (5'=>3') |
|---|---|---|---|---|---|
| 48 | Influenza A | H5-Hemagglutin, segment 4 | H5-39 | Taqman probe | TCAACAGTGGCGAGTTCCCTAGCACTG |
| 49 | Influenza A | H5-Hemagglutin, segment 4 | H5-72 | Signature sequence | GTATGGGTACCACCATAGCAATGAGCAGGGGAGTGGGTACGCTGCAGACAAAGAATCCACTCAAAAGGCAATAGATGGAGTCACCAATAAGGTCAACTCGATCATTGACAAAATGAACA |
| 50 | Influenza A | H5-Hemagglutin, segment 4 | H5-72 | Forward Primer | GTATGGGTACCACCATAGCAATGA |
| 51 | Influenza A | H5-Hemagglutin, segment 4 | H5-72 | Reverse primer | TGTTCATTTTGTCAATGATCGAGTT |
| 52 | Influenza A | H5-Hemagglutin, segment 4 | H5-72 | Luminex probe | TGCAGACAAAGAATCCACTCAAAAGGCAA |
| 53 | Influenza A | H5-Hemagglutin, segment 4 | H5-72 | Luminex probe with label | 5'/5AmMC6//iSp18/TGCAGACAAAGAATCCACTCAAAAGGCAA |
| 54 | Influenza A | H5-Hemagglutin, segment 4 | H5-72 | Taqman probe | TGCAGACAAAGAATCCACTCAAAAGGCAA |
| 55 | Influenza A | H5-Hemagglutin, segment 4 | H5-91 | Signature sequence | GACAATGAATGCATGGAAAGTGTGAGAAATGGAACGTATGACTATCCACAATACTCAGAAGAATCAAGGGTAAACAGGGAGGAGATAGATGGAGTCAAATTGGAATCCGTGGGCACTTATCAGATACTATCAATCTACTCAACAGTGGCAAGTTCCCTAGCACTGGCAATCATGGTAGCTGGTCTGTCTTTTTGGAT |
| 56 | Influenza A | H5-Hemagglutin, segment 4 | H5-91 | Forward Primer | GACAATGAATGTATGGAAAGTGTGAGA |
| 57 | Influenza A | H5-Hemagglutin, segment 4 | H5-91 | Reverse primer | ATCCAAAAAGATAGACCAGCTATCATG |
| 58 | Influenza A | H5-Hemagglutin, segment 4 | H5-91 | Luminex probe | CAGTGGCAAGTTCCCTAGCACTGGCA |
| 59 | Influenza A | H5-Hemagglutin, segment 4 | H5-91 | Luminex probe with label | 5'/5AmMC6//iSp18/5Bio/CAGTGGCAAGTTCCCTAGCACTGGCA |
| 60 | Influenza A | H5-Hemagglutin, segment 4 | H5-91 | Taqman probe | CAGTGGCAAGTTCCCTAGCACTGGCA |
| 61 | Influenza A | H7-Hemagglutin, segment 4 | H7-25 | Signature sequence | GACAATGAATGCATGGAAAGTGTGAGAAATGGAACGTATGACTATCCACAATACTCAGAAGAATCAAGGCTAAACAGGGAGGAGATAGATGGAGTCAAATTGGAATCCGTGGGCACTTATCAGATACTATCAATCTACTCAACAGTGGCAAGTTCCCTAGCACTGGCAATCATGGTAGCTGGTCTGTCTTTTTGGAT |
| 62 | Influenza A | H7-Hemagglutin, segment 4 | H7-25 | Forward Primer | GATCCCAATGACACAGTGACCTT |

TABLE 1-continued

Signature sequences, PCR primers, and probes for detection of respiratory pathogens in a sample.

| SEQ ID NO: | Organism | Target gene | Signature identifier | Description | Sequence (5'=>3') |
|---|---|---|---|---|---|
| 63 | Influenza A | H7-Hemagglutin, segment 4 | H7-25 | Reverse primer | TTCCCCACAGTTCTAGGGTTGA |
| 64 | Influenza A | H7-Hemagglutin, segment 4 | H7-25 | Luminex probe | CATAGCCCCTGACAGGGCAAGTTTCTTTAG |
| 65 | Influenza A | H7-Hemagglutin, segment 4 | H7-25 | Luminex probe with label | /5AmMC6//iSp18/CATAGCCCCTGACAGGGCAAGTTTCTTTAG |
| 66 | Influenza A | H7-Hemagglutin, segment 4 | H7-25 | Taqman probe | CATAGCCCCTGACAGGGCAAGTTTCTTTAG |
| 67 | Influenza B | Nonstructural protein, segment 8 (gene NS1) | Inf B-CDC | Signature sequence | TCCTCAACTCACTCTTCGAGCGTTTTAATGAAGGACATTCAAAGCCAATTCGAGCAGCTGAAACTGCGGTGGGAGTCTTATCCCAATTTGGTCAAGAGCACCG |
| 68 | Influenza B | Nonstructural protein, segment 8 (gene NS1) | Inf B-CDC | Forward Primer | TCC TCA ACT CAC TCT TCG AGC G |
| 69 | Influenza B | Nonstructural protein, segment 8 (gene NS1) | Inf B-CDC | Reverse primer | CGG TGC TCT TGA CCA AAT TGG |
| 70 | Influenza B | Nonstructural protein, segment 8 (gene NS1) | Inf B-CDC | Luminex probe | CACCGCAGTTTCAGCTGCTCGAATTGG |
| 71 | Influenza B | Nonstructural protein, segment 8 (gene NS1) | Inf B-CDC | Luminex probe with label | /5AmMC6//iSp18/CACCGCAGTTTCAGCTGCTCGAATTGG |
| 72 | Influenza B | Nonstructural protein, segment 8 (gene NS1) | Inf B-CDC | Taqman probe | CACCGCAGTTTCAGCTGCTCGAATTGG |
| 73 | Adenovirus C | n/a intergenic region | Adeno C12 | Signature sequence | AGCGCGTAATATTTGTCTAGGGCCGCGGGGACTTTGACCGTTTACGTGGAGACTCGCCCAGGTGTTTTTCTCAGGTGTTTTCCGCGTTCCGGGTCAAAGTTGGCGTTTTATTATTATAGTCAGCTGA |
| 74 | Adenovirus C | n/a intergenic region | Adeno C12 | Forward Primer | AGCGCGTAATATTTGTCTAGGGC |
| 75 | Adenovirus C | n/a intergenic region | Adeno C12 | Reverse primer | TCAGCTGACTATAATAATAAAACGCCA |
| 76 | Adenovirus C | n/a intergenic region | Adeno C12 | Luminex probe | CGGAACGCGGAAAACACCTGAGAAAA |
| 77 | Adenovirus C | n/a intergenic region | Adeno C12 | Luminex probe with label | CGGAACGCGGAAAACACCTGAGAAAA |

TABLE 1-continued

Signature sequences, PCR primers, and probes for detection of respiratory pathogens in a sample.

| SEQ ID NO: | Organism | Target gene | Signature identifier | Description | Sequence (5'=>3') |
|---|---|---|---|---|---|
| 78 | Adenovirus C | n/a intergenic region | Adeno C12 | Taqman probe | CGGAACGCGGAAAACACCTGAGAAA A |
| 79 | Adenovirus C | 32 KD protein (gene EIA/2652980) | Adeno C14 | Signature sequence | TCGATCTTACCTGCCACGAGGCTGG CTTTCCACCCAGTGACGACGAGGAT GAAGAGGGTGAGGAGTTTGTGTTAG ATTATGTGGAGCACCCCGGGCACGG TTGCAGGTCTTGTCATTATCACCGG AGGAATACGGGGGACCCAGATATTA TGTGTTCGCTTTGCTATATGAGGAC CTGTGGC |
| 80 | Adenovirus C | 32 KD protein (gene EIA/2652980) | Adeno C14 | Forward Primer | TCGATCTTACCTGCCACGAG |
| 81 | Adenovirus C | 32 KD protein (gene EIA/2652980) | Adeno C14 | Reverse primer | GCCACAGGTCCTCATATAGCAA |
| 82 | Adenovirus C | 32 KD protein (gene EIA/2652980) | Adeno C14 | Luminex probe | TGCTCCACATAATCTAACACAAACT CCTCACCC |
| 83 | Adenovirus C | 32 KD protein (gene EIA/2652980) | Adeno C14 | Luminex probe with label | /5AmMC6//iSp18//TGCTCCACAT AATCTAACACAAACTCCTCACCC |
| 84 | Adenovirus C | 32 KD protein (gene EIA/2652980) | Adeno C14 | Taqman probe | TGCTCCACATAATCTAACACAAACT CCTCACCC |
| 85 | Parainfluenza 2 | Large protein | Para 2-88 | Signature sequence | TCTCACGTATTGTTCTGCTCCCTTC ACAGCTAGGTGGTCTTAATTACCTC GCATGTAGCAGATTATTTAACCGCA ATATCGGAGATCC |
| 86 | Parainfluenza 2 | Large protein | Para 2-88 | Forward Primer | TCTCACGTATTGTTCTGCTCCC |
| 87 | Parainfluenza 2 | Large protein | Para 2-88 | Reverse primer | GCCAATTTGACTCATAGTAAGCAAT G |
| 88 | Parainfluenza 2 | Large protein | Para 2-88 | Luminex probe | AAGACAACTCCGTTTTCCTTCATTA GAGTACCTGC |
| 89 | Parainfluenza 2 | Large protein | Para 2-88 | Luminex probe with label | /5AmMC6//iSp18/AAGACAACTC CGTTTTCCTTCATTAGAGTACCTGC |
| 90 | Parainfluenza 2 | Large protein | Para 2-88 | Taqman probe | AAGACAACTCCGTTTCCTTCATTA GAGTACCTGC |
| 91 | Parainfluenza 2 | Large protein | Para 2-91 | Signature sequence | GAACTATCGGTTTCAGTGCAGCTCT AGTAACTGCTACTACTCTTCACAAT GACGGATTCACAACAATACATCCTG ATGTTGTTTGTAGTTATTGGCAACA CCA |
| 92 | Parainfluenza 2 | Large protein | Para 2-91 | Forward Primer | GAACTATCGGTTTCAGTGCAGC |
| 93 | Parainfluenza 2 | Large protein | Para 2-91 | Reverse primer | TGGATTATGGTCTGATATCCTCATT G |

TABLE 1-continued

Signature sequences, PCR primers, and probes for detection of respiratory pathogens in a sample.

| SEQ ID NO: | Organism | Target gene | Signature identifier | Description | Sequence (5'=>3') |
|---|---|---|---|---|---|
| 94 | Parainfluenza 2 | Large protein | Para 2-91 | Luminex probe | TGCATCATCATACCTCACAGATCCT GATGA |
| 95 | Parainfluenza 2 | Large protein | Para 2-91 | Luminex probe with label | /5AmMC6//iSp18/TGCATCATCA TACCTCACAGATCCTGATGA |
| 96 | Parainfluenza 2 | Large protein | Para 2-91 | Taqman probe | TGCATCATCATACCTCACAGATCCT GATGA |
| 97 | RSV | Matrix protein (gene M) | RSV-CDC | Signature sequence | GACCAATCCTGTCACCTCTGACTAA GGGGATTTTGGGATTTGTATTCACG CTCACCGTGCCCAGTGAGCGAGGAC TGCAGCGTAGACGCTTTGTCCAAAA TGCCCT |
| 98 | RSV | Matrix protein (gene M) | RSV-CDC | Forward Primer | GGAAACATACGTGAACAAGCTTCA |
| 99 | RSV | Matrix protein (gene M) | RSV-CDC | Reverse primer | CAT CGT CTT TTT CTA AGA CAT TGT ATT GA |
| 100 | RSV | Matrix protein (gene M) | RSV-CDC | Luminex probe | TGT GTA TGT GGA GCC TTC GTG AAG CAA G |
| 101 | RSV | Matrix protein (gene M) | RSV-CDC | Luminex probe with label | /5AmMC6//iSp18/TGT GTA TGT GGA GCC TTC GTG AAG CAA G |
| 102 | RSV | Matrix protein (gene M) | RSV-CDC | Taqman probe | TGT GTA TGT GGA GCC TTC GTG AAG CAA G |

Additional signature sequences and exemplary primer/probe sets are disclosed in Table 9.

Accordingly one aspect of the invention is a kit for determining the presence or absence in a sample of at least one pathogen selected from the group consisting of influenza A (including subtyping capability for H1, H3, H5 and H7 subtypes) influenza B, parainfluenza (type 2), respiratory syncytial virus, and adenovirus said kit having nucleic acid reagents for detection of at least one nucleic acid signature sequence from each pathogen. The signature sequences are presented in Table 1.

In one aspect, the kit includes reagents for determining the presence or absence of all respiratory pathogens, e.g., influenza A (including subtyping capability for H1, H3, H5 and H7 subtypes) influenza B, parainfluenza (type 2), respiratory syncytial virus, and adenovirus in a sample. The kit includes nucleic acid reagents for detection of all signature sequences listed in Table 1.

In another aspect, the kits includes reagents for detection of less than all eight pathogens, e.g., for detection of at least 1, 2, 3, 4, 5, 6, or at least 7 of the pathogens.

In some embodiments, the kits include nucleic acid reagents that are sets of oligonucleotides for each signature sequence to be detected. Each set includes PCR primers and hybridization probes for each signature sequence. Exemplary embodiments include the PCR primers and hybridization probes disclosed in Table 1. In one embodiment the kit includes each of the PCR primers and hybridization probes listed for the respective pathogen, e.g., the kit includes all 17 sets. In other embodiments, the kit includes a subset of the disclosed primer and probes, e.g., at least 1, 2, 3, 4, 5, 6, 7, 8, 9, 10, 11, 12 13, 14, 15, or at least 16, of the primer/probe sets disclosed in Table 1.

In one aspect the kits include control nucleic acid reagents. Exemplary control nucleic acid reagents are disclosed in Table 5.

In one variation of the invention, the kit includes hybridization probes that are affixed to a solid substrate, e.g., a microsphere.

Also disclosed are methods using the kits disclosed herein. In some embodiments, the method includes a PCR based amplification step.

Accordingly, in a preferred embodiment the invention provides the use of all PCR primers in Table 1. Alternatively, the invention provides the use of all PCR primers for a particular pathogen. In yet another embodiment the invention provides the use of all of the probes in Table 1. Alternatively, the invention provides the use of all probes in Table 1.

Samples

The invention provides kits and methods for detection of respiratory pathogens in a sample. As will be appreciated by those in the art, the sample may comprise any number of things, including, but not limited to, include nasal and/or throat washes, nasal and or throat swabs, or nasal aspirates obtained from human patients; research samples; purified samples, such as purified genomic DNA, RNA, proteins, etc.;

and raw samples (bacteria, virus, genomic DNA, etc.). As will be appreciated by those in the art, any experimental manipulation can have been performed on the sample before analysis.

In one embodiment, the sample type for diagnosis of respiratory diseases is a human nasal or throat swab.

If required, nucleic acid from the sample is isolated using known techniques. For example, the sample may be treated to lyse the cells, using known lysis buffers, sonication, electroporation, etc., with purification occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents that may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Signature Sequences

Using the kits and methods of the invention, the presence or absence of a respiratory pathogen in a sample is determined using reagents for detection of a signature nucleic acid sequence. The term "signature sequence" or "signature nucleic acid" or grammatical equivalents herein means a nucleic acid sequence on a single strand of nucleic acid or its complement. The signature sequence can be a portion of a gene, a regulatory sequence, genomic DNA, cDNA, RNA including mRNA and rRNA, and the like.

In one embodiment, the signature sequences detected using the kits and methods of the inventions are disclosed in Table 1. In other embodiments, the signature sequences detected are disclosed in Table 9. In further embodiments, the signature sequences detected are those defined by the primer/probe sets disclosed in Tables 4 and 10.

As will be appreciated by those in the art, the signature sequence can take many forms in the target nucleic acid in the sample. For example, it may be contained within a larger nucleic acid sequence, i.e. all or part of a gene or mRNA, a restriction fragment of a plasmid or genomic DNA, among others.

Amplification Methods

In one embodiment and as describe more fully herein, a signature sequence from a sample is amplified to produce a secondary target, e.g. an amplicon that is detected, as outlined herein.

Amplification involves the amplification (replication) of the signature sequence to be detected, such that the number of copies of the signature sequence is increased. Suitable amplification techniques include, but are not limited to, the polymerase chain reaction (PCR), strand displacement amplification (SDA), transcription mediated amplification (TMA) and nucleic acid sequence based amplification (NASBA).

In one embodiment, the amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others.

In another embodiment, the amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In another embodiment, the amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In another embodiment, the amplification technique is signal amplification. Signal amplification involves the use of limited number of target molecules as templates to either generate multiple signaling probes or allow the use of multiple signaling probes. Signal amplification strategies include LCR, CPT, QβR, invasive cleavage technology, and the use of amplification probes in sandwich assays.

In another embodiment, single base extension (SBE; sometimes referred to as "minisequencing") is used for amplification. Briefly, SBE is a technique that utilizes an extension primer that hybridizes to the target nucleic acid. A polymerase (generally a DNA polymerase) is used to extend the 3' end of the primer with a nucleotide analog labeled a detection label as described herein. Based on the fidelity of the enzyme, a nucleotide is only incorporated into the extension primer if it is complementary to the adjacent base in the target strand. Generally, the nucleotide is derivatized such that no further extensions can occur, so only a single nucleotide is added. However, for amplification reactions, this may not be necessary. Once the labeled nucleotide is added, detection of the label proceeds as outlined herein. See generally Sylvanen et al., Genomics 8:684-692 (1990); U.S. Pat. Nos. 5,846,710 and 5,888,819; Pastinen et al., Genomics Res. 7(6):606-614 (1997); all of which are expressly incorporated herein by reference.

In another embodiment, the signal amplification technique is OLA (oligonucleotide ligation amplification). OLA, which is referred to as the ligation chain reaction (LCR) when two-stranded substrates are used, involves the ligation of two smaller probes into a single long probe, using the target sequence as the template. In LCR, the ligated probe product becomes the predominant template as the reaction progresses. The method can be run in two different ways; in a first embodiment, only one strand of a target sequence is used as a template for ligation; alternatively, both strands may be used. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; WO 97/31256; and WO 89/09835, and U.S. Ser. Nos. 60/078,102 and 60/073,011, all of which are incorporated by reference.

In another embodiment the signal amplification technique is RCA. Rolling-circle amplification is generally described in Baner et al. (1998) Nuc. Acids Res. 26:5073-5078; Barany, F. (1991) Proc. Natl. Acad. Sci. USA 88:189-193; and Lizardi et al. (1998) Nat. Genet. 19:225-232, all of which are incorporated by reference in their entirety.

A second alternative approach involves OLA followed by RCA. In this embodiment, an immobilized primer is contacted with a target nucleic acid. Complementary sequences will hybridize with each other resulting in an immobilized duplex. A second primer is contacted with the target nucleic acid. The second primer hybridizes to the target nucleic acid adjacent to the first primer. An OLA assay is performed as described above. Ligation only occurs if the primers are complementary to the target nucleic acid. When a mismatch occurs, particularly at one of the nucleotides to be ligated, ligation will not occur. Following ligation of the oligonucleotides, the ligated, immobilized, oligonucleotide is then hybridized with an RCA probe. This is a circular probe that is designed to specifically hybridize with the ligated oligonucleotide and will only hybridize with an oligonucleotide that has undergone ligation. RCA is then performed as is outlined in more detail below.

Nucleic Acid Reagents: Primers and Probes

The kits and method disclosed herein use nucleic acid reagents, e.g., oligonucleotides, e.g., amplification primers and hybridization probes, for detection of the signature sequences. Exemplary primers and hybridization probes are disclosed herein, e.g., in Table 1, and in one embodiment, the claimed kits and methods include the primers and probes disclosed in Table 1. The invention also include kits and methods using variant versions of the primers and probes disclosed herein, e.g., oligonucleotides that are shorter or longer or have at least 95%, 96%, 97%, 98%, or at least 99% sequence identity, as long as the oligonucleotide accomplishes that same function, e.g., functions in the assay for the detection of the signature sequences.

Additional primers and probes of the invention are described in Tables 4, 9, and 10.

In addition, one of skill can readily design additional primers and hybridization probes that can function as nucleic acid reagents for the detection of signature sequences. Generally the nucleic acid reagents include signature sequence, or complementary sequence, sufficient to confer specific amplification or hybridization to the target nucleic acid, e.g., respiratory pathogen nucleic acid.

The length of a nucleic acid reagent, e.g., a primer or hybridization probe, will vary depending on the application. In general, the total length can be from about 8 to 80 nucleobases in length. The primers and hybridization probes used in accordance with this invention preferably comprise from about 8 to about 80 nucleobases (i.e. from about 8 to about 80 linked nucleosides). One of ordinary skill in the art will appreciate that the invention embodies oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

Nucleic Acid Reagents: Adapters

In a preferred embodiment, a hybridization probe further comprises an adapter sequence. Adapters facilitate immobilization of probes to solid supports. That is, arrays (either solid phase or liquid phase arrays) are generated that contain capture probes that are not target specific, but rather specific to individual (preferably) artificial adapter sequences. The adapter sequences of the probes are preferably from 15-25 nucleotides in length, with 20 being especially preferred. The target specific portion of the probe is preferably from 15-50 nucleotides in length.

Thus, an adapter sequence is a nucleic acid that is generally not identical to or complementary to the signature sequence, i.e. is exogenous, but is added or attached to a hybridization probe. It should be noted that in this context, the signature sequence can include the primary signature sequence, or can be a derivative target such as a reactant or product of the reactions outlined herein; thus for example, the target sequence can be a PCR product, a first ligation probe or a ligated probe in an OLA reaction, etc.

The terms "barcodes", "adapters", "addresses", "tags" and "zip codes" have all been used to describe artificial sequences that are added to amplicons to allow separation of nucleic acid fragment pools. One preferred form of adapters is hybridization adapters. In this embodiment adapters are chosen so as to allow hybridization to the complementary capture probes on a surface of an array. In general, sets of adapters and the corresponding capture probes on arrays are developed to minimize cross-hybridization with both each other and other components of the reaction mixtures, including the signature sequences and sequences on the larger nucleic acid sequences outside of the target sequences (e.g. to sequences within genomic nucleic acid of the respiratory pathogen).

As will be appreciated by those in the art, the attachment, or joining, of the adapter sequence to the target sequence can be done in a variety of ways. In a preferred embodiment, the adapter sequences are added to the primers of the reaction (extension primers, amplification primers, readout probes, genotyping primers, Rolling Circle primers, etc.) during the chemical synthesis of the primers. The adapter then gets added to the reaction product during the reaction; for example, the primer gets extended using a polymerase to form the new target sequence that now contains an adapter sequence. Alternatively, the adapter sequences can be added enzymatically. Furthermore, the adapter can be attached to the target after synthesis; this post-synthesis attachment can be either covalent or non-covalent. In a preferred embodiment the adapter is added to the target sequence or associated with a particular allele during an enzymatic step.

In addition, as will be appreciated by those in the art, the adapter can be attached either on the 3' or 5' ends, or in an internal position, depending on the configuration of the system.

In one embodiment the use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The adapter sequences can then be incorporated in the target probes.

As will be appreciated by those in the art, the length of the adapter sequences will vary, depending on the desired "strength" of binding and the number of different adapters desired. In a preferred embodiment, adapter sequences range from about 5 to about 25 basepairs in length, with 20 being especially preferred.

In a preferred embodiment, the adapter sequence uniquely positions the target analyte, e.g. agricultural organism nucleic acid, to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target analyte.

Detection of Signature Sequences

As described herein, the kits and method described herein can utilize detection of the signature sequences by detection of amplicons. In general, either direct or indirect detection of amplicon can be performed. Direct detection generally involves the incorporation of a label into the amplicon via, e.g., a labeled primer. Indirect detection involves incorporation of a label into, e.g., a hybridization probe.

For direct detection, the label(s) may be incorporated in four ways: (1) the primers comprise the label(s), for example attached to the base, a ribose, a phosphate, or to analogous structures in a nucleic acid analog; (2) modified nucleosides that are modified at either the base or the ribose (or to analogous structures in a nucleic acid analog) with the label(s); these label-modified nucleosides are then converted to the triphosphate form and are incorporated into the newly synthesized strand by a polymerase; (3) modified nucleotides are used that comprise a functional group that can be used to add a detectable label; or (4) modified primers are used that comprise a functional group that can be used to add a detectable label. Any of these methods result in a newly synthesized strand that comprises labels that can be directly detected as outlined below.

For indirect detection, the label is incorporated into the hybridization probe using methods well known to one of skill in the art. For example, the label can be incorporated by attaching the label to a base, ribose, phosphate, or to analogous structures in a nucleic acid analog, or by synthesizing the hybridization probe using a modified nucleoside.

Thus, a modified strands of the amplicon or the hybridization probe can include a detection label. By "detection label" or "detectable label" herein is meant a moiety that allows detection. This may be a primary label or a secondary label.

In one embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, alexa dyes, phycoerythin, bodipy, and others described in the 6th Edition of the Molecular Probes Handbook by Richard P. Haugland, hereby expressly incorporated by reference.

In another embodiment, a secondary detectable label is used. Accordingly, detection labels may be primary labels (i.e. directly detectable) or secondary labels (indirectly detectable). A secondary label is one that is indirectly detected; for example, a secondary label can bind or react with a primary label for detection, or may allow the separation of the compound comprising the secondary label from unlabeled materials, etc. Secondary labels find particular use in systems requiring separation of labeled and unlabeled probes, such as SBE reactions. Secondary labels include, but are not limited to, one of a binding partner pair; chemically modifiable moieties; nuclease inhibitors, etc.

In another embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smallest of the pair is attached to the NTP for incorporation into the extension primer.

In another embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In another embodiment, the binding partner pair comprises a primary detection label (for example, attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

Formats

The kits described herein can be used in any number of formats well-known to one of skill in the art. Examples include e.g., PCR and detection via gel electrophoresis; TaqMan PCR; PCR and hybridization to probes affixed to a solid support and detection using a Luminex instrument; and automated formats including a hybrid nucleic acid analyzer such as a FluIDx described in patent application US PGPUB 2005/0239192.

Detection of the amplified products described above preferably employs arrays, as described herein. In one embodiment, the arrays comprise hybridization probes affixed to a solid support.

By "substrate" or "solid support" or other grammatical equivalents herein is meant any material to which a hybridization probe can be immobilized. Possible substrates include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, and a variety of other polymers. In general, the substrates allow optical detection and do not themselves appreciably fluoresce.

In some embodiments the substrate is flat (planar), although as will be appreciated by those in the art, other configurations of substrates may be used as well.

In a preferred embodiment the array is a liquid array. In this embodiment, a species of hybridization probes is immobilized to a first set of microspheres. Likewise, a second species of hybridization probes is immobilized to a second set of microspheres. Similarly additional species of hybridization probes are attached to discrete populations of microspheres. There is no upward limit to the number of populations of microspheres or capture probes when populations are analyzed individually.

When multiple sets of microspheres are mixed and analyzed the number of sets is limited only by the number of encoding moieties applied to the microspheres. That is, microspheres are encoded so that the identity of each set of microspheres can be determined. Encoding moieties can be any distinguishable characteristic, e.g. size, shape, texture etc., of the microsphere. In preferred embodiments, encoding moieties are attributes that are not inherent in the bead or microsphere itself. Rather, the encoding moiety is a feature that is added to a bead. Preferred encoding moieties include, but are not limited to nucleic acids, proteins, and detectable labels or fluors. In addition, materials such as nanocrystals can be used as encoding moieties.

Also, in some embodiments, a plurality of different types of encoding moieties can be used to develop numerous different codes.

In a preferred embodiment, the beads and encoding system are those used in the Luminex flow cytometer. This system is described in more detail in U.S. Pat. No. 5,981,180, which is expressly incorporated herein by reference.

Briefly, the flow cytometer comprises a Luminex LX100 Flow Cytometer instrument with a sheath source and a waste reservoir. The hybridized bead array is introduced into the Luminex Flow Cytometer instrument where the beads are interrogated by two lasers, a red laser for the internal discriminator and a green laser for the external discriminator dyes respectively.

With the liquid arrays it is possible to simultaneously multiplex 100 or more different organisms or targets. The discrimination of the polystyrene Luminex bead array is dependent on the precise ratio of two internal discriminator dyes, a red and an infrared dye. The signal intensity on the surface of the bead is dependent on the concentration of the analyte in solution, in our case the amplified DNA of a suspect agent or an antigen or a toxin, whichever the case may be.

A 100-plex Luminex liquid array is generated by intercalating varying ratios of red and orange infrared dyes into polystyrene latex microspheres or beads. The process of producing varying ratios of red and orange infrared dyes in the beads is accomplished by increasing the amount of red dye and increasing the amount of orange dye. This gives each optically encoded bead a unique spectral address.

The beads are coated with capture probes complementary to adapter sequences, e.g., hybridization probes, as described herein. Each bead has an attachment site specific for a unique bioagent, e.g., hybridization probe.

The beads are analyzed in the flow cytometer, one at a time. A red laser classifies the bead, identifying the bead type. Subsequently a green laser quantifies the assay on the bead surface—only those beads with a complete sandwich will fluoresce in the green, and the signal is a function of label concentration, which is indicative of the amount of target, e.g., amplicon.

In another embodiment, the kits and methods of the invention are used with a hybrid nucleic acid analyzer, e.g., an integrated system that includes an in-line thermal cycler and flow cytometer. Other components of the system are set forth in US PGPUB 2005/0239192, which is expressly incorporated herein by reference.

Briefly, a hybrid nucleic acid analyzer system includes a reagent delivery system, a thermal cycler, optionally a bead trap for washing, and a flow cytometer. The system can include a hybridization chamber or, alternatively following amplification the microspheres are brought into the thermal cycler for hybridization with the amplicons.

The reagent delivery system delivers PCR reagents to the thermal cycler autonomously. On completion of cycling in the thermal cycler, beads or microspheres are added to the sample in the thermal cycler. The hybridized beads are then moved to the flow cytometer for analyses. Alternatively, the hybridized beads are added to the bead trap where they undergo washing prior to being moved to the flow cytometer.

In some embodiments, the kits and methods of the instant invention are used with a hybrid nucleic acid analyzer system that utilizes nucleic acid amplification and detection and sample preparation and analysis techniques and information described in currently co-pending U.S. patent application Ser. Nos. 10/189,319 and 10/643,797, both of which are owed by the Regents of the University of California, the assignee of this application. U.S. patent application Ser. No. 10/189,319 for an "Automated Nucleic Acid Assay System" was filed Jul. 2, 2002 by Billy W. Colston, Jr., Steve B. Brown, Shanavaz L. Nasarabadi, Phillip Belgrader, Fred Milanovich, Graham Marshall, Don Olson, and Duane Wolcott and was published as U.S. patent application No. 2003/0032172 on Feb. 13, 2003. U.S. patent application Ser. No. 10/643,797 for a "System for Autonomous Monitoring of Bioagents" was filed Aug. 19, 2003 by Richard G. Langlois, Fred Milanovich, Billy W. Colston, Jr., Steve B. Brown, Don A. Masquelier, Ray P. Mariella, and Kodomundi Venkateswaran and was published as U.S. patent application No. 2004/0038385 on Feb. 26, 2004. The disclosures of U.S. patent application Ser. Nos. 10/189,319 and 10/643,797 are incorporated herein by this reference.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992); "Oligonucleotide Synthesis" (M. J. Gait, ed., 1984); "Animal Cell Culture" (R. I. Freshney, ed., 1987); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Summary of Assay Development

The Bioassays and Signatures Program (BSP) at Lawrence Livermore National Laboratory (LLNL) have constructed a robust technical architecture for the rapid development of highest-quality nucleic acid assays, tailored to end-user specifications. A summary of this process is shown in FIG. 1.

The pipeline process begins with an analysis of all available genomic sequence information, which forms the basis for the development of signatures. A signature is a region or set of regions on a chromosome that is unique to that organism. Candidate signatures can be selected based on performance criteria for specific detection technologies. Our nucleic acid assays employ PCR with primer pairs to generate the signature fragment(s) of interest. Once candidate signatures have been identified, they are subjected to a computational screening and down-selection process. This "in silico" screening method tests the candidate regions for uniqueness when compared to all the sequence data available. The computational screening also ensures that the signature primer pairs are amenable to assay chemistry requirements and provides rapid, low-cost initial screening of signatures.

The primers that emerge from the computational screening and down-selection are then tested against an extensive panel of DNAs and cDNAs. The bench screening consists of a panel of 2,000 to 3,000 samples, representing a wide range of organisms and backgrounds. This bench screening ensures that the primers will detect the strain diversity of the pathogen but will not react with the nucleic acids of other organisms that could be present in a sample.

Primer pairs that successfully pass the wet chemistry screening criteria are advanced to the assay development stage. Assay development includes the optimization of detection protocols, so that the assays perform consistently to required specifications on the prototype equipment selected. At the assay development stage, assays are fully characterized by assessing performance against a specified, standardized panel of targets (nucleic acid from various strains of the organism of interest, for which the assay was designed) and near-neighbors (genetically-related organisms), which yields rich data about the sensitivity and specificity of an assay. The results of all this work (from informatics through characterization) is captured in an extensive "certificate of analysis" that provides an assay pedigree. The pedigree comprises the entire history of the assay, including results of screening, metrics of performance such as sensitivity, specificity, and known cross-reactions (if any); all available at a glance, captured in a single data file.

Example 1

In-Silico Identification of Candidate Signature Sequences

The LLNL Bioinformatics team developed "KPATH", a whole-genome comparative analysis software system. The general approach is the following: All available complete genomes of different strains of the target species are compared using multiple genome alignment programs. A consensus gestalt is formed from the alignments that contain the sequence conserved among all target inputs. This step is bypassed if only one target sequence is available. To establish that the organism-conserved sequence does not occur in any other sequenced microbial organism, the consensus gestalt is compared against the LLNL updated database of microbial organisms. A customized algorithm accomplishes this electronic subtraction, and the result is a uniqueness gestalt that is mined for potential signature candidates. A final computational screening is done to verify that cross-reactions are not detected.

KPATH allows the genome to define potential signature candidates. However, rather than selecting candidate signatures randomly (often there are more candidates than is economically feasible to screen in the wet lab), they can be prioritized based on annotation. Annotation allows signatures to be scrutinized in a biological context. Identifying genes responsible for rendering a pathogen virulent is one component of a good diagnostic signature set. We manually select candidates associated with genes of interest, and include a random selection of candidates within intergenic regions, for wet lab screening. The random unique intergenic regions are selected as a guard against gene deletion or substitution engineering to evade DNA-based detection. We note that there are few tools focused on viral gene finding, and none known to us that can adequately predict genes in certain RNA virus families.

Because signature candidates are generated using exact matches in the Vmatch step described above, additional electronic screening on the signature candidates is performed to catch potential non-exact matches that might result in false positives in the wet lab. We have seen cases where this would predict cross-reactions with near-neighbor species that had not been caught by the exact-matching step (due to as few as 1 or 2 fortuitously-placed mis-matched bases.)

We generated a large number of candidate signatures from our bioinformatics survey, including 35 signatures for influenza; 119 for parainfluenza; 551 for adenovirus, 100 for respiratory syncytial virus, and 53 for SARS.

Although KPATH was successfully used to identify and select candidate signatures for all the pathogens included in our respiratory panel, it was unable to identify nucleic acid signatures (in Taqman format) for the HA gene, which is the basis of H subtyping for Influenza A. The main reason is that the HA gene is highly divergent, and therefore no single Taqman signature can be generated to capture all members of a subtype. In contrast, broad screening signatures designed to detect any and all strain(s) of a pathogen (i.e., "pan") target highly conserved genes, such as a matrix protein (MP) gene for influenza A, and non-structural proteins (NSP) gene for influenza B.

To develop signatures for influenza A subtype, we employed Minimal Set Clustering, a software tool developed at LLNL to identify the minimal set of signatures required to recognize all "members" of a target set (all target sequences identified in Genbank). Minimal Set Clustering software is similar to the KPATH system, however, based on slightly different algorithms and parameters. It is used when the diversity of the genome targets of interest is too great to be represented by a single Taqman signature. This software calculates the minimal number of signatures required to detect all genomes in a given target set, and in doing so, generates sets of Taqman signatures that, when used in combination, are predicted be able to detect all the genome target sequences. Like KPATH, the Minimal Set Clustering system ensures that the signatures are not predicted to cross-react with any sequenced non-target organism. In addition, the clustering method allows mismatches with limited changes to Tm values so as not to significantly affect the process of hybridization.

For the design of H5 subtype signatures we used the 217 H5 Genbank sequences available as our target set and determined that a minimum set of 4 signatures was needed to capture all 217 sequenced isolates. The H5 sub-groups appear to cluster by lineage, where the first and fourth signature detect groups of North American sequences and the 2nd and 3rd detect Eurasian sequences, so these signatures may accomplish the lineage discrimination. The software allowed mismatches against targets to the extent that Tm values would still allow Taqman reaction.

A summary of the results of our analysis for each of the HA influenza subtypes is presented in Table 2.

TABLE 2

Number of signatures theoretically required for the detection of all relevant sequences for each Influenza A subtype.

| Flu A subtype | Number of signatures needed to provide complete coverage |
|---|---|
| Flu A - H1 | 7 |
| Flu A - H2 | 11 |
| Flu A - H3 | 5 |
| Flu A - H5 | 4 |
| Flu A - H7 | 9 |

Example 2

Use of Taqsim to Further Screen Candidate Signature Sequences

A computational TaqMan simulator program, "Taqsim", was used to identify all potential targets for each candidate signature from all sequences available in Genbank. Taqsim is a BLAST-based comparison of each signature as a triplet against all sequences in Genbank to identify the targets that are predicted to produce a TaqMan reaction at 57 degrees primer annealing and 67 degrees for probe annealing (these temperatures are according to Primer 3 oligo Tm calculations). Input parameters allow for standardized signature informatics that allows for universal protocol development and assay compatibility.

TABLE 3

Taqsim settings used for generation of candidate signatures Primer3 Parameters

| Parameters | Standard Settings |
|---|---|
| PRIMER_OPT_SIZE | 20 |
| PRIMER_MIN_SIZE | 18 |
| PRIMER_MAX_SIZE | 27 |
| PRIMER_PRODUCT_OPT_SIZE | 100 |
| PRIMER_PRODUCT_SIZE_RANGE | 71-600 |
| PRIMER_OPT_TM | 62 |
| PRIMER_MIN_TM | 61 |
| PRIMER_MAX_TM | 63 |
| PRIMER_MIN_GC | 20 |
| PRIMER_MAX_GC | 80 |
| PRIMER_PICK_INTERNAL_OLIGO | 1 |
| PRIMER_INTERNAL_OLIGO_OPT_SIZE | 31 |
| PRIMER_INTERNAL_OLIGO_MIN_SIZE | 18 |
| PRIMER_INTERNAL_OLIGO_MAX_SIZE | 36 |
| PRIMER_INTERNAL_OLIGO_OPT_TM | 72 |
| PRIMER_INTERNAL_OLIGO_MIN_TM | 71 |
| PRIMER_INTERNAL_OLIGO_MAX_TM | 73 |
| Number of Primers/Probe Set generated: | 101 |

Example 3

Wet Chemistry Screening Process

To ensure extremely high selectivity and sensitivity, a rigorous wet-chemistry screening was performed to further down-select candidate nucleic acid signatures before taking those signatures that pass this screening on to assay development. This step ensures that the primers will detect the strain diversity of the pathogen, but will not react with the nucleic acids of other organisms that could be present in a sample. At this stage, only the primers are tested and many unsuitable primers (e.g., those that form primer-dimers, those that do not produce amplicons of the correct size, etc.) can be eliminated in this first step.

An initial screening of the PCR signatures was performed in duplicate using end-point PCR and gel electrophoresis as described herein. The signatures are initially screened against nucleic acid extractions from 5 soils, 5 eukaryotic nucleic acids, and 5 microbes, each picked at random, and selected near neighbors. The soils represent a diverse geographical and temporal distribution and contain complex mixtures of organisms. The eukaryotic nucleic acids are those that may potentially carry over from sample collection processes. The microbial nucleic acids were selected to span the range of microbial diversity. Near neighbors are organisms that are closely related at the genetic level and have the greatest likelihood of causing confounding results in the assays.

Signatures that produce amplicons with various soils, microbe, eukaryotic or near neighbor nucleic acids were eliminated. Furthermore, signatures were eliminated due to their inability to produce correct size PCR product when crossed with targets. The down-selected signatures are then put through intensive background screening in real-time (TaqMan) PCR format.

Reagents: Invitrogen Platinum Taq polymerase, Catalog #10966-083 (Carlsbad, Calif.); Invitrogen 10 PCR Buffer, Catalog #10966-083 (Carlsbad, Calif.); Invitrogen 50 mM MgCl2, Catalogue # 10966-083 (Carlsbad, Calif.); Sigma Chemical BSA, Catalogue #B8687 (St Louis, Mo.); Amersham dNTPs, Catalogue #27-2035-02 (Piscataway, N.J.); Biosearch Technologies oligonucleotides (Novato, Calif.); Nuclease-Free water; Cambrex 4% agarose gel, Catalogue #57225; Cambrex Simplyload 20 bp ladder, catalogue #50331; Teknova 10×TBE, Catalogue # T0210; Teknova 10× Loading Dye, Catalogue # F3062; Clonetech Powerscript one step qRT-PCR kit, Catalogue #630051.

Sample preparation. Pathogen nucleic acids were isolated from virus grown in cell culture as described herein.

PCR assays for DNA templates: Background templates are added to each 25 ul reaction in the following amounts: 5 ng of total soil extract, 1 ng of total Eukaryotic extracted DNA and 200 pg of total extracted Prokaryotic DNA. Control on each plate consists of 2 *Bacillus thuringiensis* reactions (1 ng DNA per 25 ul reaction), and an NTC (No Template Control=5 ul PCR water in place of the template), for each primer used on the plate. Each reaction includes the following: 10×PCR Buffer (2.5 ul); 10 mM dNTPs (2.0 ul); 50 mM MgSO4 (2.25 ul); BSA (2 ug/ul) (1.0 ul); F/R Primers (2.5 uM) (1.0 ul); PlatinumTaq (0.125.0 ul); PCR water (11.125 ul); Template (in 5.0 ul). Thermalcycler Parameters are as follows: Cycle 1: (1×): Step 1: 94.0° C. for 01:00; Cycle 2: (39×) Step 1: 94.0° C. for 00:20; Step 2: 55.0° C. for 00:10; Step 3: 72.0° C. for 00:30; Cycle 3: (1×) Step 1: 15.0° C., HOLD.

PCR assays for RNA templates: Primer set assays are performed in triplicate against available RNA extractions of targets and near neighbors using 200 pg of extracted RNA to each 25 ul reaction. Each reaction includes the following: 2× One-step RT-PCR Buffer (12.5 ul); 50× Q Taq Polymerase Mix, 1.5 U/ul (0.5 ul); 60× Q PowerScript (0.42 ul); PCR water (5.53 ul); F/R Primers (10 uM) (1.05 ul); Template in 5 ul. Thermalcycler Parameters are as follows: Cycle 1: (1×) Step 1: 48.0° C. for 20:00; Step 2: 95.0° C. for 03:00; Cycle 2: (39×): Step 1: 95.0° C. for 00:15; Step 2: 60.0° C. for 01:00; Step 3: 72.0° C. for 00:15; Cycle 3: (1×): Step 1: 15.0° C. HOLD.

Gel electrophoresis. Product size was determined by running 15 ul of PCR product with 5 ul 10× loading dye (Teknova; Hollister, Calif.) on 4% agarose gels (Cambrex Rockland, Ind.) in Tris-borate-EDTA buffer (Teknova). Band size was determined using Cambrex's Simpleload 20 base pair ladder. The Epi Chemi II Darkroom Bioimaging system (UVP BioImaging Systems Upland, Calif.) was used for visualization of the DNA.

Results. For the respiratory assay panel under development, after removing signatures that cross-reacted with background signatures, the number of suitable candidate signatures produced by the informatics team were significantly reduced, leaving 8 signatures for influenza, 7 for parainfluenza, 8 for adenovirus, 1 for RSV, and 1 for SARS.

Example 4

Taqman Format Screening

Following the wet screening process, signature sequences were screened in a real-time PCR format in triplicate against nucleic acid samples that include nucleic acid extracts from all targets and near neighbors, 16 eukaryotes, 55 soils, 45 prokaryotes, and a total of 2256 samples collected from aerosol collectors and pooled for background testing purposes. Primer pairs that successfully pass the wet chemistry screening criteria are advanced to the assay development stage.

Taqman assay development includes the bioinformatics selection and evaluation processes, and optimization and characterization. Optimization is conducted for every relevant parameter that impacts assay performance. For example, in a standard RT-PCR assay, parameters to be optimized include: primer/probe length, GC content, Tm, concentration(s), thermocycling parameters (2-step or 3-step, times, temperatures for each step) reaction conditions (MgCl2 concentration), Taq polymerase (type and concentration), reaction buffers, extraction protocols, etc.

Taqman probes: Probes for Real-time PCR Taqman reactions were obtained from Biosearch Technologies using the Tamara fluorophore and Black Hole quencher. In some instances the Taqman probes had the same sequence as the probes used in the multiplex Luminex assay and described in Table 1, e.g., the Taqman probes were forward complement probes (FCP). In other instances, the Taqman probes were the reverse complement of probes disclosed in Table 1 and used in the Luminex assay. The Taqman primers and probes were as follows:

TABLE 4

Primer and probes for Taqman assays

| Signature Name | Forward Primer Sequence (5'=>3') (Forward Primer sequences disclosed as SEQ ID NOS 103-152, respectively, in order of appearance) | Reverse Primer Sequence (5'=>3') (Reverse Primer sequences disclosed as SEQ ID NOS 153-202, respectively, in order of appearance) | Probe Sequence (5'=>3') (Probe sequences disclosed as SEQ ID NOS 203-252, respectively, in order of appearance) |
|---|---|---|---|
| H1 FluA 000005_1 | TGCAAACAACTCTACAGACACTG TTG | AGTTTGCAGTGAGTAGAAGGTCAC A | CACTCAGTGAATTTGCTCGAAGACAGCCATAA |
| H1 FluA 000022_1 | AGCGTCAAAAATGGGACTTATGA | AAAGACCCATTAGAGCACATCCA | TGGCGATCTATTCAACTGTCGCCAGTT |
| H1 FluA 000007_1 | AAAACTCTGCAGCCTGAATGG | GGGTAGCATGTTCCATTTTCTGA | TCCTTGGCAACCCAGAATGTGACTTGT |
| H1 FluA 000001_1 | CTTTCAGCTACAGATGCAGACAC A | TTCCCATTGTGACTGTCCTCAA | CGAACAATTCAACCGACACTGTTGACACA |
| H1 FluA 000046_1 | ATCAGAATGAACAGGGATCAGGA TA | ATCCAGAAAACCATCATCAACCTT | TGCCATTGACGGGATCACTAACAAAGTAAATTC |
| H1 FluA 000022_1 | ATGCATATGTTTCAGTTGGATCA TC | TCAATGCGAATGCGTACCA CC | CATAACTTTTGAAGCCACTGGGAACTTAATAGCA |
| H1 FluA 000041_1 | GCCATTAACGGGATTACAAACAA G | CCAGTAGAACCAACAATTCTGCAT TAT | TCGAGAAAATGAACACTCAATTCACAGCTGTG |
| H3 FluA 008182_1 | ATGCTGAGGATATGGGCAATG | GATATGGCAAAGGAAATCCATAGG | CATTAAACAACCGGTTCCAGATCAAAGGTGT |
| H3 FluA 000053_1 | AATGGATGGGAAGGAATGATAGA C | TGGATTCTTCCTTCTACTTCAGAG AAT | CACACAGGCAGCCATTGACCAGATTAATG |
| H3 FluA 000053_1 | ATTCCAGATCAAGGGTGTGGAA | TCTCTGGCAGGCCCACAT | CCTTGCCATATCATGCTTTTTGCTGTGTG |
| H3 FluA 000003_5 | CATCATGCGGTACCAAATGG | AGTGAGGGTCCCCCAATAGAG | CTCATCGAATTCTTGATGAGCAAATTGCAC |
| H3 FluA 000031_1 | TATCACAAATGTGATAATGCATG CA | ATGAAACCCAATAGAACAACACAA ATT | TGTGGATTTCATTCGCCATATCATGCTTC |
| H5 FluA 009339_1 | GGGAGGAAATAGACGGAGTCAAA | TAGATGCAAATTCTGCACTGCAA | TCAACAGTGGCGAGTTCCCTAGCACTG |

TABLE 4-continued

Primer and probes for Taqman assays

| Signature Name | Forward Primer Sequence (5'=>3') (Forward Primer sequences disclosed as SEQ ID NOS 103-152, respectively, in order of appearance) | Reverse Primer Sequence (5'=>3') (Reverse Primer sequences disclosed as SEQ ID NOS 153-202, respectively, in order of appearance) | Probe Sequence (5'=>3') (Probe sequences disclosed as SEQ ID NOS 203-252, respectively, in order of appearance) |
|---|---|---|---|
| H5 FluA 000722_1 | GTATGGGTACCACCATAGCAATGA | TGTTCATTTTGTCAATGATCGAGTT | TGCAGACAAAGAATCCACTCAAAAGGCAA |
| H5 FluA 006709_1 | GATCTAAATGGAGTGAAGCCTCTCAT | TATGTAAGACCATTCCGGCACAT | CTGGATGGCTCCTCGGAAACCCTATGT |
| H5 FluA 011991_1 | GACAATGAATGTATGGAAAGTGT | ATCCAAAAGATAGACCAGCTATC | CAGTGGCAAGTTCCCTAGCACTGGCA |
| H7 FluA 000002_1 | ATTCTAATATTAGCCATTTCGGCATT | TCTATTCCCTTTTCAGTAAGGGTGTCT | CAGATAAAATCTGCCTAGGACATCATGCTGTGTC |
| H7 FluA 010749_1 | AGAGGCATTGCGACAAATCC | TGTTTTTGTATGATTTTGTCATTTGTG | TGGCTCCTGTCAAATACAGACAATGCTTCTTTC |
| H7 FluA 005344_1 | AATATCAACAATCATTCACCCCAAGT | GTCACTGTGTCATTGGGATCAAG | CACGGCCACAAGTGAATGGACAATCA |
| H7 FluA 000025_1 | GATCCCAATGACACAGTGACCTT | TTCCCCACAGTTCTAGGGTTGA | CATAGCCCCTGACAGGGCAAGTTTCTTTAG |
| H7 FluA 000004_1 | GTGGCGATCATCCCAACA | GCTCCACTGTTTCAGTTGCATT | CTTGGGCATCATGCCGTGTCAAAC |
| H7 FluA 000049_1 | GGCTACAAAGATGTGATACTTTGGTTT | CATGTTTCCATTCTTCACACACAT | CTTCTGGCCATTGCAATGGGCC |
| H7 FluA 009496_1 | TTGATGGATGGTATGGCTTCAG | CAATTTATCACATTGCCAATTTGC | CACTCAATCGGCAATTGATCAAATAACAGGA |
| H7 FluA 000403_1 | TAAGCAGCGGCTACAAAGATGT | GCACCGCATGTTTCCATTT | CATGTTTCATCTTCTGGCCATTGCAATGG |
| H7 FluA 000013_1 | CCGTTTAATTGACAAGACAAATCAAC | CGTAGAGTTTGTTCATTTCTGAATCTG | TGGCCATGGAGAATCAACACACAATAGATCTT |
| Adenovirus B_1770195 | CGCTTTCACAGTCCAACTGC | GCTGCTTGTGGGTTTGATGA | CGTTTTCGGATTATGATTCCCATCGTTCTTC |
| Adenovirus B_1770201 | TCCTGCACCATTCCCAGATA | CCTCCGGGACCTGTTTGTAA | CAGCTTTCCAGCCTTGAATTATTCGTGTCAG |
| Adenovirus C_1768012 | AGCGCGTAATATTTGTCTAGGGC | TCAGCTGACTATAATAATAAAACGCCA | CGGAACGCGGAAAACACCTGAGAAAA |
| Adenovirus C_1768014 | TCGATCTTACCTGCCACGAG | GCCACAGGTCCTCATATAGCAA | TGCTCCACATAATCTAACACAAACTCCTCACCC |
| Adenovirus C_1768035 | AGGTCCTCCTCCCTCCTACG | CACACGGGTGGTGTCGAATA | TGCCAACTCAGAGTAACGGATGCTGTTTCTC |
| Adenovirus C_1768040 | CCCAACACCTAGCCTAAAGCC | TTTCCAAGACATCTTCCAGTCG | AAGTCACCAGACTCGCGCTTTAGGCC |
| Adenovirus C_1768046 | TAATGATGGCCGCAGTGCT | CCTCTAGCTTGCGCTGCAT | CTGCATGCACTCAAGCTCCACGGTAAC |
| Adenovirus D_1768064 | TGCATGATGGGAATGAGAGC | CATCCCCTGATCTTGGAAGC | ACCTCTGCGCACATATTGTTAAAGCCGAAAA |
| Adenovirus D_1768089 | TGGTCCAGATGGAAAGGTCA | CTTTGCTGTTGCCTCTGTCA | TGTCACACTTACACCCTAACTTATACCCAGGCTCA |
| Adenovirus D_1768091 | GCGTTCTGATTAGCATAGTCACACT | GCATTTGTATGCAGTAACATTCCA | TTGTCCATGTAGTTTGTGGATAAGTCCCATTCA |
| Adenovirus E_1759552 | GCATCGGCACTCTCCAGTT | CACCATGGGACATTCAATCG | AGTTCACTCCCTCGGTCTACTTCAACCCCTT |

TABLE 4-continued

Primer and probes for Taqman assays

| Signature Name | Forward Primer Sequence (5'=>3') (Forward Primer sequences disclosed as SEQ ID NOS 103-152, respectively, in order of appearance) | Reverse Primer Sequence (5'=>3') (Reverse Primer sequences disclosed as SEQ ID NOS 153-202, respectively, in order of appearance) | Probe Sequence (5'=>3') (Probe sequences disclosed as SEQ ID NOS 203-252, respectively, in order of appearance) |
|---|---|---|---|
| Adenovirus E_1759558 | TGCAATTTTGTTGGGTTTCG | CCTGGCTGTTATTTTCCACCA | TTAATCATGGTTCTTCCTGTTCTTCCCTCCC |
| Parainfluenza 1_1770229 | AAGTCCACCAACTCCCGAAC | CATGCGCTTAGCAAATACATGA | CACATCGGTCGATGAGATGGCCAAGTTATTA |
| Parainfluenza 1_1770233 | GGAATCATAAGAAGAAAAGTTGG | TCCATGCAAGTTGGCTCATT | TTTTGGATAATGTGCCTGTTGCATGTACATGG |
| Parainfluenza 1_1770236 | TGGCTAATTGCATTGCATCC | CTCGTCCCCTTTTATTGGCA | ACATGCGGGACAAACAGAATACCAGTGAATC |
| Parainfluenza 1_1770237 | CGAAATGACAATTCCACGGTAA | TTTGGCACTTTCGTTCATGG | CATCTGGCTACTGATTGCAACAACAATGCAT |
| Parainfluenza 1_1770240 | CCTGTCTCGACCAGGAAACC | TGGTGGGATTAACACGTGATGT | AGACTGCAACTGGTACAACAGATGTCCGAGA |
| Parainfluenza 2_1770386 | TGTCAAGTAATTGCGGAAGCA | GCCAATTTGACTCATAGTAAGCAA TG | AAGACAACTCCGTTTTCCTTCATTAGAGTACCTG C |
| Parainfluenza 2_1770387 | CAAGGTTTCCATACAATCAAGAC TGA | TGGATTATGGTCTGATATCTCCAT TG | TGCATCATCATACCTCACAGATCCTGATGA |
| Parainfluenza 3_1770258 | TCAGGAAACTATGTTGCAGAACG | AGCTTCCAATCGGGTGAAAA | AACAATTGAAGACCTTGTCCACACACATTTGGG |
| Parainfluenza 3_1770275 | CAACGGAATGCTGTTCAATACAA | TCTTCTAGATCTGATTTGGCCTTG | TGAGCTCGATTGATATGTCAATTGGATCAAGTG |
| Parainfluenza 3_1770285 | TCGGGTTGGCATAAATAGAGG | TTCCTCCTGATAAATGAATCCACA | CTTTTGTCGCAATGCTATGGCAAGGTCTAC |
| RSV_1769653 | AATGCTATCACCAATGCGAAAA | AACGTGAGCTGTATGCTTCCAA | TGACAATAAAGGAGCATTCAAATATATCAAGCCA CA |
| RSV_1769664 | TGTTCTCTTGGTTGCATTTAACA AT | TGATATAGCTTCAATGGTCCACAG T | ACATGCACCTCCTTTCATAAAGGATCATGTTG |
| SARS | CCTAGGGCGCTGTGACATA | CAAAACCTGAATCAGTGCCTACAC | ACCTGCCAAAAGAGATCACTGTGGCTACATC |

Sample preparation, DNA: Total DNA was extracted from virus infected cell culture as follows. Add $5\times10^{-2}$ nanograms of Puc18 per ml of virus cell culture (to 15 ml add 0.75 ng Puc19). Add Triton X-100 to a final concentration of 0.5% V/V (to 15 ml add 75 ul Triton). Add 0.5M EDTA to a final concentration of 20 mM (15 ml add 600 ul 0.5M EDTA. Mix vigorously and vortex, let sit 5 min at room temp. Spin tube at <1000 rpm for 10 minutes. Discard pellet and to the supernatant add 10% (W/V) Sodium Dodecyl Sulfate (SDS) solution to a final concentration of 1% (to 15 ml add 1.5 ml of 10% SDS). Add proteinase K to a final concentration of 0.4 U per ml (to 15 ml add 2.4 mg of 2.5 U/mg Roche or 60 ul of a 0.1 mg/ul solution of proteinase K in water). Incubate the tubes at 55° C. for one hour mixing every 10 minutes. Cool tubes to room temperature. Add 5 M NaCl to a final concentration of 150 mM (to 16.5 ml add 510 ul 5 M NaCl). Add an equal volume of room temperature phenol/chloroform/isoamyl alcohol (approx. 15 ml). Mix by inversion and swirling till phases are completely mixed. Let sit 5 min then spin at 3,000 rpm for 10 min. Remove the upper aqueous layer and distribute 500 ul into 1.5 ml microcentrifuge tubes (for 15 mls need 30 tubes). Discard the lower layer in phenol/chloroform waste. Add two volumes (1 ml) of 100% ethanol to each microcentrifuge tube and leave at −20° C. one hour. Spin in microfuge at top speed refrigerated for 10 minutes. Discard supernatant and wash pellet once with 70% ethanol 150 mM NaCl. Remove all ethanol and dissolve the pellet in TE. For 15 ml extraction dissolve each pellet in each tube in 50 ul of liquid. Each tube should contain 50 fg/ul of puc 18.

Sample preparation, RNA: RNA was extracted from virus infected tissue culture samples as follows. Add 3× the volume Trizol (TRIZOL LS Invitrogen Cat. No. 10296-010) to the volume of sample. (Upon completion of this step, sample can be stored at −80, or continue with extraction.) Lyse cells in the sample suspension by passing the suspension several times through a pipette, or by shaking vigorously. Incubate for 15 minutes at room temperature. (Typically, LLNL uses 2× the volume Trizol to water (e.g., 15 ml sample and 30 mls TRIZOL.) Add 200 ul chloroform per 1 ml solution in the fume hood, cap and shake vigorously for 15 seconds. Incubate at room temperature for 5-15 minutes. Centrifuge at 3000 g for 15 minutes, at 4° C. Remove aqueous layer. Add 1 ml isopropyl alcohol per 500 ml aqueous layer. Gently mix by inverting several times. Incubate samples on the bench top for 10 minutes. Centrifuge at 12,000 g for 10 minutes at 4 C. Carefully, pour off liquid. Wash pellet with 70% EtOH. Vortex sample and re-centrifuge at 7,500 g for 5 minutes at 4° C. Pour off the EtOH, cap, re-spin at 7,500 g for 5 minutes and pipette off remaining liquid. Air dry briefly at 55° C., caution not to over-dry. Resuspend RNA in RNAse-free water and store at −80° C.

Reverse transcriptase. RNA samples were subjected to reverse transcription using the BD Clonetech kit, 48 degrees C. for 30 minutes.

Real-time PCR for DNA samples. Primer/probe set assays were performed in triplicate against 54 extracted soil samples, 16 Eukaryotic backgrounds and 45 Prokaryotic backgrounds and against 3 distinct aerosol extraction plates, adding 5 ul template to each 25 ul reaction. Background templates, with the exception of aerosols, were added to each 25 ul reaction in the following amounts: 5 ng of total soil extract, 1 ng of total Eukaryotic extracted DNA and 200 pg of total extracted Prokaryotic DNA. (The backgrounds are pre-made up in plates that are diluted to the proper concentrations so that 5 ul of each background is added to each 25 ul reaction.) Controls on each plate consist of 2 *Bacillus thuringiensis* reactions (1 ng DNA per 25 ul reaction), and an NTC (No Template Control=5 ul PCR water in place of a template), reaction for each primer/probe on the plate.

| Component | 1x (ul) |
|---|---|
| 10x PCR Buffer | 2.5 |
| 10 mM dNTPs | 0.5 |
| 50 mM MgSO4 | 3.0 |
| BSA (2 ug/ul) | 1.0 |
| F/R Primers (10 uM) | 0.5 |
| Probe (10 uM) | 1.0 |
| PlatinumTaq | 0.25 |
| PCR Water | 11.25 |
| Template (**/ul) | 5.0 |

| iCYCLER Parameters | | |
|---|---|---|
| Cycle 1: (1X) | 95.0° C. for 01:00 | |
| Cycle 2: (39X) | 95.0° C. for 00:20 | Data collection and real-time analysis enabled |
| | 55.0° C. for 00:10 | |
| | 72.0° C. for 00:30 | |
| Cycle 3: (1X) | 4.0° C. HOLD | |

PCR for RNA samples. Reverse transcriptase Real-Time Procedure. Follow steps 1 and 2 of the Real-Time DNA procedure for background screening on each signature. Perform primer set assays in triplicate against RNA extractions of targets and near neighbors using the Clonetech RT-PCR kit. Controls on each plate consist of 2 *Bacillus thuringiensis* (Bt) reactions (1 ng DNA per 25 ul reaction), and an NTC (No Template Control=5 ul PCR water in place of a template), reaction for each primer/probe on the plate. Be sure to use the Clonetech RT-KIT for Bt controls on RNA plates.

Clontech RT-PCR Reagent Mix Preparation:

| Component | 1x (ul) |
|---|---|
| 2x One-step RT-PCR Buffer | 12.5 |
| 50x Q Taq Polymerase Mix, 1.5 U/ul | 0.5 |

-continued

| Component | 1x (ul) |
|---|---|
| 60x Q PowerScript | 0.42 |
| PCR water | 5.33 |
| F/R Primers (10 uM) | 1.05 |
| Probe (10 uM) | 0.20 |
| Template, concentration varies | 5.0 |

| iCYCLER Parameters | | |
|---|---|---|
| Cycle 1: (1X) | 48.0° C. for 20:00 | |
| Cycle 2: (39X) | 95.0° C. for 00:10 | Data collection and real-time analysis enabled |
| | 60.0° C. for 01:00 | |
| | 72.0° C. for 00:15 | |
| Cycle 3: (1X) | 15.0° C. HOLD | |

PCR efficiency. The efficiency, of the PCR assay was determined by testing dilutions from 3000 pg to 10 pg in triplicate. The average ct value was graphed against the template concentration, the equation of the resulting line yielded the R2 value that represents the PCR efficiency.

Signature sequences that performed well in the Taqman format are presented in Table 1.

Example 5

Development of Multiplexed Liquid Array Format

Figure 2:
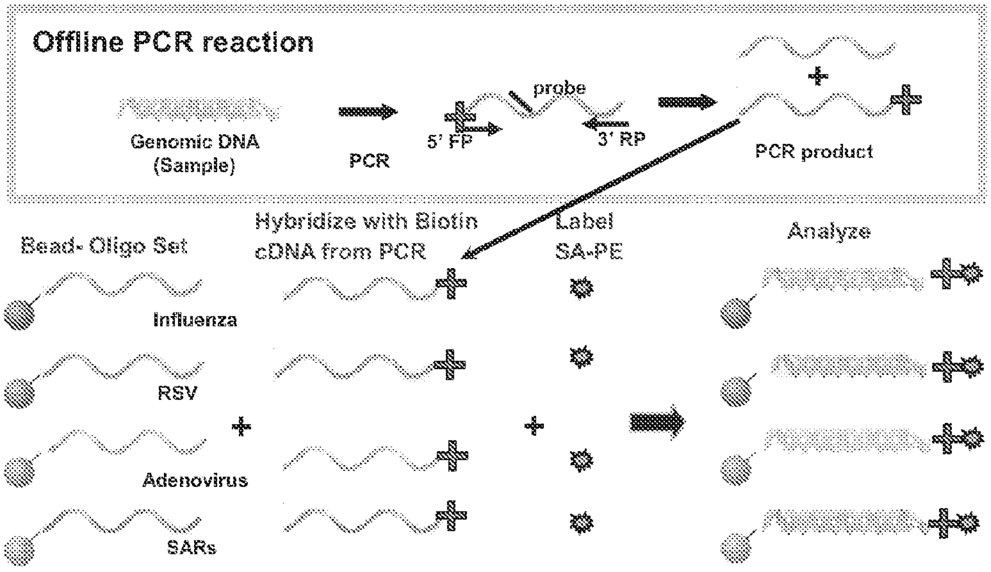
FIG. 2 illustrates one embodiment of detection of signature sequences in a sample via PCR amplification of signature sequences in the target and hybridization to probes covalently coupled to beads. Individual primer pairs (biotinylated forward and standard reverse) that bracket the target genomic sequence are included in an automated PCR master mix of buffers, Taq polymerase, dNTPs, etc. After target amplification by PCR, the amplicons are mixed with beads where target amplicons containing the forward biotinylated primer hybridize to the complementary probe on the appropriate beads. A fluorescent reporter molecule (strepavidin-phycoerythrin) then binds biotin functional groups. Therefore, the completed assay comprises a bead+probe+biotinylated (and fluorescently tagged) amplicon. The sample is then analyzed using a Luminex detector.
Figure 3:
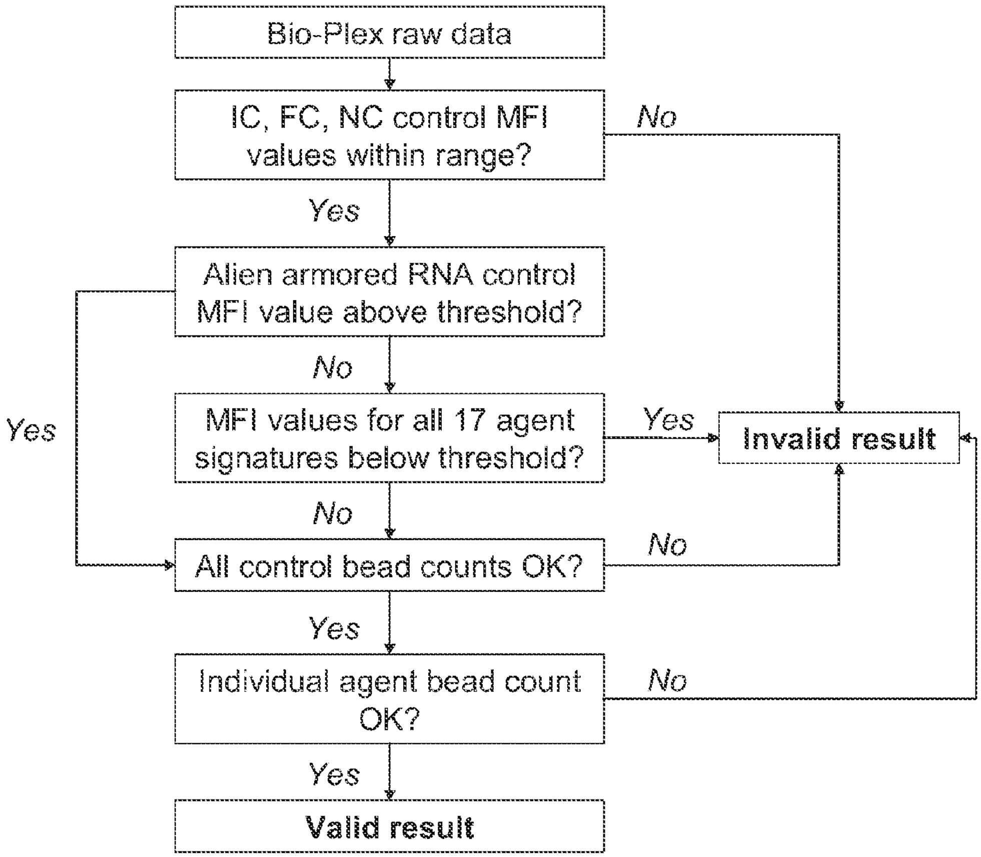
FIG. 3 is a flow diagram illustrating the process used to determine whether or not any individual assay result is valid based on results of the control data.

After ascertaining that signatures perform well in the Taqman format, they are then transitioned to the multiplexed liquid array format. The multiplexed liquid array format is summarized in FIG. 2.

This phase is divided into two steps. The first step, called 'Singlepex' testing, is a step in which each individual signature is tested against target virus. In this format, only two sets of primers are present in the PCR mix: the primers for the Alien RNA positive control (to ensure the PCR reaction proceeds well), and the primers for the signature being tested. The target virus is then spiked at various concentrations in order to generate a titration curve. All titrations are run in triplicate. In the cases in which various strains of the same virus are available, a titration is run for each one.

The second step, called 'Multiplexed' testing, is a step in which the individual signatures are added to the multiplexed panel. In this format, the primers of the signature being tested are added to the multiplexed PCR mix, with the other primers present in the panel. Titrations are then run in triplicate for each signature present in the panel in order to determine the limit of detection of the assay against each target in the multiplexed format, and also to control for signature cross-reactivity.

A summary of the multiplex PCR assay procedure is as follows. The sample, e.g., an oral swab placed in virus transport media, undergoes a magnetic bead extraction to purify target nucleic acids from impurities in the sample matrix. Target DNA or RNA is amplified by real-time-PCR. The forward primer is biotinylated. The reverse primer is unmodified. The double stranded PCR product is mixed with a suspension of probe-bead conjugates then melted at 95° C. to form single strand product. Extended forward primer is hybridized to the complementary probe-bead conjugate at 95° C. The hybridized product is then labeled with the fluorescent probe SA-PE. The bead suspension is analyzed using the flow cytometer.

For this application, oligonucleotide probes with sequences that are complementary to the target nucleic acid sequences were covalently coupled to beads. Nucleic acids from pathogens (targets) were amplified using standard PCR techniques. After target amplification, the amplicons, half of which contain the biotinylated forward (5'-3') primer were introduced to the beads and allowed to hybridize to their complementary probes on the appropriate bead. A fluorescent reporter molecule (strepavidin-phycoerythrin) was added, and binds the biotin functional groups within the forward primer. Therefore, the completed assay product comprises a bead+probe+biotinylated (and fluorescently tagged) amplicon. Each optically encoded and fluorescently-labeled microbead was then interrogated by the flow cytometer. The 635-nm red diode laser excites the dyes inside the bead and classifies each bead to its unique bead class, and a green "reporter" laser (532 nm) quantifies the assay at the bead surface. The flow cytometer is capable of reading several hundred beads each second; analysis can be completed in as little as 15 seconds. Conducting the assay requires multiple steps and significant thermocycling times; the process currently takes about 2 hours.

Extraction of Target Nucleic Acid from a Sample

Extractions of nucleic acid from the samples were conducted with an MagMax (catalog #1839, Ambion, Austin, Tex.) extraction kit using the standard protocol. The kit is specifically designed for the simultaneous extraction of both DNA and RNA using a single procedure. Nucleic acid was extracted from deactivated antigens to use as positives when testing the various signatures.

Primer and Probe Synthesis

Oligonucleotides for Luminex bead-based assays were purchased from Integrated DNA technologies (IDT DNA, Coralville, Iowa). Each forward primer has a 5 prime biotin and 2 internal biotins. Since the biotin molecules are proportionately larger than the bases, it is preferred that the biotins be separated by about 5-10 bases and it is important that there is not a biotin too near the 3 prime terminus of the forward primer, as this could interfere with amplification efficiencies. The reverse primer was unmodified.

The probe was modified with a 5' amine and a space amine modification for coupling the microbeads, e.g., if the real-time PCR probe sequence is 5' FAM-ATCCGCGCATAG-TAM3' (SEQ ID NO: 253), the Luminex probe sequence becomes 5'/5AmMC12//iSp18//ATCCGCGCATAG-3' (SEQ ID NO: 254).

A number of oligonucleotide synthesis parameter were optimized for the multiplex, Luminex based assays. First, all oligonucleotides were HPLC purified. A small percentage of probes produced were contaminated by free biotin molecules that are residuals from the primer production. This contamination can cause undesirable interference with the assay. To minimize this occurrence and improve quality control, we have requested that IDT includes a SA (streptavidin agarose) purification followed by sephadex filtration to remove any contamination. We have also found that impurities in the oligonucleotides (synthesis "artifacts"; buffer crystals, truncated products, etc) can also weaken assay performance. As a result we require purity to be a minimum of 85% to pass quality standards with less than 15% impurities. Quality control documentation; signed ESI Mass Spectrometry Trace and Capillary Electrophoresis Trace was required. Oligonucleotides were shipped as lyophilosized pellets and are then resuspended to their desired concentrations; primers in TE [Tris EDTA, pH 8] buffer and probes in 0.1M MES [(2-{N-morpholino}ethanesulfonic acid)] buffer, pH 4.5. All oligonucleotides are stored in small aliquots at −20° C.

Covalent Coupling of Oligonucleotide Probes to COOH-Microbeads:

Different sets of carboxylated fluorescent microbeads were obtained from Luminex Corp (Austin, Tex.), and probes for each assay were assigned to a unique bead set. Oligonucleotide probes, with sequences representing the reverse complement to target region of the forward strand (5'-3') were obtained from Integrated DNA Technologies (Coralville, Iowa). Each probe contained a C-18 spacer between the amine reactive group and the 5' end of the oligo to enable optimum hybridization. Probes for each of the pathogen targets were coupled according to the manufacturer recommended coupling protocol. Briefly, a homogenized 1 ml aliquot (1.25×107) of beads was centrifuged for 5 min. at 13,000 rpm, and re-suspended in 50 μl of 100 mM 2-[N-morpholino] ethanesulfonic acid (MES) buffer, pH 4.5. To this suspension, 10 μl of probe at a concentration of 50 μM was added followed by addition of 50 μg of 1-ethyl-3-[3-dimethylaminopropyl]-carbodiimide hydrochloride (EDC) (Pierce Biotechnology [CU1], Rockford, Ill.). This solution was incubated in the dark at room temperature for 30 minutes. A second aliquot of EDC (25 μg) was added and incubated as before. The beads were rinsed in 1 ml phosphate buffered saline (PBS) containing 0.02% Tween-20 (Sigma), centrifuged at 13,000 rpm for 5 min, rinsed using 1 ml of 0.1% (w/v) sodium dodecyl sulfate (SDS) in water, and centrifuged as before. The supernatant was aspirated and the conjugated beads were washed in 100 μl of TE (10 mM Tris, 1 mM EDTA, Ph 8.0 [Sigma]) and then re-suspended in 250 ul TE and stored in the dark at 4° C. Each probe/bead conjugate was stored separately, and a fresh bead set containing all conjugates was prepared for each liquid bead array assay.

Multiplexed PCR Amplification:

Each amplification reaction was performed in a total volume of 25 μl. The reaction mix consisted of 12.5 μl of 2× Superscript III RT-PCR reaction Mix (Invitrogen, Carlsbad, Calif.), 0.11 each of forward and reverse primers (each at a concentration of 100 μl), 1 μl per reaction of Superscript III/Platinum Taq Enzyme Mix, 0.95 μl of 50 mM MgSO4 (Invitrogen, Carlsbad, Calif.), 1 μl of 100 copies/μl "Alien RNA" internal control template (Ambion, Austin, Tex.), 5 μl of template, and enough RNase-free water to bring final volume to 25 μl. The "Superscript III RT-PCR System" kit 2× reaction mix contains 0.4 mM of each dNTP and 3.2 mM MgSO4 plus "proprietary stabilizers". With the addition of 0.95 μl of 50 mM MgSO4, the final component concentrations in the 1× reaction mix were as follows: 0.2 mM each dNTP, 3.5 mM MgSO4, 1× Superscript III RT-PCR buffer, 0.4 μM of each primer, and 300 copies of Tobacco Mosaic Virus internal control template. The Platinum Taq polymerase used is a "Hot Start" Taq that is robust and is held by binding a thermolabile inhibitor containing monoclonal antibodies to Taq polymerase.

Thermocycling conditions were as follows: 30 min at 55° C., 2 min at 95° C., followed by 35 cycles of 15 sec at 94° C., 30 sec at 60° C., 15 sec at 72° C., and concluding with one cycle at 72° C. for 2 min. followed by 4° C. soak.

Hybridization of Amplified Sample to the Bead:

A bead set was prepared, consisting of a mixture of 3 μl of beads each covalently coupled to a probe listed in Table 1 into a volume equal to 1 ml of Tris-NaCl buffer (100 mM Tris, 0.05% Triton X100, 200 mM NaCl pH 8.0). Amplified PCR reaction product, e.g., amplicon (1 μl) was added to 22 μl of the bead mix. PCR products and bead mix were denatured at 95° C. for 2 min and allowed to hybridize at 55° C. for 5 min. The mix was transferred to a 96 well filter plate (Millipore, Bedford, Mass.). The beads were washed twice in 100 µl Tris-NaCl and incubated with 60 µl of 3 ng/µl Streptavidin-phycoerythrin (SAPE) (Caltag Laboratories, Burlingame, Calif.) for 5 min. The hybridized beads were washed again with 100 µl Tris-NaCl buffer and re-suspended in a final volume of 100 µl Tris-NaCl buffer. The completed sample was then introduced to the Luminex flow analyzer for analysis.

Example 6

Controls for the Multiplexed Liquid Format Assay

Controls that convey important diagnostic information regarding reagent addition, quality and concentration, assay operator performance, and instrument stability can be easily added without compromising or limiting the screening capabilities of an assay. The disclosed assays employ a unique set of four rationally-designed internal controls built into every sample that monitors and reports every step of the assay. In some embodiments, the kits and methods of the invention use at least one or, alternatively, all of the controls described herein.

IC: Instrument Control: The purpose of this control is to inform the user of the reporter laser's integrity and utility. It is a bead coupled to BSA conjugated to tetramethylrhodamine (TAMRA), a heat stable fluorophore; it automatically fluoresces and generates a signal in the presence of the reporter laser. If one notices a decline in the signal, it is due to decline in the laser's integrity. Under those circumstances, one must contact BioRad (or Luminex Customer Support) for a service request. The laser's output is important to monitor because it has a finite lifespan. This control is generally the most robust.

FC: Fluorescence Control/SAPE Addition Control: As a fluorescent control, or SAPE addition control, biotinylated BSA (b-BSA) is coupled to one of the beads. The biotin molecule has a very high binding affinity for streptavidin (biotin-avidin binding) and the Phycoerythrin (PE) component of SAPE is what is detected by the reporter laser (same as the fluorophore bound directly to the bead for the IC). If one does not detect a signal on the FC, then it is likely that SAPE was not added.

NC: Negative Binding Control: The NC is a bead bound to a DNA sequence specific to a random sequence from the genome of an organism found at the bottom of the ocean (Maritima maritensis, Mt7). MT-7 is a conserved DNA sequence from a maritima organism (a thermal vent microbe) that does not match those of published genomes of terrestrial organisms, and serves as a non-specific binding control in the multiplex PCR assay. In the absence of non-specific binding, the MFI values for the NC MT-7 bead should remain consistently low.

PCR/RT-PCR PC: RNA Amplification Control/Inhibition Control: Alien armored RNA (arRNA Alien) is a synthetic RNA sequence, ~1000 nucleotides in length, packaged in an MS2 phage (protein capsid). The sequence is termed "alien" as it has no homology to currently annotated GenBank sequences. Packaging increases the stability of the RNA in clinical sample matrices and more closely mimics the behavior of target virus particles during processing. An internal control assay for alien armored RNA was incorporated into the multiplex PCR assay using specific primers and probe. Alien armored RNA is used as an end-to-end internal control for reverse transcription, PCR amplification, Luminex microsphere array hybridization and Bio-Plex detection.

The alien RNA concentration used is typically 200 copies per well, which consistently yields a median fluorescent intensity (MFI) value above the assay detection limit for both clean and clinical sample matrixes. A low number copy number for the internal control was selected to minimize competition within the PCR reaction with the agent signatures. A low copy number can also better reflect detrimental changes in assay performance that could potentially result in a false negative. MFI values below threshold may indicate failed reverse transcription and PCR amplification, or a failed hybridization reaction.

Positive Control: An additional positive control was developed to assay for PCR. The positive control template is added to samples along with the PCR reaction mixture; detection of the positive control amplicon indicates that PCR occurred.

Hybridization Control: A hybridization control template is added to samples before processing; detection of the hybridization control via the Luminex indicates that the PCR reaction was correctly added to the bead mixture.

Patient addition Control: A patient control template is added to samples before processing; detection of the patient control via the Luminex indicates that patient samples were correctly added to the bead mixture.

Sequences of the controls used in the multiplexed liquid format assay are shown in the following table.

TABLE 5

| Controls for multiplexed liquid format assay | | | | |
|---|---|---|---|---|
| CONTROLS | Sequence 5' => 3' | SEQ ID NO: | With label/adaptors (if applicable) | SEQ ID NO; |
| Negative Control MT7 | CAAAAGTGGGAGACGTCGTTG | 255 | /5AmMC6//iSp18/CAAAGTGGGAGACGTCGTTG-3' | 267 |
| Instrument Control MT7/Cy3 | CAAAGTGGGAGACGTCGTTG | 256 | /5AmMC6//iSp18/CAAAGTGGGAGACGTCGTTG-3'Cy3 | 268 |
| Fluorescent Control b-MT7 | CAAAGTGGGAGACGTCGTTG | 257 | /5AmMC6//iSp18/CAAAG/iBiodT/GGGAGACGTCG/iBiodT/TG-3' | 269 |
| Positive Control forward primer TM1799179.BF | TCGTCGATGGTGGTATGACG | 258 | /5Bio/TCGTCGATGGTGGTATGACG-3' | 270 |

TABLE 5-continued

| Controls for multiplexed liquid format assay | | | | |
|---|---|---|---|---|
| CONTROLS | Sequence 5' => 3' | SEQ ID NO: | With label/adaptors (if applicable) | SEQ ID NO; |
| Positive Control probe TM1799179. Prb | CCAGCTCGATCACTCCTCGTATATCATCTTCA | 259 | /5AmMC6//iSp18/CCAGCTCGATCACTCCTCGTATATCATCTCA | 271 |
| Positive Control reverse primer TM1799179. R | CTCCGAATGCAATTGTCAGG | 260 | n/a | |
| Positive control amplicon TM1799179 | TCGTCGATGGTGGTATGACGGTGAAGATGATATACGAGGAGTGATCGAGCTGGATTACCTGACAATTGCATTCGGAG | 261 | n/a | |
| Hybridization Control Probe (on bead) | CCAGTTCTTCCGGATACGGCTGGCCT | 262 | /5AmMC6//iSp18/CCAGTTCTTCCGGATACGGCTGGCCT-3 | 272 |
| Hybridization control template | AGGCCAGCCGTATCCGGAAGAACTGG | 263 | /5Bio/AGGCCAGCCGTATCCGGAAGAACTGG-3' | 273 |
| Patient addition control Rnase P gene Forward primer | AGATTTGGACCTGCGAGCG' | 264 | /5Bio/AGAT/iBiodT/TGGACC/iBiodT/GCGAGCG | |
| Patient addition control Rnase P gene probe | TTCTGACCTGAAGGCTCTGCGCG 5' | 265 | /5AmMC6//iSp18/TTCTGACCTGAAGGCTCTGCGCG | 274 |
| Patient addition control Rnase P gene Reverse primer | GAG CGG CTG TCT CCA CAA GT | 266 | n/a | |

The controls are used to verify the integrity of the assay and to determine whether the results for a given sample are valid or not. Assay integrity is determined using the following processes:

First, for each sample, MFI values for the 4 control bead classes are checked against a corresponding threshold. The thresholds used for the panel are still being determined and cannot be established until the multiplexed assay panel development is complete (i.e., no additional signatures are added). In general, if MFI values for the IC, NC or FC controls are out of range then the results from that sample are deemed invalid and excluded from further analysis.

Second, if the MFI value of the alien armored RNA control is out of range AND none of the MFI values for the 17 agent channels exceed threshold, then the results from that sample are deemed invalid and excluded from further analysis. If the MFI for the alien armored RNA control is out of range AND one or more of the MFI values for the 17 agent channels exceeds threshold, then the results from that sample are deemed valid and included in further analysis. We have observed that agent spikes above certain concentrations can cause a decrease in the alien armored RNA MFI, probably due to competition in the PCR reaction. When the alien armored RNA MFI drops below threshold on a sample considered negative for all signatures, the analysis would be discarded and would need to be repeated. This control reduces the probability of false negatives.

Third, if the MFI values for all four controls are within range, bead counts are checked. First, the bead counts for each of the 4 controls are checked. If the bead count minimum (40 beads) for any of the 4 controls was not reached, then the control MFI values are deemed invalid, and all assay results for that sample are excluded from further analysis.

The final step is to check the individual bead count for each of the 17 signatures for a given sample (non-control beads). If an individual agent bead class (signature) does not reach the bead count minimum (40 beads), that individual assay result is deemed invalid and only that individual result for that signature is removed from the analysis. If the bead counts for any of the agent channels exceeded the minimum, they are considered valid and included in the analysis.

Figure 4:
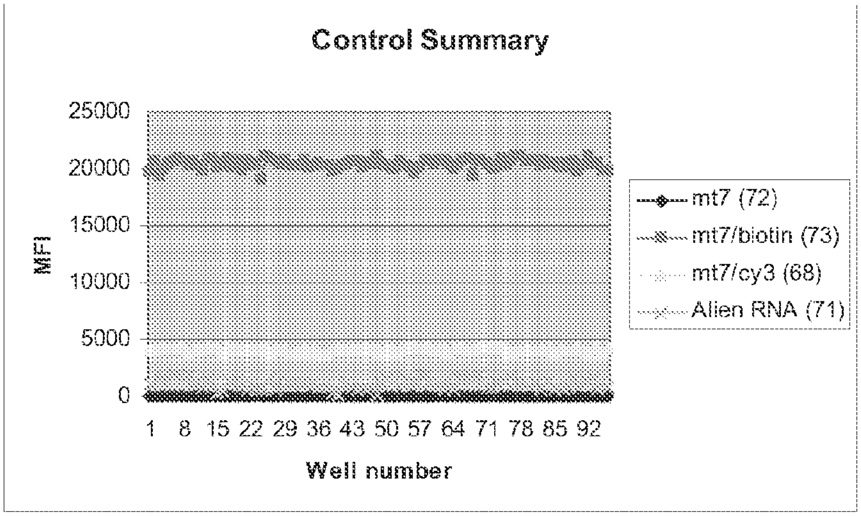
FIG. 4 is a typical plot showing the MFI of four controls recorded in a multiplexed assay PCR assay across a microtiter plate (96-wells, 80 samples tested) and analyzed using a Luminex detector. The log of the median fluorescence intensity (MFI) is plotted on the Y-axis versus sample number shown on the X-axis. Each sample contains 4 internal controls. Controls should produce data that is constant form one sample to the next; therefore data in plots like this one should exhibit 4 straight lines. Fluctuations in MFI values for any of the 4 controls can indicate a problem with the assay. Additionally, each control is characterized by its inherent variation. Some controls produce data that is much less variable than others. The high deviation from point to point shown on this plot from the positive control Alien RNA is expected and normal.
Figure 5A:
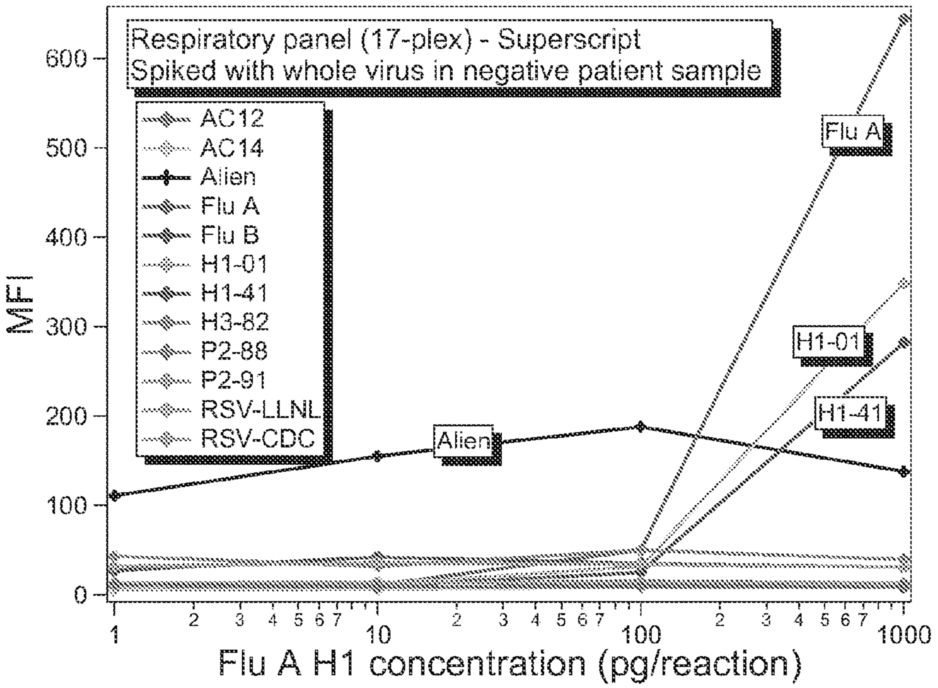
FIG. 5 illustrates detection of Flu A H1, Flu A H3, Flu B, Adeno C, RSV, Para 2, and H5 using the multiplexed, PCR based reagents described herein and negative patient samples spiked with virus.
Figure 5B:
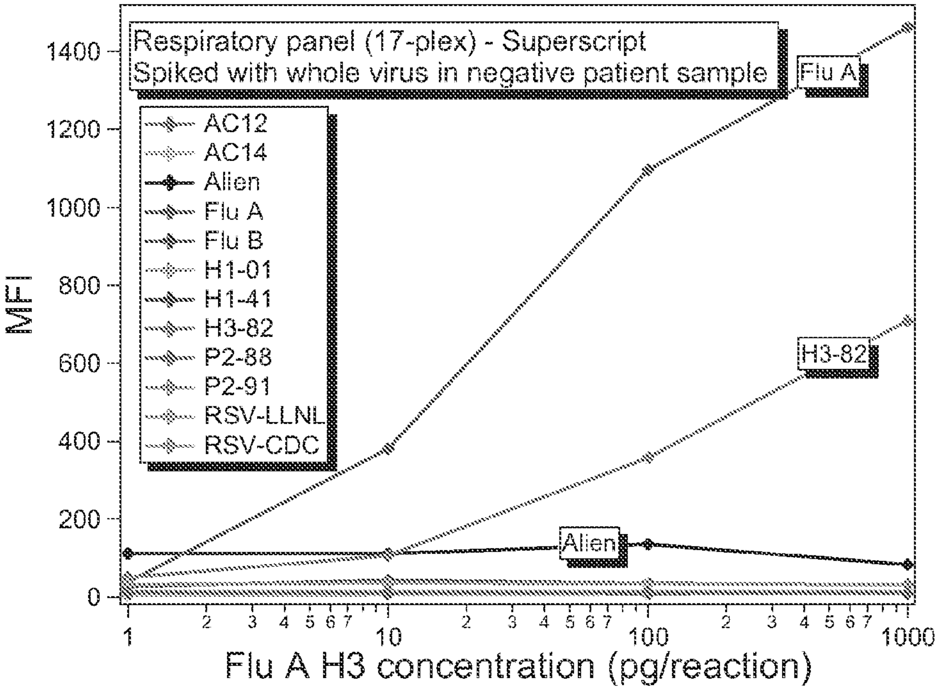
Figure 5C:
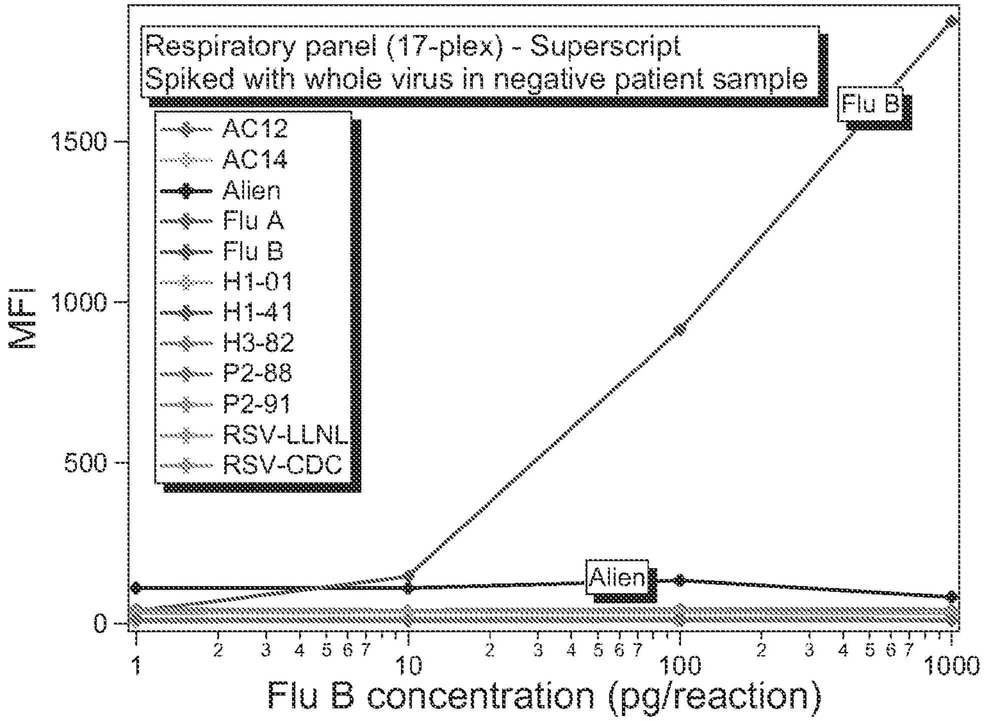
Figure 5D:
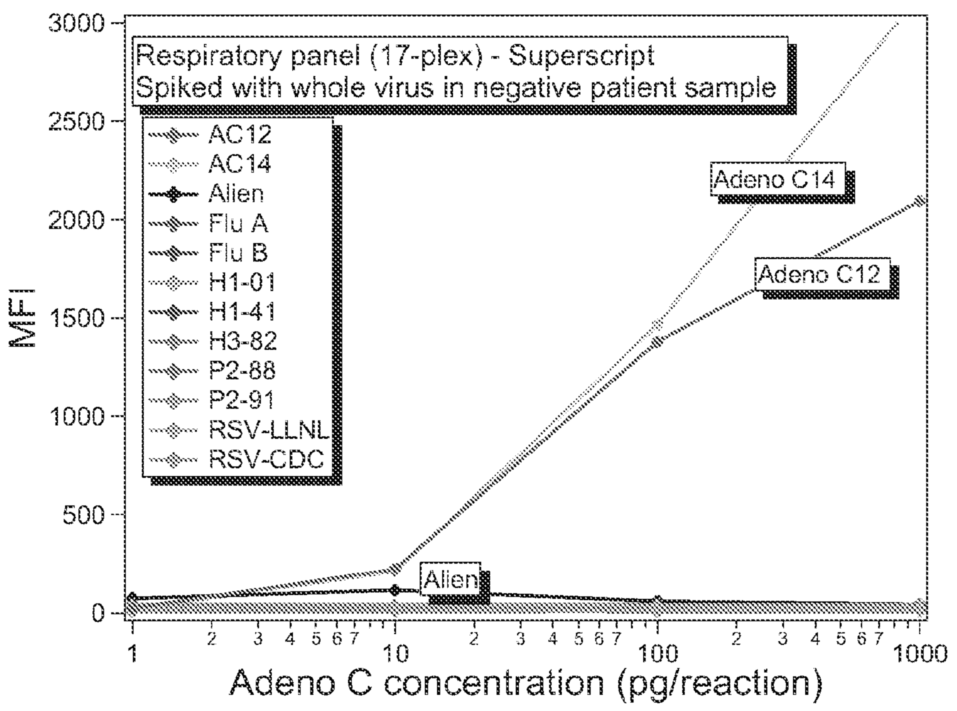
Figure 5E:
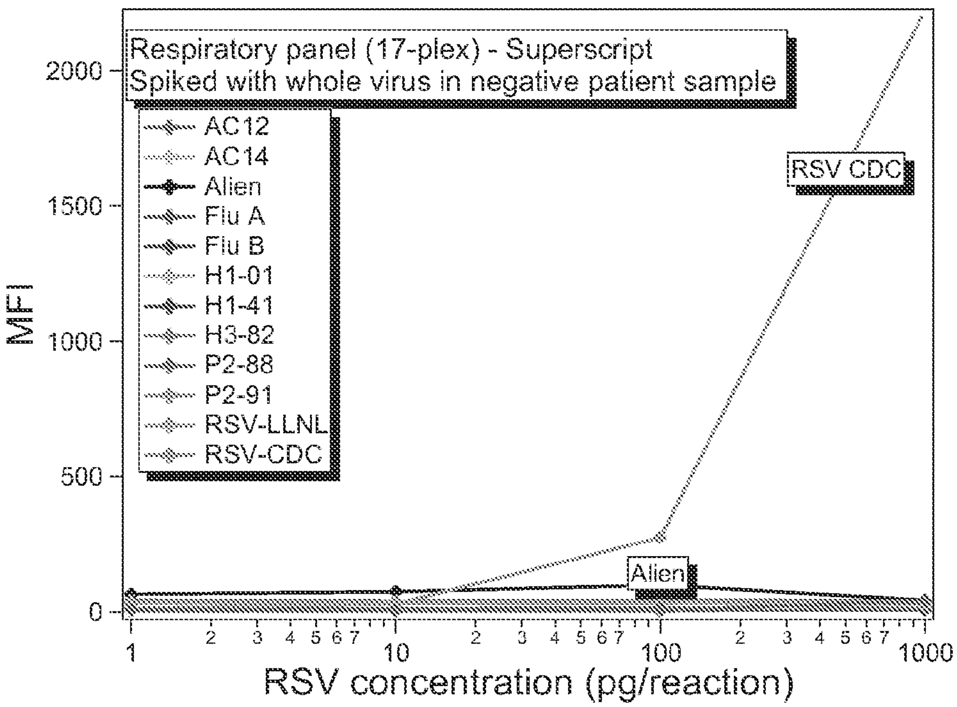
Figure 5F:
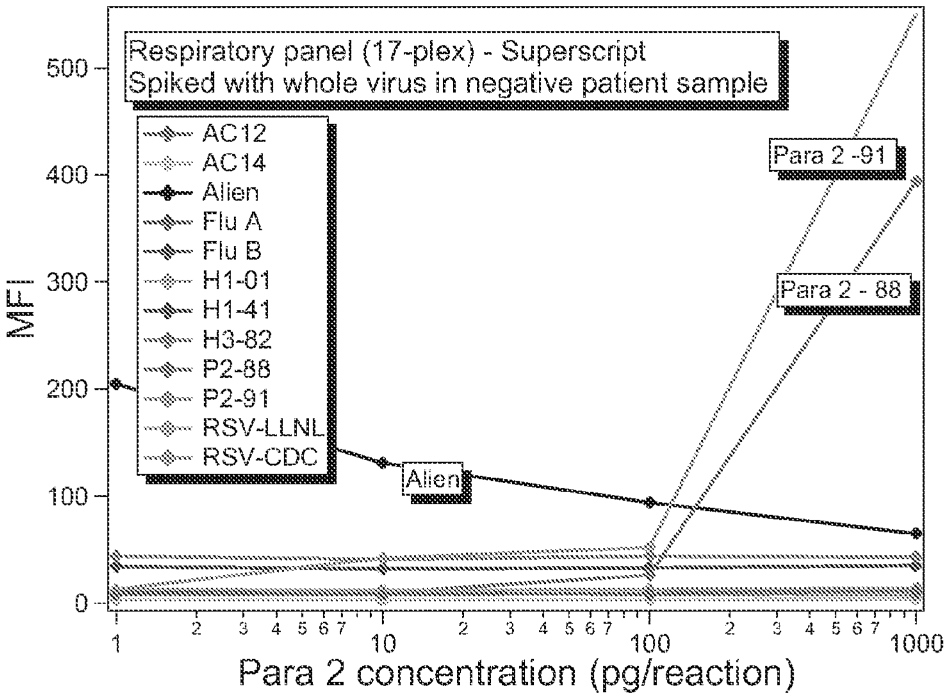
Figure 5G:
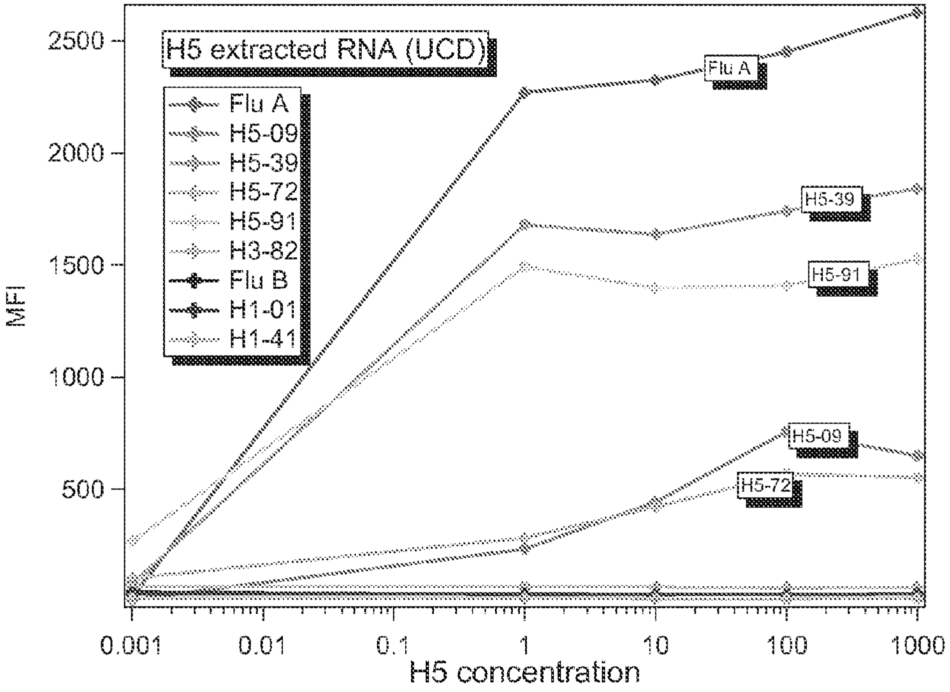

A flow diagram of the process used to determine whether or not any individual assay result is valid or not is shown in FIG. 4.

Example 7

Clinical Samples

From February, 2005 until March, 2006 over 1,200 nasal swab samples were collected from patients arriving in the emergency room at the UC Davis Medical Center (UCDMC) Emergency Department in Sacramento, Calif., which treats ~60,000 patients per year including 12,000 children. Patients were asked if they would like to participate in a study to develop tests for respiratory infections, and nasal swabs were obtained from patients showing respiratory symptoms, as well as volunteers (e.g., accompanying family members) who showed no signs of illness.

Nasal swabs were collected in 3 mL of M4 viral transport medium (Remel, Lenexa, Kans.), which is composed of gelatin, vancomycin, amphotericin B, and colistin. This medium was then de-identified (all procedures had IRB approval) and divided into two tubes. One aliquot was subjected to immunofluorescence testing and viral culture utilizing standard microbiological procedures and/or shell vial culture assays (R-mix, Diagnostic Hybrids, Athens, Ohio). The R-Mix FreshCells™ product is a mixed monolayer of mink lung cells (strain Mv1Lu) and human Adenocarcinoma cells (strain A549). In combination, these cells support the detection of many viruses, in particular those of the respiratory group that includes Influenza A and B, RSV, Adenovirus, and Parainfluenza viruses 1, 2, and 3. The other sample aliquot was reserved for analysis by multiplexed assays, shipped to LLNL on dry ice, and stored at −80° C.

The patient samples were received in our BioSafety Level II (BSL-2) laboratory to be analyzed with our multiplexed respiratory liquid array, as well as with rapid tests available commercially for Flu A & B and RSV (using Remel Xpect Flu A+B, RSV tests). The results obtained on the patient samples by three methods (viral culture/immunofluorescence, Rapid Test, and Multiplexed PCR) were compared. Results are presented below in Example 9.

Example 8

Limits of Detection

The Limit of Detection (LOD) data was recorded in the multiplexed format (all the primers for the signatures listed in the table were present in the PCR mix at 0.4 μM) and all the corresponding probes were present in the bead mix. The PCR reaction was prepared using the Invitrogen Superscript III one step RT PCR kit. The killed target viruses were used as received (no extraction was performed) and diluted from the stock concentration of 1 mg/mL to the desired concentration using negative patient samples collected at the UCDMC. 1 μL of Alien RNA control (200 copies) and 5 μL of target were added to 19 μL of PCR mix for a total volume of 25 μL and PCR was run according to the parameters below:

| | | |
|---|---|---|
| 50.0 C. | 30:00 | 1X |
| 95.0 C. | 15:00 | 1X |
| 94.0 C. | :15 | 35X |
| 55.0 C. | :30 | |
| 72.0 C. | :35 | |
| 4.0 C. | hold | |

Following PCR, 1 μL of amplified product was added to 22 μL of bead mix and hybridized to the probe-coated beads according to the parameters below:

| | | |
|---|---|---|
| 95.0 C. | 2:00 | 1X |
| 55.0 C. | 5:00 | 1X |
| 4.0 C. | hold | |

After hydridization, the beads were washed in Tris-NaCl buffer 3 times using a 96-well microfilter plate fitted with a vacuum pump, labeled with streptavidin-phycoerythrin (3 ng/μL) for 5 min, and washed in Tris-NaCl buffer twice. The beads were then re-suspended into 100 μL of Tris-NaCl buffer and transferred into a 96-well round bottom microtiter plate for analysis on the Bioplex.

The LODs of the multiplexed respiratory panel were measured by running titrations in triplicate for each respiratory virus using successive 10 fold dilutions starting from a maximal concentration of 1000 pg/reaction.

TABLE 6

Killed viruses used.

| Antigen | Source | Conc. (mg/ml) | Volume (ml) | Amount (mg) | Quantity |
|---|---|---|---|---|---|
| Influenza A, Type A (H1N1), Beijing/262/95 | Research Diagnostics | 1.20 | 1.000 | 1.20 | 2 |
| Influenza A, Type A (H1N1), Taiwan | Research Diagnostics | 1.60 | 1.000 | 1.60 | 2 |
| Influenza, Type A (H1N1), Beijing | Advanced Immunochemical | 1.20 | 0.835 | 1.00 | 4 |

TABLE 6-continued

| Killed viruses used. | | | | | |
|---|---|---|---|---|---|
| Antigen | Source | Conc. (mg/ml) | Volume (ml) | Amount (mg) | Quantity |
| Influenza, Type A (H3N2), Kiev like Johannesburg | Advanced Immunochemical | 0.80 | 1.250 | 1.00 | 5 |
| Influenza, Type A (H3N2), Shandong 9/93 | Research Diagnostics | 1.00 | 1.165 | 1.17 | 5 |
| Influenza, Type B, Victoria | Advanced Immunochemical | 1.10 | 1.055 | 1.16 | 5 |
| Parainfluenza, Type 1 | Advanced Immunochemical | 1.15 | 0.870 | 1.00 | 5 |
| Parainfluenza, Type 2 | Advanced Immunochemical | 0.80 | 1.250 | 1.00 | 2 |
| Parainfluenza, Type 3 | Advanced Immunochemical | 1.55 | 0.650 | 1.01 | 2 |
| Respiratory Syncytial Virus | Advanced Immunochemical | 1.30 | 1.540 | 2.00 | 3 |
| Adenovirus | Advanced Immunochemical | 1.00 | 1.000 | 1.00 | 5 |

TABLE 7

| Live viruses used. | | | |
|---|---|---|---|
| Virus | Group | Titer | Quantity (mls) |
| Adenovirus type 1 | C | $10^{9.0}$ $TCID_{50}$/0.1 ml | 45 |
| Adenovirus type 2 | C | $10^{8.5}$ $TCID_{50}$/0.1 ml | 45 |
| Adenovirus type 3 | B | $10^{8.25}$ $TCID_{50}$/0.1 ml | 45 |
| Adenovirus type 4 | E | $10^{8.0}$ $TCID_{50}$/0.1 ml | 45 |
| Adenovirus type 5 | C | $10^{8.0}$ $TCID_{50}$/0.1 ml | 45 |
| Adenovirus type 7 | B | $10^{7..25}$ $TCID_{50}$/0.1 ml | 45 |
| Adenovirus type 21 | B | $10^{7.0}$ $TCID_{50}$/0.1 ml | 45 |

TABLE 8

| Summary of Multiplexed Assay Sensitivity and Specificity. | | | |
|---|---|---|---|
| Pathogen Signature | Limit of Detection (mass of virus/25 μL PCR reaction)** | Background MFI | Cross-reactivity |
| Inf A-CDC | 5 pg/reaction | 11 ± 1 MFI | None detected |
| H1-01 | 50 pg/reaction | 10 ± 1 MFI | None detected |
| H1-41 | 50 pg/reaction | 10 ± 1 MFI | None detected |
| H2-90 | Un-tittered virus | 10 ± 1 MFI | None detected |
| H2-92 | Un-tittered virus | 15 ± 2 MFI | None detected |
| H3-82 | 5 pg/reaction | 45 ± 5 MFI | None detected |
| H5-09 | Un-titered virus* | 10 ± 1 MFI | None detected |
| H5-39 | Un-titered virus* | 75 ± 8 MFI | None detected |
| H5-72 | Un-titered virus* | 15 ± 2 MFI | None detected |
| H5-91 | Un-titered virus* | 350 ± 15 MFI | None detected |
| H7-25 | Un-titered virus* | 65 ± 5 MFI | None detected |
| Inf B-CDC | 5 pg/reaction | 35 ± 3 MFI | None detected |
| Adeno C12 | 5 pg/reaction | 15 ± 2 MFI | None detected |
| Adeno C14 | 5 pg/reaction | 5 ± 1 MFI | None detected |
| Para 2-88 | 50 pg/reaction | 10 ± 1 MFI | None detected |
| Para 2-91 | 5 pg/reaction | 30 ± 3 MFI | None detected |
| RSV-CDC | 20 pg/reaction | 15 ± 2 MFI | None detected |

Example 9

Detection of Respiratory Pathogens in a Multiplexed Format

Successful detection of the various respiratory pathogens in the multiplexed format was demonstrated using a negative patient sample spiked with whole virus and assayed as described herein. All experiments were run in the same conditions, on the same day and the same 96-well plate, using the Superscript III One-step RT-PCR kit. Titrations were recorded in triplicate and the average of 3 data points is plotted for each concentration ranging from 1000 pg/reaction down to 1 pg/reaction. For each of the 6 titrations, a minimum of 4 blanks were run (24 blanks per plate). The data was recorded in the multiplex format, with a 17-plex including the following primer sets: Flu A (1), H1 (3), H3 (1), H5 subtypes (4), Flu B (1), Para 2 (2), Adeno C (2), RSV (2), and the alien positive control (1), for a total of 17 primer sets.

Note that no nucleic acid extraction was performed on the viruses Flu A H1, Flu A H3, Flu BAdeno C, RSV, and Para 2. Whole viruses were diluted in negative patient samples collected in the Emergency Room of the UC Davis Medical Center to simulate positive patient samples in the laboratory and directly spiked on the PCR plate. For H5, fresh dilutions from a stock of extracted H5 RNA (unknown concentration) were used.

FIG. 5 illustrates detection of Flu A H1, Flu A H3, Flu B, Adeno C, RSV, Para 2, and H5. The highest concentration presented on the plot below corresponds to the material spiked at full strength; the second data point is a 10 fold dilution, etc. Only Flu A, Flu B, H1, H3, and H5 MFIs were plotted for clarity. No cross reaction with the other signatures was observed.

Successful detection of respiratory pathogens in patient samples using the multiplexed format was demonstrated using patient samples that had been identified as pathogen positive using standard viral culture techniques. Note that no extraction was performed on the viruses. The patient samples were directly added to the PCR mix without further processing. The positive control in this experiment was Eh.

Figure 6A:
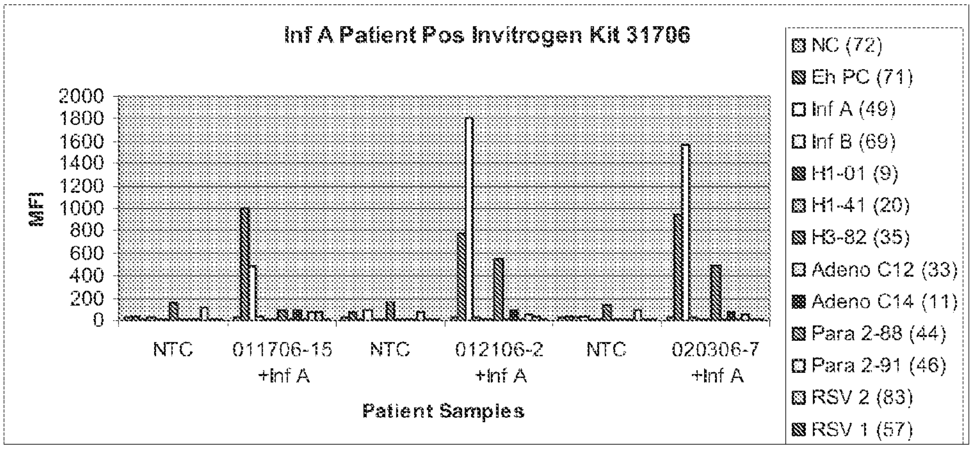
FIG. 6 illustrates detection of respiratory pathogens the multiplexed, PCR based reagents described herein in patient sample determined to be pathogen positive via viral culture.
Figure 6B:
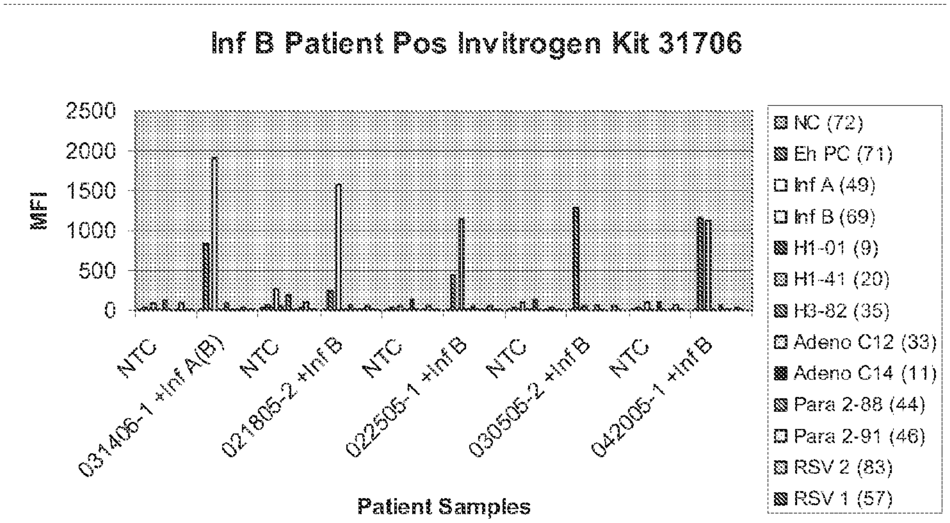
Figure 6C:
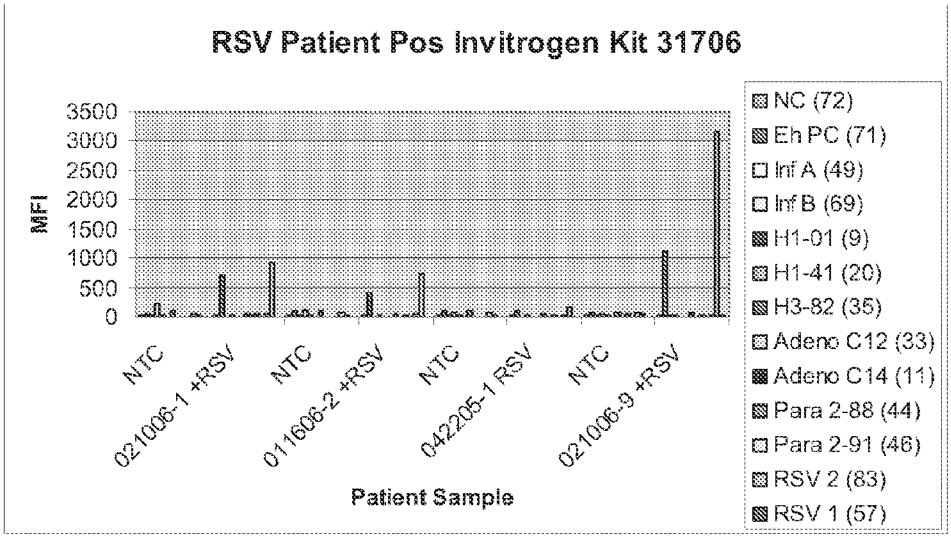

FIG. 6 illustrates the results of the experiments performed on both negative and positive patient samples (samples were determined positive for a pathogen by viral culture). Bar diagrams represent the MFI values of each bead type for each sample, alternating negative controls (NTC) and positive samples.

Example 10

Multiplexed Detection of Respiratory Pathogens Using a Microarray Approach

In another embodiment, the signature sequences used herein are used for detection of pathogens in a sample using a microarray, e.g., a microarray manufactured by Nimblegen Systems. Nimblegen builds its arrays based on photodeprotection chemistry using its proprietary Maskless Array Synthesizer (MAS) system. The Digital Micromirror Device, at the heart of the system, creates digital masks whose design can be easily changed. Up to 390,000 custom oligos can be synthesized onto glass slides within a few hours. To detect the respiratory pathogens, oligonucleotide probes of up to 70 bases long that are complementary to the signature sequences disclosed herein are designed using a set of probe design parameters. Due to the ultra high density, multiple probes from the same sequence can be included on the same chip with on-chip replicates, which increases the confidence in probe calls. A variety of techniques for probe design can be employed, ranging from non-overlapping (sampling) to overlapping (tiling) to the detection of Single Nucleotide Polymorphisms (resequencing, using short oligos.) The pathogen nucleic acid sample is amplified with fluorescently labeled random primers and the labeled DNA is hybridized to the chip. The chip is washed to get rid of non-specifically bound samples and scanned using a laser scanner at high resolution. The raw data and images are analyzed using statistical tools and presence/absence calls are made. Though not as sensitive as Taqman assays and bead assays, microarray allows the detection of presence or absence of multiple viruses simultaneously, and shortens the optimization time for multiplexing assays.

Example 11

Additional Respiratory Pathogen Signature Sequences

Assays were performed as described herein to develop additional multiplexed, Luminex bead based panel for detection of respiratory pathogens without detection of influenza subtypes. These sequences are shown below. Note that for some signature sequences, e.g., RSV-CDC, using a nested primer approach with 2 reverse primers, was useful for detection.

TABLE 9

Additional respiratory pathogen signature sequences

| Pathogen | Oligo Name | Description | Sequence (5'=>3') | SEQ ID NO: | Oligo including linker/label (as applicable) (5'=>3') | SEQ ID NO: |
|---|---|---|---|---|---|---|
| Flu A-CDC | Flu A F171.BF | Forward primer | GAC CRA TCC TGT CAC CTC TGA C | 275 | /5Bio/GAC CRA /iBiodT/CC TGT CAC C/iBiodT/C TGA C | |
| Flu A-CDC | Flu A Pr2491.RCP | Probe | CGTGCCCAGTGAGCGAG GACTGCA | 276 | /5AmMC6//iSp18/CGT GCCCAGTGAGCGAG GACTGCA | 323 |
| Flu A-CDC | Flu A R276.R | Reverse Primer | AGG GCA TTT TGG ACA AAK CGT CTA | 277 | | |
| Flu A-CDC | | Signature sequence Matrix protein 1, segment 7 (gene M1) | GACCAATCCTGTCACCTC TGACTAAGGGGATTTTAG GATTTGTGTTTACGCTCA CCGTGCCCAGTGAGCGAG GACTGCAGCGTAGACGCT TTGTCCAAAATGCCCT | 278 | | |
| Flu A-Syrmis | Flu A-Syrmis.BF | Forward primer | GGACCTCCACTTACTCCA AAACAGAAAC | 279 | /5Bio/GGACC/iBiodT/C CACTTAC/iBiodT/CCA AAACAGAAAC | 324 |
| Flu A-Syrmis | Flu A-Syrmis.FCP | Probe | TTGACCTAGTTGTTCTCG CCA | 280 | /5AmMC6//iSp18/TTG ACCTAGTTGTTCTCG CCA | 325 |
| Flu A-Syrmis | Flu A-Syrmis.R | Reverse Primer | GTAAGGCTTGCATGAATG TTATTTGCTC | 281 | | |
| Flu A-Syrmis | | Signature sequence Nonstructural protein, segment 8 (gene NS1) | GGACCTCCACTTACTCCA AAACAGAAACGGAAAATG GCGAGAACAGCTAGGTCA AAAGTTTGAAGAGATAAG ATGGCTGATTGAAGAAGT GAGACACAGACTAAAAAC AACTGAGAATAGTTTTGA GCAAATAACATTCATGCA AGCATTAC | 282 | | |
| Flu B-CDC | Flu B F760.BF | Forward primer TCG AGC G /iBiodT/CG AGC G | TCC TCA ACT CAC TCT AC/iBiodT/ CAC TCT | 283 | /5Bio/TCC TCA | |
| Flu B-CDC | Flu B Pr8021.RCP | Probe | CACCGCAGTTTCAGCTGC TCGAATTGG | 284 | /5AmMC6//iSp18/CAC CGCAGTTTCAGCTGC TCGAATTGG | 326 |

TABLE 9-continued

| Pathogen | Oligo Name | Description | Sequence (5'=>3') | SEQ ID NO: | Oligo including linker/label (as applicable) (5'=>3') | SEQ ID NO: |
|---|---|---|---|---|---|---|
| Additional respiratory pathogen signature sequences | | | | | | |
| Flu B-CDC | Flu B R860.R | Reverse Primer | CGG TGC TCT TGA CCA AAT TGG | 285 | | |
| Flu B-CDC | | Signature sequence Nonstructural protein, segment 8 (gene NS1) | TCCTCAACTCACTCTTCG AGCGTTTTAATGAAGGAC ATTCAAAGCCAATTCGAG CAGCTGAAACTGCGGTGG GAGTCTTATCCCAATTTG GTCAAGAGCACCG | 286 | | |
| Flu-B-Templeton | Flu B | Forward primer | GTCCATCAAGCTCCAGTT TT | 287 | /5Bio/GTCCA/iBiodT/C AAGCTCCAG/iBiodT/ TTT | 327 |
| Flu-B-Templeton | Flu B | Probe | CCTCCGTCTCCACCTACT TCGTT | 288 | /5AmMC6//iSp18/CCTC CGTCTCCACCTACTT CGTT | 328 |
| Flu-B-Templeton | Flu B | Reverse Primer | TCTTCTTACAGCTTGCTT GC | 289 | | |
| Flu-B-Templeton | | Signature sequence | GTCCATCAAGCTCCAGTT TTGGGCTCCAATGACCAG ATCTGGGGGGAACGAAGT AGGTGGAGACGGAGGGTC TGGCCAAATAAGTTGCAG CCCAGTGTTTGCAGTAGA AAGACCTATTGCTCTAAG CAAGCAAGCTGTAAGAAG A | 290 | | |
| RSV- CDC | RSV_CDC.BF | Forward primer | GGA AAC ATA CGT GAA CAA GCT TCA | 291 | /5Bio/GGA AAC A/iBiodT/A CGT GAA CAA GC/iBiodT/ TCA-3' | 329 |
| RSV- CDC | RSV_CDC.FCP | Probe | TGT GTA TGT GGA GCC TTC GTG AAG CAA G TTC GTG AAG CAA G-3' | 292 | /5AmMC6//iSp18/TGT GTA TGT GGA GCC | 330 |
| RSV- CDC | RSV_CDC.Ra | Reverse Primer (nested) | CAT CGT CTT TTT CTA AGA CAT TGT ATT GA | 293 | | |
| RSV- CDC | RSV_CDC.Rb | Reverse primer (nested) | TCA TCA TCT TTT TCT AGA ACA TTG TAC TGA | 294 | | |
| RSV- CDC | | Signature sequence Matrix protein (gene M)) | GACCAATCCTGTCACCTC TGACTAAGGGGATTTTGG GATTTGTATTCACGCTCA CCGTGCCCAGTGAGCGAG GACTGCAGCGTAGACGCT TTGTCCAAAATGCCCT | 295 | | |
| Para 1-Syrmis | Para 1-Syrmis.BF | Forward primer | ATGCTCCTTGCCCACTGT GAATG | 296 | /5Bio/ATGCTCC/iBiod T/TGCCCACTG/iBiodT /GAATG | |
| Para 1-Syrmis | Para 1-Syrmis.FCP | Probe | TCTATACCTTCACTCGAG TAATCTG | 297 | /5AmMC6//iSp18/TCTA TACCTTCACTCGAGT AATCTG | 331 |
| Para 1-Syrmis | Para 1-Syrmis.R | Reverse Primer | AATCTTTATCCCACTTCC TACACTTG | 298 | | |
| Para 1-Syrmis | | Signature sequence | ATGCTCCTTGCCCACTGT GAATGAGACTACAGATTA CTCGAGTGAAGGTATAGA AGATTTAGTATTTGACAT ATTAGATCTCAAGGGAAA GACCAAATCTCATCGATA CAAAAATGAAGATATAAC TTTTGACCATCCTTTTTC | 299 | | |

TABLE 9-continued

| Additional respiratory pathogen signature sequences | | | | | | |
|---|---|---|---|---|---|---|
| Pathogen | Oligo Name | Description | Sequence (5'=>3') | SEQ ID NO: | Oligo including linker/label (as applicable) (5'=>3') | SEQ ID NO: |
| | | | TGCAATGTATCCAAGTGT AGGAAGTGGGATAAAGAT T | | | |
| Para 3-Syrmis | Para3-Syrmis.BF | Forward primer | ACCAGGAAACTATGCTG CAGAACGGC | 300 | /5Bio/ACCAGGAAAC/i BiodT/ATGC/iBiodT/G CAGAACGGC | 332 and 333 |
| Para 3-Syrmis | Para3 -Syrmis.FCP | Probe | AGAGCTCCTAAACATGAT GGATACC | 301 | /5AmMC6//iSp18/AGA GCTCCTAAACATGA TGGATACC | 334 |
| Para 3-Syrmis | Para3-Syrmis.R | Reverse Primer | GATCCACTGTGTCACCGC TCAATACC | 302 | | |
| Para 3-Syrmis | | Signature sequence | | | | |
| Adeno B-LLNL-01 | Adenovirus B 1770201.BF | Forward primer | TCCTGCACCATTCCCAGA TA | 303 | /5Bio/TCCTGCACCA/i BiodT/TCCCAGA/iBiod T/A | 335 |
| Adeno B-LLNL-01 | Adeno. B 1770201.RCP | Probe | CTGACACGAATAATTCAA GGCTGGAAAGCTG | 304 | /5AmMC6//iSp18/CTG ACACGAATAATTCA AGGCTGGAAAGCTG | 336 |
| Adeno B-LLNL-01 | Adenovirus B 1770201R | Reverse Primer | CCTCCGGGACCTGTTTGT AA | 305 | | |
| Adeno B-LLNL-01 | | Signature sequence L5, E4 | TCCTGCACCATTCCCAGA TAATTTTCAGCTTTCCAG CCTTGAATTATTCGTGTC AGTTCTTGTGGTAAATCC AATCCACACATTACAAAC AGGTCCCGGAGG | 306 | | |
| Adeno B-LLNL-95 | Adenovirus B 1770195.BF | Forward primer | CGCTTTCACAGTCCAACT GC | 307 | /5Bio/CGCTT/iBiodT/C ACAGTCCAAC/iBiodT /GC | 337 |
| Adeno B-LLNL-95 | Adeno. B 1770195.RCP | Probe | CGTTTTCGGATTATGATT CCCATCGTTCTTC | 308 | /5AmMC6//iSp18/CGTT TTCGGATTATGATTC CCATCGTTCTTC | 338 |
| Adeno B-LLNL-95 | Adenovirus B 1770195R | Reverse Primer | GCTGCTTGTGGGTTTGAT GA | 309 | | |
| Adeno B-LLNL-95 | | Signature sequence L5, E4 | CGCTTTCACAGTCCAACT GCTGCGGATGGACTCCGG AGTCTGGATCACGGTCAT CTGGAAGAAGAACGATGG GAATCATAATCCGAAAAC GGTATCGGACGATTGTGT CTCATCAAACCCACAAGC AGC | 310 | | |
| Adeno C-LLNL-12 | Adenovirus C 1768012.BF | Forward primer | AGCGCGTAATATTTGTCT AGGGC | 311 | /5Bio/AGCGCG/iBiodT/ AATATTTGTC/iBiodT/ AGGGC | 339 |
| Adeno C-LLNL-12 | Adeno. C 1768012.RCP | Probe | CGGAACGCGGAAAACAC CTGAGAAAA | 312 | /5AmMC6//iSp18/CGG AACGCGGAAAACAC CTGAGAAAA | 340 |
| Adeno C-LLNL-12 | Adenovirus C 1768012R | Reverse Primer | TCAGCTGACTATAATAAT AAAACGCCA | 313 | | |
| Adeno C-LLNL-12 | | Signature sequence Intergenic region | AGCGCGTAATATTTGTCT AGGGCCGCGGGGACTTTG ACCGTTTACGTGGAGACT CGCCCAGGTGTTTTTCTC AGGTGTTTTCCGCGTTCC GGGTCAAAGTTGGCGTTT | 314 | | |

TABLE 9-continued

| Additional respiratory pathogen signature sequences | | | | | | |
|---|---|---|---|---|---|---|
| Pathogen | Oligo Name | Description | Sequence (5'=>3') | SEQ ID NO: | Oligo including linker/label (as applicable) (5'=>3') | SEQ ID NO: |
| | | | TATTATTATAGTCAGCTGA | | | |
| Adeno C-LLNL-14 | Adenovirus C 1768014.BF | Forward primer | TCGATCTTACCTGCCACGAG | 315 | /5Bio/TCGA/iBiodT/CTTACC/iBiodT/GCCACGAG | |
| Adeno C-LLNL-14 | Adeno. C 1768014.RCP | Probe | TGCTCCACATAATCTAACACAAACTCCTCACCC | 316 | /5AmMC6//iSp18/TGCTCCACATAATCTAACACAAACTCCTCACCC | 341 |
| Adeno C-LLNL-14 | Adenovirus C 1768014R | Reverse Primer | GCCACAGGTCCTCATATAGCAA | 317 | | |
| Adeno C-LLNL-14 | | Signature sequence 32 kD protein (gene EIA/2652980)e | TCGATCTTACCTGCCACGAGGCTGGCTTTCCACCCAGTGACGACGAGGATGAAGAGGGTGAGGAGTTTGTGTTAGATTATGTGGAGCACCCCGGGCACGGTTGCAGGTCTTGTCATTATCACCGGAGGAATACGGGGGACCCAGATATTATGTGTTCGCTTTGCTATATGAGGACCTGTGGC | 318 | | |
| Adeno E-LLNL-58 | Adenovirus E 1759558.BF | Forward primer | TGCAATTTTGTTGGGTTTCG | 319 | /5Bio/TGCAAT/iBiodT/TTGTTGGGT/iBiodT/TCG | |
| Adeno E-LLNL-58 | Adeno. E 1759558.RCP | Probe | TTAATCATGGTTCTTCCTGTTCTTCCCTCCC | 320 | /5AmMC6//iSp18/TTAATCATGGTTCTTCCTGTTCTTCCCTCCC | 342 |
| Adeno E-LLNL-58 | Adenovirus E 1759558R | Reverse Primer | CCTGGCTGTTATTTTCCACCA | 321 | | |
| Adeno E-LLNL-58 | | Signature sequence E4 | TGCAATTTTGTTGGGTTTCGGTGACGGCGGGGGAGGGAAGAACAGGAAGAACCATGATTAACTTTTAATCCAAACGGTCTCGGAGTACTTCAAAATGAAGATCGCGGAGATGGCACCTCTCGCCCCCGCTGTGTTGGTGGAAAATAACAGCCAGG | 322 | | |

Example 12

Additional Primers and Probes for Subtyping Influenza

Using the in-silico identification techniques described herein, additional primers and probes useful for influenza subtyping were determined as follows.

TABLE 10

Primer and probe sets for influenza subtyping

| Signature | Forward Primer (5'=>3') (Forward Primer sequences disclosed as SEQ ID NOS 343-353, respectively, in order of appearance) | Reverse primer (5'=>3') (Reverse Primer sequences disclosed as SEQ ID NOS 354-364, respectively, in order of appearance) | Luminex Probe (5'=>3') (Probe sequences disclosed as SEQ ID NOS, 365-375, respectively, in order of appearance) |
|---|---|---|---|
| Inf A-CDC | GACCRATCCTGTCACCTCTGAC | AGGGCATTTTGGACAAAAKCGTCTA | CGTGCCCAGTGAGCGAGGACTGCA |
| H1-01 | CTTTCAGCTACAGATGCAGACACA | TTCCCATTGTGACTGTCCTCAA | CGAACAATTCAACCGACACTGTTGACACA |
| H1-41 | GCCATTAACGGGATTACAAACAAG | CCAGTAGAACCAACAATTCTGCATTATTG | TCGAGAAAATGAACACTCAATTCACAGCTG |
| H2-90 | CCCTAGTTCAAGTGGAGGGATTC | ACCGAGACGGTCGACACAA | CATGGGTCACAGTGACATTCCGCTCTAGA |
| H2-92 | ACACAATCTTGGAGCGAAACG | ACTATATAGGACCATTCAGGCACTT | TGCAGATTAAGCGGGATCCCTCCAT |
| H3-82 | ATGCTGAGGATATGGGCAATG | GATATGGCAAAGGAAATCCATAGG | CATTAAACAACCGGTTCCAGATCAAAGGTGT |
| H5-09 | GATCTAAATGGAGTGAAGCCTCTCAT | TATGTAAGACCATTCCGGCACAT | CTGGATGGCTCCTCGGAAACCCTATGT |
| H5-39 | GGGAGGAAATAGACGGAGTCAAA | TAGATGCAAATTCTGCACTGCAA | TCAACAGTGGCGAGTTCCCTAGCACTG |
| H5-72 | GTATGGGTACCACCATAGCAATGA | TGTTCATTTTGTCAATGATCGAGTT | TGCAGACAAAGAATCCACTCAAAAGGCAA |
| H5-91 | GACAATGAATGTATGGAAAGTGTGAGA | ATCCAAAAAGATAGACCAGCTATCATG | CAGTGGCAAGTTCCCTAGCACTGGCA |
| H7-25 | GATCCCAATGACACAGTGACCTT | TTCCCCACAGTTCTAGGGTTGA | CATAGCCCCTGACAGGGCAAGTTTCTTTAG |

For detection of the signature sequences via amplification, primers suitable for PCR were designed and are disclosed in Table 10. The forward and reverse primers in Table 10 are used for PCR based detection of respiratory pathogens in a sample via detection of the signature sequences disclosed in Table 10 in the sample. Detection of the amplicon, e.g., the amplified signature sequence, is performed using an agarose gel.

For detection of signature sequences using real-time PCR, probes suitable for Taqman PCR were designed and are disclosed in Table 10. The primers and probes in Table 10 are used for Taqman PCR based detection of respiratory pathogens in a sample via detection of the signature sequences disclosed in Table 10 in a sample. Detection of the amplicon, e.g., the amplified signature sequence, is performed using an iCycler.

The primers and probes are also used for Luminex based detection of the signature sequences in Table 10. Probes are covalently attached to fluorescent microbeads and hybridized to samples subjected to PCR using the disclosed primers.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A kit for determining the presence or absence of influenza A, influenza B, parainfluenza (type 2), respiratory syncytial virus, and adenovirus in a sample, said kit comprising nucleic acid reagents for nucleic acid amplification of 17 amplicons each consisting of a signature sequence selected from the group consisting of SEQ ID NOS: 1, 7, 13, 19, 25, 31, 37, 43, 49, 55, 61, 67, 73, 79, 85, 91, and 97 wherein the nucleic acid reagents comprise 34 forward and reverse primer oligonucleotides each consisting of one nucleic acid sequence selected from the group consisting of SEQ ID NOS: 2, 3, 8, 9, 14, 15, 20, 21, 26, 27, 32, 33, 38, 39, 44, 45, 50, 51, 56, 57, 62, 63, 68, 69, 74, 75, 80, 81, 86, 87, 92, 93, 98, and 99.

2. A method for determining the presence or absence of influenza A, influenza B, parainfluenza (type 2), respiratory syncytial virus, and adenovirus in a sample, said method comprising the steps of contacting the sample with the nucleic acid reagents in the kit of claim 1 and performing an nucleic acid amplification assay, wherein the presence or absence of at least one amplicon consisting of one signature sequence in the sample indicates the presence or absence of influenza A, influenza B, parainfluenza (type 2), respiratory syncytial virus, or adenovirus in the sample.

3. The kit of claim 1, where each forward primer is labeled with biotin.

4. The kit of claim 3, wherein each forward primer is labeled with a 5' biotin and 2 internal biotins.

5. The kit of claim 1, further comprising 17 hybridization probe oligonucleotides each consisting of one nucleic acid sequence selected from the group consisting of SEQ ID NOS: 4, 10, 16, 22, 28, 34, 40, 46, 52, 58, 64, 70, 76, 82, 88, 94, and 100.

6. The kit of claim 5, wherein each hybridization probe comprises a reactive amine and a C18 spacer (5AmMC12//iSp18) at the 5' end.

7. The kit of claim 5, wherein each hybridization probe is coupled to a carboxylated fluorescent microbead.

8. The kit of claim 6, wherein each hybridization probe is coupled to a carboxylated fluorescent microbead.

9. The kit of claim 5, wherein each forward primer is labeled with a 5' biotin and 2 internal biotins.

10. The kit of claim 6, wherein each forward primer is labeled with a 5' biotin and 2 internal biotins.

11. The kit of claim 7, wherein each forward primer is labeled with a 5' biotin and 2 internal biotins.

12. The kit of claim 8, wherein each forward primer is labeled with a 5' biotin and 2 internal biotins.

13. The kit of claim 1, further comprising 17 hybridization probe oligonucleotides each consisting of one nucleic acid sequence selected from the group consisting of SEQ ID NOS: 6, 12, 18, 24, 30, 36, 42, 48, 54, 60, 66, 72, 78, 84, 90, 96, and 102.

14. The kit of claim 13, where each hybridization probe comprises a fluorophore and quencher.

15. A method for determining the presence or absence of influenza A, influenza B, parainfluenza (type 2), respiratory syncytial virus, and adenovirus in a sample, said method comprising the steps of contacting the sample with the nucleic acid reagents in the kit of claim 4 and performing an nucleic acid amplification assay, wherein the presence or absence of at least one amplicon consisting of one signature sequence in the sample indicates the presence or absence of influenza A, influenza B, parainfluenza (type 2), respiratory syncytial virus, or adenovirus in the sample.

16. A method for determining the presence or absence of influenza A, influenza B, parainfluenza (type 2), respiratory syncytial virus, and adenovirus in a sample, said method comprising the steps of contacting the sample with the nucleic acid reagents in the kit of claim 5 and performing an nucleic acid amplification assay, wherein the presence or absence of at least one amplicon consisting of one signature sequence in the sample indicates the presence or absence of influenza A, influenza B, parainfluenza (type 2), respiratory syncytial virus, or adenovirus in the sample.

17. A method for determining the presence or absence of influenza A, influenza B, parainfluenza (type 2), respiratory syncytial virus, and adenovirus in a sample, said method comprising the steps of contacting the sample with the nucleic acid reagents in the kit of claim 12 and performing an nucleic acid amplification assay, wherein the presence or absence of at least one amplicon consisting of one signature sequence in the sample indicates the presence or absence of influenza A, influenza B, parainfluenza (type 2), respiratory syncytial virus, or adenovirus in the sample.

18. A method for determining the presence or absence of influenza A, influenza B, parainfluenza (type 2), respiratory syncytial virus, and adenovirus in a sample, said method comprising the steps of contacting the sample with the nucleic acid reagents in the kit of claim 13 and performing an nucleic acid amplification assay, wherein the presence or absence of at least one amplicon consisting of one signature sequence in the sample indicates the presence or absence of influenza A, influenza B, parainfluenza (type 2), respiratory syncytial virus, or adenovirus in the sample.

* * * * *